(12) United States Patent
Beall et al.

(10) Patent No.: US 7,943,379 B2
(45) Date of Patent: May 17, 2011

(54) PRODUCTION OF RAAV IN VERO CELLS USING PARTICULAR ADENOVIRUS HELPERS

(75) Inventors: Clifford J. Beall, Gahanna, OH (US); Kelly R. Clark, Columbus, OH (US); Philip R. Johnson, Jr., Wynnewood, PA (US)

(73) Assignee: Nationwide Children's Hospital, Inc., Columbus, OH (US)

( * ) Notice: Subject to any disclaimer, the term of this patent is extended or adjusted under 35 U.S.C. 154(b) by 0 days.

(21) Appl. No.: 12/433,876

(22) Filed: Apr. 30, 2009

(65) Prior Publication Data
US 2009/0275138 A1 Nov. 5, 2009

Related U.S. Application Data

(60) Provisional application No. 61/049,257, filed on Apr. 30, 2008.

(51) Int. Cl.
*C12N 15/861* (2006.01)
*C12N 7/00* (2006.01)
*C12Q 1/70* (2006.01)

(52) U.S. Cl. ............... 435/457; 435/235.1; 435/325; 435/5

(58) Field of Classification Search .................. None
See application file for complete search history.

(56) References Cited

U.S. PATENT DOCUMENTS
5,658,785 A 8/1997 Johnson
2004/0224411 A1 11/2004 Clark et al.

OTHER PUBLICATIONS

Li and Samulski, Serotype-specific replicating AAV helper constructs increase recombinant AAV type 2 vector production, 2005, Virology, vol. 335, pp. 10-21.*
Adeno-X expression system 1 User Manual, pp. 46-47 (Aug. 2007 version, protocol PT3414-1, version PR7823350), Clontech Laboratories, Inc. (Mountain View, CA).
Aitken et al., "A Phase I Study of Aerosolized Administration of tgAAVCF to Cystic Fibrosis Subjects with Mild Lung Disease," Hum Gene Therapy, 12:1907-1916 (2001).
Berkner et al., "Generation of adenovirus by transfection of plasmids," Nucleic Acids Res 11(17): 6003-20 (1983).
Carter et al., "Adeno-associated Virus and AAV Vectors for Gene Delivery" in Gene and Cell Therapy: Therapeutic Mechanisms and Strategies, Second Edition (Ed. N. Templeton-Smith), Chapter 5, pp. 71-101, Marcel Dekker, Inc., New York (2004).
Carter, "Adeno-Associated Virus Helper Functions," in Handbook of Parvoviruses, vol. I, (P. Tjissen, Ed.) CRC Press, Boca Raton, Chapter 13, pp. 255-282 (1989).
Chen et al., "Molecular Characterization of Adeno-Associated Viruses Infecting Children," J Virol 79:14781-14792 (2005).
Clark et al., "Highly Purified Recombinant Adeno-Associated Virus Vectors are Biologically Active and Free of Detectable Helper and Wild-Type Viruses," Hum Gene Ther 10:1031-1039 (1999).
Clark et al., "Cell Lines for the Production of Recombinant Adeno-Associated Virus," Hum. Gene Ther 6:1329-1341 (1995).
Collaco et al. "A helper virus-free packaging system for recombinant adeno-associated virus vectors," Gene 238:397-405 (1999).
Conway et al., "High-tier recombinant adeno-associated virus production utilizing a recombinant herpes simplex virus type I vector expressing AAV-2 Rep and Cap," Gene Ther 6:986-993 (1999).
Ferrari et al., "Second-Strand Synthesis Is a Rate-Limiting Step for Efficient Transduction by Recombinant Adeno-Associated Virus Vectors," J Virol 70:3227-3234 (1996).
Fisher et al. "A Novel Adenovirus-Adeno-Associated Virus Hybrid Vector That Displays Efficient Rescue and Delivery of the AAV Genome," Hum Gene Ther 7:2079-2087 (1996).
Gao et al., "High-Tier Adeno-Associated Viral Vectors from a Rep/Cap Cell Line and Hybrid Shuttle Virus," Hum Gene Ther 9:2353-2362 (1998).
Gao et al., "Rep/Cap Gene Amplification and High-Yield Production of AAV in an A549 Cell Line Expressing Rep/Cap," Mol Ther 5:644-649 (2002).
Grimm et al., "Novel Tools for Production and Purification of Recombinant Adenoassociated Virus Vectors," Hum Gene Ther 9:2745-2760 (1998).
Handa et al., "Adeno-associated Virus DNA Replication Complexes in Herpes Simplex Virus or Adenovirus-infected Cells," Journal of Biological Chemistry 254(14): 6603-6610 (1979).
Hirt et al., "Selective Extraction of Polyoma DNA from Infected Mouse Cell Cultures," Journal of Molecular Biology, 26(2): 365-369 (1967).
Inoue et al., "Packaging Cells Based on Inducible Gene Amplification for the Production of Adeno-Associated Virus Vectors," J Virol 72:7024-7031 (1998).
Kidd et al., "Human and Simian Adenoviruses: Phylogenetic Inferences from Analysis of VA RNA Genes," Virology 207(1): 32-45 (1995).
Li et al., "Role for Highly Regulated *rep* Gene Express on in Adeno-Associated Virus Vector Production," J Virol 71:5236-5243 (1997).
Liu et al., "Selective *Rep-Cap* Gene Amplification as a Mechanism for High-Tier Recombinant AAV Production from Stable Cell Lines," Mol Ther. 2:394-403 (2000).
Liu et al., "Production of recombinant adeno-associated virus vectors using a packaging cell lines and a hybrid recombinant adenovirus," Gene Ther. 6:293-299 (1999).
Liu et al., "Efficient Site-Specific Integration of Large Transgenes by an Enhanced Herpes Simplex Virus/Adeno-Associated Virus Hybrid Amplicon Vector," Journal of Virology 80(4): 1672-1679 (2006).
Matsushita et al., "Adeno-associated virus vectors can be efficiently produced without helper virus," Gene Ther 5:938-945 (1998).
Muzyczka, "Use of Adeno-Associated Virus as a General Transduction Vector for Mammalian Cells," Current Topics in Microbiology and Immunology, 158: 97-129 (1992).

(Continued)

*Primary Examiner* — Bo Peng
(74) *Attorney, Agent, or Firm* — Marshall, Gerstein & Borun LLP

(57) ABSTRACT

The present invention relates to methods and materials for recombinant adeno-associated virus production. More particularly, in some embodiments the invention contemplates the use of an adenovirus known as Simian Adenovirus 13 (SAdV-13) and Vero cells for production of recombinant adeno-associated virus (rAAV).

11 Claims, 4 Drawing Sheets

OTHER PUBLICATIONS

Ng, et al., "Helper-dependent Adenoviral Vectors for Gene Therapy" in Gene and Cell Therapy, Therapeutic Mechanisms and Strategies, Chapter 4, pp. 53-70, Marcel Dekker, Inc., New York (2004).

Nguyen et al, "Mouse adenovirus (MAV-1) expression in primary human endothelial cells and generation of a full-length infectious plasmid," Gene Therapy 6:1291-1297 (1999).

Ogasawara et al., "The Use of Heterologous Promoters for Adeno-Associated Virus (AAV) Protein Expression in AAV Vector Production," Microbiol Immunol 42:177-185 (1998).

Richardson et al., "Vero cells injected with adenovirus type 2 mRNA produce authentic viral polypeptide patterns: Early mRNA promotes growth of adenovirus-associated virus," Proc Natl Acad Sci USA 77(2): 931-935 (1980).

Ruffing et al., "Mutations in the carboxy terminus of adeno-associated virus 2 capsid proteins affect viral infectivity: lack of an RGD integrin-binding motif," J. Gen. Virol., 75: 3385-3392 (1994).

Salvetti et al., "Factors Influencing Recombinant Adeno-Associated Virus Production," Hum Gene Ther 9:695-706 (1998).

Schwartz et al., "Adenovirus types 8 and 19 infection of rabbit corneal organ cultures," Invest Ophthalmol Vis Sci. 18(9):956-63 (1979).

Srivastava et al., "Nucleotide Sequence and Organization of the Adeno-Associated Virus 2 Genome," J. Virol., 45: 555-564 (1983).

Tamayose et al., "A New Strategy for Large-Scale Preparation of High-Titer Recombinant Adeno-Associated Virus Vectors by Using Packaging Cell Lines and Sulfonated Cellulose Column Chromatography," Hum Gene Ther 7:507-513 (1996).

Thrasher et al., "Generation of recombinant adeno-associated virus (rAAV) from an adenoviral vector and functional reconstitution of the NADPH-oxidase," Gene Ther 2:481-485 (1995).

Vincent et al., "Analysis of Recombinant Adeno-Associated Virus Packaging and Requirements for *rep* and *cap* Gene Products," J Virol 71:1897-1905 (1997).

Vincent et al., "Modern Approaches to New Vaccines Including Prevention of Aids," Vaccine 90: 353-359 (1990).

Xiao et al., "Production of High-Titer Recombinant Adeno-Associated Virus Vectors in the Absence of Helper Adenovirus," J Virol 72:2224-2232 (1998).

* cited by examiner

SEQUENCE LISTING

```
<160> NUMBER OF SEQ ID NOS: 50

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
tggaaatccc cgtgagtcaa                                            20

<210> SEQ ID NO 2
<211> LENGTH: 19
<212> TYPE: DNA
<213> ORGANISM: Artificial Sequence
<220> FEATURE:
<223> OTHER INFORMATION: Synthetic primer

<400> SEQUENCE: 2
```

-continued catggtgatg cggttttgg                                                         19

<210> SEQ ID NO 3
<211> LENGTH: 22
<212> TYPE: DNA
<213> ORGANISM: Artificial sequence
<220> FEATURE:
<223> OTHER INFORMATION: Synthetic probe

<400> SEQUENCE: 3
ccgctatcca cgcccattga tg                                                     22

<210> SEQ ID NO 4
<211> LENGTH: 21
<212> TYPE: DNA
<213> ORGANISM: Artificial sequence
<220> FEATURE:
<223> OTHER INFORMATION: Synthetic primer

<400> SEQUENCE: 4
ccactacctg agcacccagt c                                                      21

<210> SEQ ID NO 5
<211> LENGTH: 20
<212> TYPE: DNA
<213> ORGANISM: Artificial sequence
<220> FEATURE:
<223> OTHER INFORMATION: Synthetic primer

<400> SEQUENCE: 5
tccagcagga ccatgtgatc                                                        20

<210> SEQ ID NO 6
<211> LENGTH: 25
<212> TYPE: DNA
<213> ORGANISM: Artificial sequence
<220> FEATURE:
<223> OTHER INFORMATION: Synthetic probe

<400> SEQUENCE: 6
tgagcaaaga ccccaacgag aagcg                                                  25

<210> SEQ ID NO 7
<211> LENGTH: 19
<212> TYPE: DNA
<213> ORGANISM: Artificial sequence
<220> FEATURE:
<223> OTHER INFORMATION: Synthetic primer

<400> SEQUENCE: 7
tggctggagt gcgatcttc                                                         19

<210> SEQ ID NO 8
<211> LENGTH: 19
<212> TYPE: DNA
<213> ORGANISM: Artificial sequence
<220> FEATURE:
<223> OTHER INFORMATION: Synthetic primer

<400> SEQUENCE: 8
cgtgcatctg ccagtttga                                                         19

<210> SEQ ID NO 9
<211> LENGTH: 24
<212> TYPE: DNA
<213> ORGANISM: Artificial sequence

```
<220> FEATURE:
<223> OTHER INFORMATION: Synthetic probe

<400> SEQUENCE: 9
tgaggccgat actgtcgtcg tccc                                            24

<210> SEQ ID NO 10
<211> LENGTH: 19
<212> TYPE: DNA
<213> ORGANISM: Artificial sequence
<220> FEATURE:
<223> OTHER INFORMATION: Synthetic primer

<400> SEQUENCE: 10
ggagtggagc cgagacaac                                                  19

<210> SEQ ID NO 11
<211> LENGTH: 19
<212> TYPE: DNA
<213> ORGANISM: Artificial sequence
<220> FEATURE:
<223> OTHER INFORMATION: Synthetic primer

<400> SEQUENCE: 11
actacgtccg gcgttccat                                                  19

<210> SEQ ID NO 12
<211> LENGTH: 28
<212> TYPE: DNA
<213> ORGANISM: Artificial sequence
<220> FEATURE:
<223> OTHER INFORMATION: Synthetic probe

<400> SEQUENCE: 12
tggcatgaca ctacgaccaa cacgatct                                        28

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
cttgaagcca cgcaagttta                                                 20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
tgcaaataat ccagcaaagc                                                 20

<210> SEQ ID NO 15
<211> LENGTH: 20
<212> TYPE: DNA
<213> ORGANISM: Artificial Sequence
<220> FEATURE:
<223> OTHER INFORMATION: Synthetic probe

<400> SEQUENCE: 15
catgtttgct catcgcccgg                                                 20
```

```
<210> SEQ ID NO 16
<211> LENGTH: 32938
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: SAdV-13 Viral Genome

<400> SEQUENCE: 16
catcatcaat aatatacctt acaatgtaaa cagaagttaa tatgcaaatg agatgggcgt      60
gtccacaact gtgattggcc gtgacgtcaa tgggcgggcc ggtgggcggt tcgggcgggg     120
cgcgtcgtgg gaaaattacg caattattag tcattaggga tgggctgacc gcacgtgcgt     180
catatgcgga agtgcggaat ttttaactgt ttgcatgtta aatttactgt gtattgggca     240
aattttgaac gcggaagtgt ttattaaaaa aattaccggg tgacgaatgg gtggaatatt     300
taccgagggc cggggagact ttgacctatt acgtgtggta tcgggcgta ttttttttgg      360 tcacgtttcc gcgaagggtc aaaagtcccg ttttattgct ctcagtcagg tgattgtcag     420
ggtatttaaa ccggagcaga acgtcaagag gccactcttg agtgccagcg agaagagttt     480
tctcctcggg ctcttcagtt gacttgaaga agataagaaa aaatgagaac tccgcttgtg     540
gagggagata ttcccgttcg gttcgcggcg gagctgttgg ctgctttggc agaagaggta     600
tttgccgatg tggaacctcc acgggcgttt gaagatgtgt ctctgcatga tttatttgat     660
ttagatgtgg aagatagaga agatcccagt caagatgcgg tagatatgct gtttccagag     720
tctctgttgc ttgctgcgga ggagggtata gatataccct gagacactcc acctcctttg     780
gagcctccga tggtgttaag tccactcagt cagcagcagc aggatatgcc tgatttaact     840
gtgggcgatg tgaatttact gtgttctgaa agtagcttct ccagtttgga ggaaaatgag     900
ctggagaggt gtatggcaga actggccgct agcggtgtgg caagcgtacg ggagcaggaa     960
agggaagaaa tgtcaggtac gccgtttaat ttggactatc agaaatgcc tggctatgga     1020 tgcaagtcct gtcagtacca tcgtgagcag actggggagg ctgatatttt atgttctttg     1080
tgttacctga gacgtaatgg cgtgtttgtt tacagtaagt tgtggaccac ctggtggtgg     1140
ggagggaaca tgtgtgtgtg tggttagatt ttaatgtttt ttttaatttt aaggtcctgt     1200
gtcagaggcg gaagtagatg agcctgatac aactactgat gatcagggc gtgcgcagtc      1260 tccacccaag ctgacccagg atgcacctgt taatgttatt agacctcgtc ctattaggcc     1320
atcgtcacgt cgcaggaatg ctgtagacag cttggaatcg ctgctggaag atgatgactg     1380
tgaacctttg gacttgacct taaacgtgc cagatattag gcgttactgt ttgtgtaatt      1440
aaacgtgcca ggcgttgctg tatttatgtt ctgtgagtca tgtgtaaata agattaagt     1500 actgtgtaaa tagttattgg gtcattgttt gaatagaaga gtgggaggga ttaagtgttt     1560
gttataagag caatgaagag gcctgtggct gcagaagtcc aaatgagct tgacaggctg     1620 ttagagaatt ataacagctt aagaagggtt ttagaagagg cgtctgaaga tacttcagtt     1680
tggtggcgca agtgtttgg gtgtagagtt agtcagttag tagttcaggc taaagttgaa     1740
tataaggaag aatttgagaa actttttca gaggtgcctg gacttgtgga ctctctaaat     1800
ttttgccatc acgcttttt ttacgagaag gttattgcg gcttggattt ttgcactccc       1860
ggacgcacta ttgcagcttt ggcttttgc gctttattt tagataagtg gaataaggag       1920
actcatctca gtaaaggata tactttagat tacattagtt tgcagctatg gaaggcttac     1980
atgaggaagg ggaagatcta caccttctcg caggggccgc ggtcgctgcc gcagcgggtg     2040
```

```
cggaggcggt tggggttcaa gacagaggac caaacgcgct tgctggaggc cgaggaggag    2100
cccagggcgg ggacggatcc cccgagcgag acttgagtga cgaccaggag gtgcccgctg    2160
cggtggggcc tattccggac ccttttcctg agctgcgtag acatttgttg cgttctcctg    2220 gtcggggct ggaagaagat cctggggaag ggggagtgg agaacaaaga gggattaaga     2280
gacctagaga gggacggaag gtggaaggca taatgagcga gttgacttta agtttgatga    2340
ctagaaagag gacagaaaac aagtggctca gtgagatatg ggatgagttt agaactggtg    2400
atatgtatct tcagacaaag tacactttg agcaggtttt taccaagtgg ttaaatccag     2460
aagatgattg ggaagacgct ttaacgcgtt atggaaaggt ggctttaagg cccgatacaa    2520
agtatcgttt gactaaaaaa gtggaactca gaagctgtgc ttatgttatt ggaaacgggg    2580
ctcaggtaga agtggacatg caggaacggg tggcgtttgc ctgtaacatg gtcaatatgg    2640
gtccggggat agtggggatg ggtgggatta tttttcacaa tgtaagattt tatggagaca    2700 atttaacgg gatggttata atggcaaaca ctacggtgct tttgcatgga tgctactttt     2760 ttgggttaa taacacggtt ttggaagtgt ggggtcatag caaggttagg gggtgtactt     2820
tttacggatg ttggaaggcc attgcttcta gacctaagag tgaaatttct gtaaaaaagt    2880
gtttgtttga aagatgtaca ttgggagtct gtgtggaagg gaaaggacgg atatttaata    2940
atgtggcttc ggaaaatgga tgttttgctt tgattaaggg cttttgccgct ttaaagtata   3000 atatgatttg tggccagtct cctaccgaga gaacatacca gatgttaaca tgtgcagatg    3060
gaaatgtaca tttgttaaag acggtgcata ttactggtca tgcaaaaaag ccctggcctt    3120
tgtttgagca taatgtgctt actagatgtt ctgtgcattt gggtcctcgg cggggattt     3180 ttattccaca ccagtgtaat tttagccata caaatgtgtt ggtggaaacc gaagctgtaa    3240 cccgttttc gttaacgggt gtgtttgata tgtctgtggt gatttataaa atcctgcggt     3300
atgaggaaac aaaagctaga tgtcgctgct gtgagtgcgg tggaaagcat ttgagaaatc    3360
agcctgtgat tgtggatgtc actgaagaag tgaggatgga tcatatgcag cattcttgcg    3420
cccgggctga ttattctacg gatgaagata ccgaataggt gagtatgaga ggggcggggt    3480
tataaaagtc tataaaagct ggtctaaaac aaaaaaattt ttatgttgca gcgctcatca    3540
tgagtgggac aacgtctggt tccgtcactt tcgatggagg agtgtacagt ccttttctga    3600
catcgcgcct tccgaactgg gctggagtgc gtcagaatgt tatgggatca actgtggagg    3660
ggcatcctgt attaccttct aattctgctt ctatgcgcta cgctacaatc ggatcttctt    3720
cgctggacac cgccgccgcc gcagcagctt cagccgcagc gtccgccact cgtgttctgg    3780
cagctgattt tggcttgtat ggcaattca ctcccgctgc cgtaccccgc actgttcacg     3840
atgcacgctt actgactgtg ctgactaagt tggacaattt aacgcagcag ctggggagc     3900 tttctcgtcg ggtagctgag ttggccgaag aaagaacggt ttaaaaaata aaatgcaata    3960
aattcaagtt taaaaaattt tttattgtct gtttttttg tgataagctc gggaccacct     4020
ttctctgtca ttcaaaactt tgtgaatttt ttccattaca cgatagagat gggtttgaat    4080
gttaaggtac atgggcatga gtccatcttt ggggtggaga taagaccact gaagggcttc    4140
gtgttcgggg gtggtattat atattatcca gtcatatgag ttacgttggg cgtgatgttg    4200
aaagatgtct tcaacaaga gggtgatagc tactggaagg cctttagtgt aagtgttaat     4260
aaaccgatta agttgggagg ggtgcatgcg ggggacatg atatgcagtt tagactggat     4320
ttttaggttg gatatgtttc cgcctaggtc tctacggggg ttcatgttgt gcagtactac    4380
caggacggta tatcccgtac atttgggaaa cttatcgtga agcttagaag ggaaagcgtg    4440
```

-continued

```
gaaaaatttg gagatccctt tatgaccgcc taggttttcc atgcattcat ccataataat    4500
agctatgggg ccctggacgg cggctcgagc gaagacgttt ctgggatccg ttacatcata    4560
attatagtct tgggtgagct cgtcatagga cattttatga aaccgaggtt ttaaggtacc    4620
tgattgggga actagggtgc cttctggccc ggctctgaag tttccttcgc agatttgcat    4680
ctcccaggct ttaatttctg caggggggaat catatctacc tgtggagcaa taaaaaaaac    4740
tgtttcgggg gctggagaaa ttagctgggt ggacagcagg tttcgcagca attgggattt    4800
gccgctgccg gtggggccgt agattacggc aataaccggc tgtaagtggt agtttaggga    4860
ggtacagctt ccatcgtctg caagaagggg agcaacctcg ttcatcatgt cctgaacatg    4920
caaattttcc tgcactaatt ctcgcaacaa acgtggtcct ccgagcgaaa gcagttcctg    4980
aagggatgca aatttttta aaggttttag accttccgcc aaaggcatat tttgcaaaga    5040
ttgacataac agttgtaagc ggtcccagag ttctgtgacg tgttctacgg catctcgatc    5100
cagtagattt cctggtttct tgggttgggt tggctgttgc tgtaaggaac agccggtgg    5160 gcgtccagag gtgtcagcgt catgtccttc caggggcgga gggttctcgt gagtgtggtc    5220
tccgttacgg tgaaagggtg tgctccgggt tgggcgcttg ctagggtgcg cttcaaactc    5280
atccgactcg tggagaactg ttcgtttcct ccctggtagt cggcaaggta acatttcact    5340
aaaaggtcgt agctgaggga ctctgccgcg tgacccttgg ctcgaagttt tccttttggag    5400 acgtgtccgc agcggggaca gtacagacat tgcaaggcgt aaagttttgg ggctagaaaa    5460
actgattcgg gcgcataggc gtccgcgccg cacttttcac acccgtttc gcattcaacc    5520 agccaagtta gttcggggtg ggagggggtca aaaaccagcc tccctccgtt ttttttgatt    5580
cttttcctac cttttgtttc catgagttgg tgtcccaaat ctgtcacgaa aaggctgtca    5640
gtgtctccgt acacggattt cagggtcgc tcagagagag gtgtgccgcg atcctcttcg    5700
tagagaaact ctgaccattc tgagacgaaa gcacgagtcc aagccaacac aaaggatgcg    5760
atctgagaag gatagcggtc gttgtcaatt agggggtcgg tattttccaa cgtgtgaaga    5820
cacaggtctg tttcttccgc atccaaaaaa atgattggtt tgtaagtgta tgtcacgtgg    5880
cttggggggt cctgcggtgg gctataaaag gggggattcc accgttcctc gtcactttct    5940
tccggttcgc tgtccacgag cgctagctct ttgggtgagt aaacacgttg aaagaaggc    6000 aacacttccg cgctgaggtt gtcagtttct ataaagagg aggatttgat attaatgtgc    6060
ccacttgcta tcccttttaa ggttttatcg tcaagttggt cagaaaaaac agtttttta    6120 ttgtccagtt tggtagcgaa ggagccgtat agggcgttgg aaagcagttt tgcaatggat    6180
ctcagcgttt gattttgtc tttgtcggct ttttctttgg cggcgatgtt gagctgcaca    6240
tattccctgg ctacgcattt ccactgagga aaaacggtag tgccgttcatc tggaatcaac    6300 cgcactttcc agcctcggtt gtgcaaggtg accatgtcga tactggtagc cacttcccct    6360
cgcaaacgtt catttgtcca gcagaggcgc cccccctttc gtgagcaaaa aggggcagg    6420 atgtctagca agttttcgtc ggggggtcc gcgtctattg taaaaatgcc gggcaaaagc    6480
aagcggtcaa gtaggatat tttgaagag ctgtttagag cgtcctgcca gttttggcc    6540 gctagggctc tttcgaacgg gttaagggga ggaccccaag gcatgggatg agtaagagca    6600
gatgcgtaca ttccacagat gtcatacaca tacaggggtt cggtgagtac tccgagatag    6660
gtgggatagc atcttcctcc ccggatgctg cttcgcacgt aatcgtacag ttcgtgggag    6720
ggagcaagga agtaggccc caagtttgtt ttctgtggtc gctgggcggt gtagagaatt    6780
tggcgaaata ttgcgtgaga attagaagag atggtgggac gttggaagac attgaagcag    6840
```

```
ctgttgctgt aaccaacggt ttcgcggatg aactgtgcgt aggaagaaaa aagtttgtca    6900
acaagcgcgg ctgtgacgat gacgtccagc gcgcaatatt ctaaggtttc ttcgatgagg    6960
ttgtaatgcg gtttgttttt tgttttccac agttcgcggt tgaggaggta ctcggcttcg    7020
tctttccagt aatttcggag cggaaacccg tcagcggttg cttggtaaga acccagcatg    7080
taaaactcat tgactgctct gtagggacag catccttttt ccactggaag ggcgtacgct    7140
tgagctgcct ttcttaaaga tgtgtgagtt aattgaaagg tgtctctaac catgactttc    7200
aaaaattggt ttttaaaatc tgagtcgtca cagtttcctt gttcccacag cgtaaaatct    7260
tttcgttgtt tgtattttgg gttgggcaga gataaggtaa cgtcgttaaa aaggattttt    7320
cctgcccgag ggataaaatt tcgagagatt ttgaatggag ccggcacgtc ggtgcggttg    7380
tcaatgactt gcgcggccaa tactatttcg tcaaaaccat tgatgttgtg accgacgata    7440
tacaactcta aaaactgggg ggagcctcta agttccgggg ccgcgaccag ttggtcatat    7500
gtaagttcct tggggtcaca aaggcctaag gtttgttgac accagaaggt tagatgaggg    7560
ttttcgtctg cgaaagtgtt ccacatgtgg tcacagagaa ccgattgcag tttgtctctg    7620
aagcagcgga actgttttcc gataaccatt ttctctgggg taattaagta aaaggtagtg    7680
gggtctgcgt gccacctgtt ccactgtagc tcgacggcca aattgactgc tgttttaacc    7740
agctgggctt ggcctgtgaa tttcattacc aacatgaaag gaaccagttg cttaccaaag    7800
gaacccatcc aggtgtaggt ttctacatcg taggtgacga acagtctttg aactgccgga    7860
tgcgagccaa tgggaaaaaa ctgaatttga cgccaccatt gtgaagattg aacggctacg    7920
tgatggaagt agaagtccct tcgacgcgcg gtgcactggt gttgatgctt gtaaaatcgg    7980
gcacagtatt cgcatctctg catgggtgtt acgtcttgaa tgagataggc tttgcgtccg    8040
cgtatcaaga aacggagagg aaaggggagt ggcacgcggg atgggctgtt gggctggggc    8100
tgtttgcttt cgtctgttgt gctttgattt tggccgtcgg ttgggaggac ggccaccttg    8160
acagcgcccc gggaaatgca agtccaaatt tcggcgaagg aaggcctcag acgagcaacg    8220
agtcgttgga cgtcgttcgt tccgcaagtg tccggcagtg tgcagaggtc agctggaaat    8280
cggagtaaat gaatttcaaa gaggcgttgt agggcgggaa gcaggtgaag gtggtatttg    8340
agttctacag gactgtggtc tcgcgtgtca atagcgtgta tcaagccgtg agcgcgagaa    8400
gcaaccacgg ttccccgtaa actttttttc agtgtcggcg acggggtcgg gcgccggggg    8460
gcagggagg ctcggcgccg gcgggcagta ctgggagatc tacgtcggcg tgagactctg    8520
gcaacggtag gtgctgggac ctcagccggc tggcatgagc caccactcgg cgattcatgt    8580
tctgtatgcg ttgacgctgt gtaaacacca ctggtccggt tactttgaac ctgaaagaga    8640
gttcgacaga gtcaatgtct gcatcattga tggcggcctg gcgaagaatt tcgtgaacat    8700
cgccggagtt gtcctggaaa gcaatttcgg tcataagttg atcaatttct tcctcttgga    8760
gctcgccccg tcctgctcgt tctaccgtcg cagccaagtc gttagaaatg cgtcctatga    8820
gctgcgaaaa agcgccgaga ccgttttcgt tccacacgcg gctgtagact acggccccgt    8880
cgtcgtcgcg ggcccgcatg actacctgcg ccagattgag ttcgacgtgt cgactgaaaa    8940
ccggatagtt cctcagacgt tgaaaaagat agttaagggt ggtggcaatg tgctcggtaa    9000
caaagaaata catgatccat ctgcgtaagg tggactcgtt aatgtcgccc acggcttcca    9060
ggcgctccat ggcttcgtaa aagtcaatgg caaaattgaa gaactgggag tttcgagcag    9120
atactgtgag ttcttcttcc aagaggcgaa taaggtcggc cacggtggct ctcacttctt    9180
cctcaaacgt acgcggtggc acctcttctt cttcctcggc ttccattacc ggagcctcaa    9240
```

```
cttccacagg aactcgtctt cgacgtctgc gaatgggcag acgatctaca aatctctcta   9300
tcatttcgcc tctgcgtcga cgcattgttt ccgtcaccgc gcggccatcc tctcgcgggc   9360
gcagctcgaa tacgcctcct cgtaggccgc ttccttgaag cagattagct tgtctggggg   9420
tatttggcaa cgatatggcg ctgacaatac attttattaa tgtctgcaca gataacccgc   9480
gcagagttct aagcatcgtt agatccacgg gatcagcaaa gcgttgcaga aaggcgtcga   9540
tccagtcaca gtcgcaaggt aagctaagaa ccgcttcggg gggcagttcc gggcttacgg   9600
cgctgctaat gatgaaatta aaaaaggcgg actttaaacg gcgaatggtg gagaggagca   9660
caacgtcttt gggtccagct tgctgaatgc gcaaacggtc ggccatgccc caagcttctc   9720
cctggcaccg tctgagatcc ttgtagtaat cttgcatgag agtttcaacc gacacctctc   9780
ggtcgtccat tcgggtggcc ccgaatcccc tgaagggttc cagtaaggca agatcggcta   9840
ccacacgttc cataagaatg gcttgttgta tttgcgtgag ggtgttttga aagtcgtcca   9900
ggtcaacaaa gcggtgatag gctccggtgt tgatggtgta agtgcagttg gccatgactg   9960
accagttgac ggtttggtga cccggctgca gggtttcccg atattttaga cgggaatagg  10020
cacgcgtttc aaacacgtag tcgttgcacg tcctaaccag gtactggtaa cccacaagaa  10080
gatgaggagg gggcagacga aagagcggcc atccccgggt ggcaggggcg ttgggcgaca  10140
ggtcttctaa cataagacga tggtatccgt agaggtatcg cgacatccaa gatatacccg  10200
ctacggtggt agctgccctc gtaaactcct gcaccctatt ccaaatgttg cgtagcggta  10260
aaaagaagtc tacggtagga acgctttgtc ccgtaagccg ggcgcagtct tgcacgctct  10320
ggagtggaag aagagaaaaa acagtacgcg taaacggctc ttctccgtgg tctagtggaa  10380
aatttgcaat ggtatgttgg cggagctcac gggttcgaaa cccgccggct ctgccagcat  10440
cggggtgatt ggtcgtcacg tctcgaacct agccggcgaa ccctagatac ggaggagagt  10500
cttttgtttt cagatgcatc cggtgttacg acaaatgcga ccctcaaaca gcggtcccgc  10560
gaccaccgct gcgggagcag tgtgtcaggc cggcgcagga aatccgttgg aggaagtgct  10620
ggacatagaa gagggcgagg gcttggcgag actgggcgcg cactcgcctg agaggcaccc  10680
tcgtgttcag ctgaaaaagg attccagtga agcttatatt ccaccccgta acttatttag  10740
agaacgaagc ggggaggagg cggaagaaat gagggactcg cggtttagag cgggtagaga  10800
gttaaaaaaa gggttggaca gggagcgcct tttgcgaccg gaggattttg aagcccgaga  10860
cagaacgggc gtcagcgctg ccagggcaca cgtggctgcg gccgacttag tgacggctta  10920
cgaacaaacc gtgaaagaag aaatgaactt tcaaaaaagc tttaataacc acgtgcgaac  10980
tttgatagca agggaggagg tggcaatagg actaatgcat cttttgggatt ttttggaggc  11040 gtatgttcag aatcccacca gcaagccgct gaccgctcaa ctttctcttaa ttgtgcaaca  11100 cagcagagac aacgagacat ttagagatgc gcttttaaac atagcagaac cagaaggacg  11160
gtggttgcta gacttgatta acattcttca gagcatagtg gtacaggaac gtagcctgag  11220
tttggccgac aaggttgcgg ccattaacta ctccatgtta agtttgggaa agttttacgc  11280
gcgtaaaatt tacaagaccc cttacgtgcc cattgacaaa gaagtaaaaa ttgatagttt  11340
ttacatgaga atggccttga aagtgctaac cctcagcgac gacttgggca tctaccggaa  11400
cgatcgcatt cacaaggcgg tcagcgccag ccgccgtcgg gagttgagtg acagagaatt  11460
gatgtacagt ttgcagcggg cgctgacggg aactggacac ggacaggatg aaaatctctt  11520
tgacgctggg gcagatttaa agtggcaacc cagtagaagg gcgtggcagg cagccggtac  11580
ctatttagaa agcatagagg aggacgaaga cgaagacccg gagaacgagc ccattgacta  11640
```

```
gccaattttt ttagatgcaa aggcccgcgg cgatggcttc caccgaaacc gaacctatgg    11700
accccgttgt tcgggcggct ctccaaagtc agccctcggg tgtggctccc tcggacgatt    11760
ggtctgctgc tatggaccga ataatggctt taactgcccg aaattctgaa gcgtttcggc    11820
agcaacccca agcgaacagg ttttcggcaa ttttggaagc cgtggtacct tctcgtccta    11880
atcctacgca tgagaaagta ctggccatcg taaacgcttt agctgaaaac cgagctattc    11940
gccctgatga ggcaggccag atatacaacg ctctgctgga gagagtggcc agatacaaca    12000
gcaccaatgt tcagagcaac ctagaccgtt tggtgaccga cgttagggag gcggttgccc    12060
aaagggagag gttccacaaa gacgccaatc tggggtccat ggtggctttg aatgcctttc    12120
tcagttcact tccagctaac gttccgcgag gtcaggagga ctacactaac tttatcagcg    12180
ccctccgtct catggtagcc gaggtgcctc aaagcgaggt ttacatgtcc ggacccagtt    12240
actattttca aacttccagg cagggcttac aaaccgtaaa tttgtcccaa gctttcaaaa    12300
acttggaagg tctgtgggc gtaaaagctc cattaggcga ccgggctacc gtttccagtc    12360
tgttgacgcc taacacccgg ctgttgctcc tgctaatcgc tccgtttact gacagcggga    12420
gcatttcgcg ggactcgtat ttgggtcatt taataacttt gtaccgagaa gccattgggc    12480
agtctcgcgt ggacgaacac acgtatcagg aaattacaga tgttagtcgc gccatgggtc    12540
aggaggacac ttctagtttg caagctactc tgaactactt gcttaccaat cgtcgtcaga    12600 gaatccccccc acagttttca ctgtctccag aggaggagag aatccttaga tacgttcagc    12660
agtctgtcag tttgtattta atgagggaag gggacggccc cagtgctgct ctggacttaa    12720
ccgcacgaaa tatggaaccc ggtctgtact ccactaaccg ggctttcatt aaccgtctga    12780
tggattatct gcaccgcgcg gcggcgctta atcccgaata cttaacaac gccgtgctga    12840 atccgcactg gctgccgcct ccgggctttt acacgggaga gtttgacttg cctgaagcaa    12900
atgacggctt tatttgggac gacgacacta gtgttttttc gcccatgcaa aagaaagaag    12960
gaggagacgc ccagagtcaa cgggtttcct tagccagcat gggcgcctct gtagcgagtc    13020
ccctgcctag tttttcgtcg gcttccagcg cggccgacg cgttaatagg ccccggctgt    13080
ctggggaaac ggattattta aatgatcctc tcatgcgtcc cgctcgggca aaaattttc    13140 ccaacaatgg gatcgagagt ttggtagaca aaatgtccag atggaaaact tacgcgcagg    13200
agcagaggga gtgggaggaa cagcaaccgc gaccccctaat tcccccccaca cgtggtaacc    13260 gtcgccggcg tcaggatatg gggccctatc gcgtacccgt ggatcccgaa gactcggccg    13320
acgacagcag cgttctagat ctgggggaa gtggcaaccc ttttgcgcat ttacgcccgc    13380
agggcagaat aggcaagtgg taactaaata aaatacttac caaggccata gcgtggtgtg    13440
cgtcctgttt tttctagcgc gatgctccga cgtggaatac ccccggtggc cgttgcggaa    13500
ggtccaccgc cgtcttatga gagcgtgatg gcagcggcgg cgttgcaggg tcctttggta    13560
gctccttatg tgccgccgcg gtacctaggg cccacagagg gaagaaacag catccgttac    13620
tcggaattgg ctcctctta cgacaccacg cgtctttatt tggtggacaa caaatcggcc    13680
gatattgctt ctcttaacta tcagaacgat cacagtaatt ttctgaccac cgtggttcag    13740
aataacgatt ataccccgc cgaagccgga acccaaacga taaactttga cgaccgttcc    13800
cgatggggag gggaaatgaa gactattttg cacaccaaca tgcccaacat taacgcctat    13860
atgtttacaa ataagttcag ggctaaatta atgacggccc atgaaactga caaagatccc    13920
gtgtacgagt gggtagattt ggttctccct gagggaaact tttctgaaac tatgactata    13980
gatttgatga ataacgctat agtggatcac tacttactag taggacgtca aaatggagtg    14040
```

```
aaggaaagcg agataggagt gaaatttgac accagaaact ttcggctcgg ttgggatccc    14100
gaaacccagc tggtaatgcc cggagtgtac actaacgagg cgttccaccc cgatattgtt    14160
ttgcttccgg gctgcggggt ggactttacc aacagcaggc tcaacaatct tctgggcatt    14220
cgcaagcgcc agccgtttca ggaaggtttt caaatcttgt acgaagacct cgtcggcgga    14280
aatatccccg ccctcctaga cgtcaccgct tatgaaaaca gcacgccggg ccaaccgccc    14340
acaattcagc ccgttacgga ggacgctaaa aaccgaagct ataacgtgtt acctggaacc    14400
aacaataccg cttatcggag ctggtacctc gcttataatt acggagacga cacgggtata    14460
cgttcctcca ctttactgac agcgcccgat gtcacctgtg ggtcggaaca gatttactgg    14520
tcaatgcctg atatgatgca agacccggtg accttta gga gttcccaaca gaccagcaac    14580
ctgcccgtcg tgggcacaga gttgcttcct atgtacgcta aaagttttta caatgatcaa    14640
gcagtttatt ctcagcttat tcgtcagtct accgctctta cccacgtgtt taatcgtttt    14700
cccgaaaatc agatactggt gcgaccgccc gcccctacta tcaccaccgt tagtgaaaac    14760
gttcccgctc ttacagacca cggaacgctg ccgctgcaaa acagcatccg gggagttcag    14820
cgagtgacca tcactgacgc caggcgccgt acctgtcctt acgtgtacaa agctttgggt    14880
gtagtggctc ccaaggtttt atcaagtcgc acttttta ag acaatgtcca tccttatctc    14940
acctagcaac aataccggtt ggggtcttgg cgtgaataaa atgtacggag gagccaaaca    15000
caggtcaacc cagcacccgg tgcgggtgcg tggtcattac agggcaccct ggggcgcata    15060
caagcgcaac agacgggtag ccgaacgcac taccgtggac gacgtaattg actccgtggt    15120
agcggacgca cgcaactacg tgcccccagc cgttcccgct gccgctgcat ccacagtgga    15180
tgcagttata gatagcgtgg tggcagatgc aagagcctac gctcgtcaga agcgcagaca    15240
acgacgagcc cgtcgttcct tggctcgacc taccgcggcc atgcgcgccg cccgaaacct    15300
gcttcgaagg gcaaggcgca ccagcacacg cgccatggcg aggcagatta gggccggtcg    15360
gaccagacga agggcggcgc aacaggccgc ggcggccata gccagccttg cggcgcccag    15420
aagaggcaac gtttattggg tccgtgacgc cagcggagtt agagtgcccg ttcgtactcg    15480
tcctgcgcgc gtgtgattaa aagaaaaaat aaaaaccgca tccaacgctt aaaagtgaag    15540
actgagtgtc ctgttatata ttcagcgtcg gcgccatgac caaacgcaaa ttcaaggagg    15600
agctgcttca ggccattgca cctgaaatct atgccccgct aacggatccc gatgttaaac    15660
ccgacgtgaa gcctcgccgt ctaaaaaggg ttaagaagca ggagacaaaa aaagaggaag    15720
cattagacac cgagggggtg gagtttgtgc gttcttttgc tccccgaaga cgcgtgcaat    15780
ggaaaggcag acgcgtacgc cgccttctta ggccggggac cgcagtggtt tttaccccgg    15840
gagagcgctc ctcccgcact acaagcgttc gtacgacga ggtctacgcg gatgaggata    15900 tttttggaaca ggccctggag cagagcggag agttcgccta cggcaaaaga gcccgaaatg    15960
aagttgctct tcccctggac gaaagcaatc ccaccccccag tttaaaaccg gtgactctgc    16020
agcaggttct tcccgtccaa agcacgggag aaagcaaaag gggaattaaa agagaggcag    16080
tggagctgca acccaccatg caattaatgg tcccaaaacg tcaaaagttg gaggatgtcc    16140
tggatttaat gacggtggac ccttcagtac aacccgacgt aaaaattagg cccattaaag    16200
aagtggctcc cggtttggga gtgcaaacgg tagacattca aattcccgta gaaagcatgg    16260
atgtggaaaa gccgaagccg accgccgtgg acatggcagt gcaaaccgac ccctgggccg    16320
gtgctcccgt tagagccgca agcgccattc gcaaccgccg ccgctacggt cccgccagtt    16380
cgctcatgcc agattacgct ttgcatcctt ccatcattcc cacgcctggt tatcggggac    16440
```

```
aggtctttcg cagacgatac tccgccccag ctagacgctc tactaggcgt agacgcagaa   16500
ggcggacgac tctccccgtc agagtaaggc gcgtaaccac gcgtcgagga cggacattaa   16560
ctctccccac agtccgttac catcccacga ttgtttaaca cgtacccacc tactttacag   16620
atcatggccc taacctgtcg tctccgcatt cccgttcccg gttaccgagg aagacgccgc   16680
cacgggaagg gcttcagggg tagcggttta acccgacatc ggcgtcggcg ggccgtgcgc   16740
ggacgcatga aggggggcat tctccctgct ttgattccta ttatagccgc ggcaatcggc   16800
gctattccgg gaattgcctc agtggccgta caagcctccc aaagacaata attaaaccca   16860
ggcgccgctg tctttcttac gcagtgtatt atggaagacg tgaattttc gtccctggcc    16920 ccgcgacatg gtacccggcc ctacctgggc acttggaacg atatcggcac cagtcagctg   16980
aacgggggcg ccttcaactg gagtagcatc tggagcgggt tgaaaattt tggttcaacc    17040 ataaagtctt acggaaacag gcttggaac agcagcacgg gtcagctgct gcgcgataag    17100
ctcaaagacc agaattttca acagaaggtg gtagacggct tggcggccgg cattaatggg   17160
gtcgtagaca ttgctaacca ggcggttcag cgcgagataa acaaccgtct agatccgcgt   17220
ccagtagagg aggagctacc cgcttttagaa aggcaacctc agggcgaaaa gcgtccgcgg   17280
cccgatttgg aagaaacgct tgtaacggaa gaacctcctt cttacgagga agccgtaaag   17340
ggagcgccct cggtggctct taaaccggtc acctatccac tcacaaaacc cataatgagc   17400
atggctacgc cggttgggga cgctccaatg gtagtagacc ttcctccacc acccgcaggg   17460
atgaccactc caacggtccc cgttcccatt gctccgcccg tttcgcgtcc cgccatccgc   17520
ccggttgccg tggcaacacc ccgttatacg cgcacaaaca actggcaaaa cacactgaac   17580
agcatcgtgg gcctgggagt caaaactctg aaacgccgca gatgctacta ttaaacgctt   17640
tttaaccctc cgtcttgtgt atacgcctgt tgttgtcagt aaaagaagag ccgcggattc   17700
gccgccgtcc tcgcttgcaa gatgccacc ccatcgatga tgccgcagtg gtcgtacatg    17760
cacattgccg ggcaggatgc ctcggagtac ctcagtcccg gcttggttca gtttgctcga   17820
gccaccgata cctacttcac actgggaaac aagtttagaa atcccaccgt ggccccacc    17880 cacgacgtca ctactgatcg gtcccagcgt cttactttgc gatttgtgcc ggtagacagg   17940
gaagacactg cctatgctta caaagcccga ttcaccctgt ccgtgggtga taacagagtg   18000
ctggacatgg ccagtaccta ctttgatata cggggagtaa tagaccgagg tcccagtttc   18060
aagccgtatt ccggtaccgc ttataatgct ttggctccaa aaggggcgcc taacaacagt   18120
cagtggcaca ccgttaacga ggacaaccag aatttcctga tgcacacata tgcccaggcc   18180
ccatttgaga gcgaatttgt ggctaacaac ggcaacattg gtattcaagt gggagtgagt   18240
gacaccaaca ctcccatttt ggcggatccg acatatcagc cggaaccaca ggacggagaa   18300
ccgcagtggc agagtctaaa agcgcaagag aagctagaac atgcagggag agcgctgaag   18360
tataccactc ccatgaaacc ctgctacggg tcctacgctc gccccaccaa cgcgcagggc   18420
ggacaaggga taattgacga acaaactgga gaaacagatg cgacggaaat tacccaaaac   18480
tactttgcgc tgtcaacggc gaccacggac ttcacgccaa aagtggtgct gtacacgaa    18540 gatgtttact tgcaaacccc agatactcat ttggtgtaca ctccgtcggc cacggaaggc   18600
agcactcagg atatgctggg ccagcaagcc gccccgaatc gccctaacta cattgggttc   18660
agggacaact tcattgggct aatgtactac aacagcaccg gaaacatggg agtgttggcg   18720
ggccaggcct cgcagctgaa cgcggtggta gacttgcaag accgaaatac cgaactatcc   18780
taccagctca tgctggatgc tctgagcgat cgcacaagat acttctccat gtggaatcag   18840
```

```
gcggtagaca gttacgaccc tgatgtgcga attatagaga atcacggggt ggaggatgag    18900
ctccctacgt actgttttcc actttccgga gtcggcatta ctcaagagta tcagggagtg    18960
gaacccacca atcccgccgc tgccgacatt acgtggaaag aggacgccac ggtctttgat    19020
cctaattaca ttgctaccgg caacatcaac gcctacgaaa ttaacttgca ggccagcctc    19080
tggcgcagct ttctttactc caacgtagct ctctacctac ccgacaagta caagtacacc    19140
cctgctaacg tcacactccc cacaaacact aacacctaca agtacatgaa cggccgcgtg    19200
acctctccca gcttagtaga cattttgtg aatgttggag cccggtggtc gccggaccct    19260
atggataatg ttaatccatt caaccatcac agaaatgccg gcctgcgtta ccgctctcag    19320
cttttgggta acggacgcat tgttcccttc cacattcaag taccgcagaa gttttcgcc    19380
attaagaacc ttttgctgtt gcctggttct tacacctacg agtggtcctt cagaaaggac    19440
gttaatatga ttctccagag cacgcttggt aacgatctgc gaacagacgg agcggccatt    19500
aggatcgaaa gcgtaaacct gtacgcgaac tttttttccca tggcccacaa cacagcctcc    19560
actttagagg ccatgctgcg caacgacacc aatgatcagt ccttcaacga ctacctctcc    19620
gccgccaaca tgctgtaccc catcccagcc aacgcaacca atgttcccat ttctattcct    19680
tctcgcaatt gggccgcttt cagaggctgg agcttcaccc gtcttaaagc caaggaaacc    19740
cctgcccttg gatctggctt tgatccctac tttgtttact caggctccat tccttacctc    19800
gacggcacct tctatctcaa ccacactttt aaacgggtgt ctattatgtt cgattcctcg    19860
gtgagctggc caggaaacga ccgactcctc accctaatg agtttgaagt taaacgggta    19920
gtggacggag aaggctacac tgttgcgcag agcaacatga ccaaagactg gttcctaatc    19980
cagatgctta gccactacaa catcggctat caaggcttct acattcccga gggctacaaa    20040
gatcgcatgt actccttctt ccgcaacttc caacccatga caagacaggc cgtggatccc    20100
gtaaactaca ctaattataa ggaaatcacg gtggctcacc agcacaacaa ctcagggttt    20160
gtgggattca tgggccccac catgcgcgag ggtcatccct acccagcaaa ctaccctat    20220
ccgctcattg agacagtgc ggtgcctacc gttacccaga aaagttttt gtgcgatcgt    20280
accatgtggc gcattccttt ctccagcaac tttatgtcta tgggcgctct taccgatctg    20340
ggtcaaaata tgctttacgc aaattccgcc cacgccctcg acatgacctt tgaagtggat    20400
ccaatggacg aacccacact actctatgtt ctatttgaag ttttcgacgt ggtccgtgtt    20460
caccagcctc accggggcat tatcgaagcc gtgtatttgc gtactccatt ctccgccgga    20520
aacgccacta cataagcaac atggggtcca gcgaagaaga actcaaagcc ataataagag    20580
atttacggtg tgcgccatat ttttttgggaa cctttgacaa acgttttccc ggatttgtgt    20640
cgccgcacaa acttgcttgt gccattgtaa atacggccgg aagagaaacg gggggagttc    20700
actggctggc ttttggatgg aatccgaaaa accgaacttg ctacctgttt gatccgtttg    20760
gcttttcgga tgaaaacta aaacaaattt atcaatttga atacgaaaac ttgctaaagc    20820
gaagcgctat cgcctctacc ccggatcgat gcgtgactct ggtaaaatcc acccaaactg    20880
ttcagggacc taactcggca gcttgtggcc tgttcgcctg tatgttcctg catgcttttg    20940
taaactggcc caatagcccc atggaaaata accccactat ggacctgata gtcggtgtgc    21000
ctaattacat gttaaaaagc ccccaggttc agggaacgct ttttaaaaat caacaagcgc    21060
tgtaccgttt tttagccacc cactcccctt actttagaca tcatcagcag caaatcgaaa    21120
aggccacggc ttttaataaa caaactgaat ccaaaaatta ataataaatt tttatgcttt    21180
atttgtactc cgtcgtattt tttttttcaa aattcaaacg ggttcatttc aaagtcaaca    21240
```

```
tgggcagcgg gaagagtgag gttacgatat tggtacttgg gatgccattt aaattcggga   21300
accaccattt tgggaagaac ggtatcggga agatgatcct gccaaaactg ccttacaagt   21360
tgcaacgctc caattacgtc gggagcagaa atcttaaagt cgcagtttgc ctggttgttt   21420
gctttgctgt tacggtgtag agcgttggcg cactgaaaca ccagaacgct cgggttgttt   21480
acactggcca acatggcgcg gtcgtgataa ccgaaatcca ctaagtcttc caagtgaata   21540
ttctcaacat ttaacgcaaa aggggtaatt ttgcaagttt gacgtcctcc acgggacatc   21600
tcgggtcgcg taaaacagtt acaacgaatg ggcatgagaa gatgcttgga tcccttcacc   21660
atgtgagggt agcaagcttg catgaaagcg gcaatttgac gaaaagcaat ttgcgccttc   21720
gtcccctcag aatagaacat accgcaggat ttattagaaa agttgttggg agagcacccc   21780
gcatcaaaca tgcaacaacg ggcatcctca tttcttacct gaactacgct acgaccccag   21840
cggttctgaa caattttggc cttggcgggg gtttccttta gagctctttg cccattttcg   21900
ctagttacat ccatttctat gatctgctcc ttcactatca tggtcaaacc gtgtaagcat   21960
ttaagctcac cctccacatc cgtacactga tgctcccaag ctacgcatcc ggtaggttcc   22020
cacaatttgg aatctacacc ggcgtacacc tgcacgtaag ccattaggaa gcggcccatc   22080
agagaaatga aacttttatg agaagtaaaa gtcaaggtgt tgtgcttata ctcctcattc   22140
atccaagcct ggcatatttt gcggtacacc tctccttgct cgggcaaaaa tttaaacgag   22200
gaccttagct ccttgtctac cttgtacctt tccattaaca taaccataaa ttccatgccc   22260
ttttcccaag cagaaaccaa cgggttagag gcagggttaa caacggttga actggttccc   22320
tccttttgtt gacgggctgc ggacattatg gggtgatttt cgtcgaattt ttcgaaggct   22380
ttgcttccgt ccgccttccg tactattttt acaggagggt agctgaaccc cacttccagc   22440
aactctccca cctcttcgtc gctgtcggcc accacttctg gtgaaggcgg gagaggcagt   22500
gacttccgcg cttttctttt tgggggcaca gctggaactt tttcgggtgt tacttcgcga   22560
cggtcctgat tgctggccat tgttttttcc taggcaaaaa acatggaatt ggaaccagcg   22620
gccgaaagca acaacttaac ctccccccat ttttacgaga acaaggacgc cctcaccgag   22680
gctacggggt ccgcagtgga acaggacgtg ggctacgcgt ctccgccaga aacggcggag   22740
gaggaaaagg atgacaaaaa cttatcgagc ccacaaaaag acaagcaaca agatgataag   22800
acacaggaaa acgaggagga cgttagcttc catgacgatt acctaggcaa aggagaggac   22860
gttttactaa aacacattcg aaggcaaagc gccattgtgg aaaacgccat ttccgaaaaa   22920
accgaaatac cggtgtcggt gtacgactta agcctggcgt atgaacagag cctcttttct   22980
cctcgtgttc cacccaaaag acaacccaac ggcacctgcg agcccaaccc gaggctaaac   23040
ttctacccgg catttgccgt tcccgaagta ttagccacct atcatatttt ctttaaaaac   23100
cacaaaatcc ctgtttcctg ccgcgctaac agaagcgaag ccgatgccca acttttgctg   23160
ggtccaggtg cccgcatacc tgattttgct tccttagaag aagtgccgaa atattcgag   23220 ggcttgggag acgaaaaacg tgctgcaaac gctctgcaag aaaacacaga agtttcagc   23280 gcgctggtag agctcgcaaa tgacaacgcc cgtctagccg tgctcaaaag aagcgtagaa   23340
gtcacccact ttgcctaccc cgctgtcaac ttaccgccta aggttatgaa cacggtcatg   23400
gactgcttac tagtaaaaag ggcaaaacct ctggggggaag gggaacagga ggaagaagac   23460
tcagacgagg gcaaacccgc cgttaccgac gaagaactct cacgctggtt gcgcacaaca   23520
gacccagcag agttagaaaa tcgtagaaaa cttatgactg cggtcatact ggtaaccgcg   23580
gagctggagt gcctcagtag attttttacc gatacggaaa ccataaggaa agttgaggaa   23640
```

```
accttgcatt acaccttccg tcacggttac gtgaaacaag cctgcaagat ctctaacgta   23700
gaactcagca acctggtttc ttacttaggc attttgcatg aaaacagact gggtcaaaac   23760
gttctccacg ccacgctaaa gggagaagcg agaagagact atattaggga ctgcgtctac   23820
ctgtttttgt gttttacgtg gcagtccgca atggggtgtct ggcaacaatg cctggaagat   23880
gacaatttgc gagagttgca aaaatactg aatagagaac aagggaccct gtggacgggt   23940
tttgatgaaa ggacggtagc caaggaccta gcgaacatta tttttcctag cagactagta   24000
agaactttgc aaaatggctt gccagacttt atgagccaaa gcatgataca gaacttccgc   24060
tccttcatct tggaacgctc aggcattctg ccttccatga gctgcgcttt gccttcagat   24120
tttatccctt tgaccttcag ggaatgccct cctccactct ggagccactg ctacttattc   24180
caacttgcaa acttttttgc attccattct gacgtcgtgg ccgacgttac cggagaggga   24240
ctgatggaat gtcactgtcg gtgtaatctg tgcacccccc accgttccct ggtttgcaac   24300
accgctttgc taaacgaaac ccaggtaata ggtaccttttg aaatccaggg accttcagaa   24360
tccaacaaag gagccgcggg gttaaaacta actccgggat tgtggacttc cgcctaccta   24420
cgcaaatttg taccggtgga ttaccacgcc acgaaaattc gattctacga agaccaatca   24480
ggaccccca aagcagagct cagcgcttgc gtcattactc aaagcagcat tgtggcccaa   24540
ttgcaagcca tcaacgaagc ccgccgaaac ttccttttga aaaaggaaa gggggtatac   24600
ttggacccc aaacgggcga agaattaaac accaccccct ccccagttgc aggtgtctcc   24660
cacaatgcca ccaaagaaga ggtccgccgc cctcccgctc tccaaagcag tcacagcaaa   24720
gcgacccaaa cagaggaaag cccaggagac cgaggaacca tggagcgagg aggaggactg   24780
ggagagtcag ggagaggaag acatggaaga ggaatgggac agcctagcca gcgacgaggg   24840
agaggcagag gcagagacag aggaagcatc cgtcgcaaaa ccctcactgg cgaaacgagt   24900
ttcaaacgtt actacgacct cagatcagcg cacagtcagt cgtagatggg acagtaccaa   24960
cgccgccccc gccggtaaga ccctttcgtt ggcaaaaccc cgacagggat accgctcctg   25020
gcgagcgcat aagaacgcca ttataaactg ccttgaaaat tgcggaggca acatttcttt   25080
cacccgtcgg tttatgctct ttcgaaacgg aattgccatt cccagaaacg tcttacatta   25140
ctatcgtcat tcttacagcc cctcgaaaac cgtacctctc ggcagcggcg gccgcggcgg   25200
acactaaaaa gaggttacct aagcagaaca aaaagcaagt gaaagagccc ccatctacca   25260
aagaacttag gaaccgaatt tttcctactc tgtatgccat tttccagcaa agccgcggac   25320
aagaaccaga gcttaaaata aaaaaccgct ctctccgttc acttacccgc agttgtctat   25380
atcacaaaaa cgaagaacag ttgcaacgca cgttggacga cgcagaagct ctgttcaaca   25440
agtactgcgc agcaactctt aaagaataaa aaaaatcgcg ccaaaaattc aaaaaagatt   25500
gtgtcatctt ggctaacggc ccgcaatgag caaagaaatt ccaacccctt acatgtggag   25560
ctaccagccc cagatgggat tggccgcagg tgcggcccaa gattactcaa ccaaaatgaa   25620
ctggttaagc gccggccctc acatgattgc tcaagttaat ggaattcggg cccaccgcaa   25680
tcaactgtta ctggaacagg ctgctcttac caccacaccc agaaatcaat taaaccctcc   25740
cagttggcct gcgtcactgg tgtaccagga aacaccggct ccgacaaccg tactacttcc   25800
tcgtgacgcc caggccgaag tcctcatgac taactcaggt gcacagctgg ccggcggggc   25860
gtgccggtat cggtccaaag gccccactgg gctctccgcc cctttgggta taaaaagggt   25920
gctcatccgt ggcagaggca cccagctcaa cgacgagaca gtgagctctt cgcttggtct   25980
acgaccagac ggagtgttcc agctcgcggg ctcgggccga tcctcctttca cgcctcgcca   26040
```

```
ggcttatttg actctgcaaa gttcttcatc tcaacctaga tctggtggca ttggaacgct    26100
tcagtttgtt gaagagttca cgccatcggt ctacttcaac cccttctccg gggcgccggg    26160
gctgtatccg gacgagttca ttccaaactt cgacgcggtg actgactccg tggacggcta    26220
cgactgatgt ccaatgagtt tgagtctcta gtagaccaag ctcgtatccg ccacctcgac    26280
cactgccgtc gccaccggtg cttcgtcaga gaacatctcc agaccgtcta ctttgagcac    26340
ccagaaagcc accccgacgg tccctgtcac ggtatttacg tgattgtgga cggatcctgc    26400
gacacccacc tcgttcgcta ctacagccaa cgccctctat tggtggaacg ccaaaccggc    26460
gtcactaaga ttaccctcac ctgcatctgc tcgcaacccg gcttacatgc agacctctgc    26520
tgccatctgt gtgctcgctt taatcagctt cgttagctgc gttcagcctg cctccgggca    26580
gattgacgtc tgccaagcgg ctaacgtgac tgttaccgac ctctcaaaac ccacaatcac    26640
cgttaagtgc ggcttctaca caaaccagt ttctacagtt ttctggtact tcaacaacac    26700
cctcttctcg tccttcaatc cgttttcact ccttatcagc aacatcaagc aacccttta    26760 ctactacacc accggcaaca gtcttcagct ctttgctccc tacagttctg gacgttacca    26820
ctgcgaagtc cttaagtgca ctcaacattt tttcattgga attaaacctg caactccaat    26880
caccactgcc gctaccacta ctacccctaa tactactgct gtcactactc ctcctcctgc    26940
tactgcatct tctactacaa ctcctccagc cgccgccacc acttcttctc ccagcgctcc    27000
caagagatcc atcagatcct tctcccacag ctttctgagt atcaacgtct cagatcccac    27060
tcaagtcctt cagtgccct gctccggcaa ctacactttc tggggcgtaa acggaactga    27120
ttgggccttt gttcagaaca tcacctttgt tacctttatt cagaaccaaa ctatcaactt    27180
caaccacaag ttcctcaaca cttctctgaa cctccgactt ccagttgttc ctggtaacta    27240
cagctgcgac actcaaagcc gtcagtgcca gcacgttttt accgttaccg ttatttaccc    27300
cactcccact actccggctc caccgaccac cgccaccgaa actaacaccc accaggcctt    27360
ttttgctccg agcgaagctc cagaaacagc ggttgcctcc actccttggt ggctatttgt    27420
tgtggttggc attgttgtgg tgattattgc aggtgcagtt acagccttt ttatttacaa    27480 gaagcaccca gaagtggtgg ttttctttca cagagttccc acctcagttt actaaggtaa    27540
gatgaaattt ttactgttta ccatccttt tagcctttgt ggctcttctc actcagtttt    27600
ttatcctcct ccaaattgct acgttacctc cagatgggat cccaactgcc acattcaaat    27660
cctgtgccct gacaacagca ccatttacta ctccaatacc tccgtggtcg gctctctcac    27720
actcaaccct gaggataacc cacccgacca ctatctcatt aatcacaccc tgtcaaatgg    27780
caaaactgcc ctttacaatt ttacttttcc catggccact ctgtgcacca tcactgaagc    27840
cacagattca ggctacgatt ttactgtttt gttttttactt ttaatggtgg ttgccctcat    27900
tctccttttg gcagcacttg cttgtctctt ttaccactac tgccgctggt ggcgtaaggg    27960
atcctacacc ttaccccacg accagcgcag tatccaccta gaaatttaac aaactttcy    28020 tttttttttt gcagtatgac tcttgctctt cttatctgca ctcttacagt gccagtcacc    28080
cttgccaccg tctcttttgc cacggctact catctcgaac cggaatgcct tccaccattc    28140
caagtttacc ttgtgttttc ttttctgtgc tgcacctgta ttgctagcct cattacttta    28200
ctgctggtat tttttcagtt tgtggactat ttcctagttc gcctgcgcta tcgtcaccac    28260
gcaccgcagt tccaaaatcc caacgttgct cgactcttag ctcttcaacc atgaaagctc    28320
ttctggtgct agcatttttta cccctcactc actgctgccg ttttacattc tccaagctgt    28380
ggaccatcag agactgttac ccctttgttc cagtccgtga agaaccatgg ctgtttacta    28440
```

```
tcctcatcgt cgctgcccct attgccttt ttgcagctat ttacctgaga aatatattac  28500 cttctcttg gaatacagat gatctacttg attatcccat tctcccccaa cccaacgtta  28560
ttcctttgca aaaccttctc cccaacctcc ctgaccttct ggatcaactt cccctaatc  28620 ctgatccacc ccgttccccc tctacctgca gttacttccg cttcaccaat gagtaacccc  28680
ctagaaattg acggactgcg gtccgaacaa caagccctca tggtacgtga gcgggccaga  28740
caacgggagc taaagcacca ggagctgtta gatctgcaaa acacccatca gtgcaagagg  28800
ggcattttct gcgcggtgaa gcaggcttct cttcgcttcg aaatgctgaa ccctccagac  28860
cacgagctcc aatacaccat tcagcaagag cgccaaaact gtgtgtttat ggtgggctct  28920
aaacccatca aaatcacaca agtagaggg gaggttaccg gggctctccg ttgttcttgc  28980
acccattccg aatgcatgta cacccttgtg aaaaccctct gcgggttaca tgatttaata  29040 cccttaatt aacagcaaaa ccaatcaaac ccaatcaaca cccaattata aaaatgaaca  29100
ataaacttac atgaattcag cagttaactt gtttgtggct tttgtgtcca atttaaccca  29160
tttaccctct tcccaactct gatatccaat acttcttcta ctagcaaact ttctccatac  29220
cctaaagggc atgtcaaatt taacaacttt gccactgcta tctattatat tcattttaga  29280
tgaagagagc cagagctgta acagaagact tcaaccccgt ataccttat gacacccta  29340 ccggtggaaa cgtcgcaccc tttgtaactc cgccttttgt gtcccctgat ggtctacaag  29400
aaagcccccc tggcacactc tccctaaaca tcaaatctcc cctcactatt acaaaccacc  29460
aactagacat taaattggga agtggactat cagtatcttc aaagggagaa ttagaagcca  29520
gttccaccac caccgtaact gcgcccctaa ccaatacaaa caacattata ggactttctt  29580
attctgatgg cctgacttta gaacagaatt ttctgaaagt aaatcttgga agcggtctca  29640
cgtttgataa ccaaagtata accctcaacc ccccaactct gtggacgggc ccggctgcag  29700
aaccaaacgc cactgtactc ccccaggca gcgcagacat tcctgattac aacgcatgca  29760
tcaccctgag tttaactaaa ataggacccc tggtaaatgg tttaattcc cttatagga  29820 tttcagcccc cctaactccc atagcggcag acgtgaactc ggtgaaggtt ccttacttt  29880 ttaatgacaa tggtcaactc atcgggccag actttgaaac tgacacttt ggatttaaag  29940 tgggtaacac tatagacaca acttccaccg ccagcagggt tcctttcatg cccaatgtca  30000
ctacttatcc tcataactcc acaggtcaag ctggagcagg gcattatatt attgtgccgg  30060
gaatggttaa cgccgactct tccaaacct gcaacttaat tgtgggactt aacacagcgg  30120
gatcttcggg attctccatt acattggagt ggacagggc ggctaattac aacctatccc  30180
ttggtacctc cacctttttt ttagttattt atcacaagac caaaattaaa gtgcataaaa  30240
agttttattt gcgttgattc atgttacagg gggacgggca tcgtacacct tgtaggggat  30300
tgcacagcca tacaccatca atttcctcag ccatctttgt cttcttactt ctgttttgct  30360
gcaacacaaa ggagccttga attcctctaa aattatcttc acagttttaa gcaatatcct  30420
tctagttctc ctggcacagc accttacccct aatctcgctt aaatcccaac agtaagtgca  30480
acataaaatt atcatattat taatatgccc gtaggtaaac cgccccacc caaaactaat  30540 ctttctctaaa gctgcagcag catgtatgtc atgttttact ttcaaccaaa ttaaatgcct  30600 cccctaaca tatgaacttc ccacataata cacctctttg ggcattttaa agttaacaat  30660
ttccctgtac cacagaaatc tctgatttat taaagctcca tacaccaaca tataaaacca  30720
tttagccaac agcacccctc cagctttaca ttgaagcgat cctggttttt cacaatggca  30780
atgtaaagtc cacaactcat aaccatgcag cacttcagat cttctcaaat caatactagc  30840
```

| | | | | |
|---|---|---|---|---|
| gcagcaatca | cacaccttca | taaaattttt | aagaatgttc | atttcatagt tagttagaat | 30900 |
| catgtcccaa | ggaacaggcc | attccagcaa | caccgccagg | gccgcacagc acggaagact | 30960 |
| gcgcacaaca | gctacactgt | gcatggtgag | agaactacat | tcaggtaagg ggcacgagta | 31020 |
| ggcgagggga | gatgcagcag | tcacacgccc | ttcagacggg | ggcagcatat gatggtgata | 31080 |
| aggactcaac | ctgcagaaga | atcttctgac | gcgcggggcc | atcccacatt aactcacgtc | 31140 |
| gcgcttcttc | gtacttgaag | tagcaaaacc | aggttctttg | ataacacact tcccgccgat | 31200 |
| gaggatcctt | tctcttctgg | tgttcactgc | gccaagcata | aacagaaac tcacgcaaac | 31260 |
| tggttaccag | ttcttcagca | ggaggagtaa | actctacaga | aaagcgacgg taattttgaa | 31320 |
| gatgttcagc | tactgtaaca | taagctaagc | ccatccaaga | tatgcatgca gaccgatccc | 31380 |
| tgaaaactgt | aggagcagaa | agagccggta | gcaccatgga | gactattcca aacgatctgg | 31440 |
| cagaatttca | aaatgcagat | ctcgaagatg | acaacgatct | ccaccgctac cctgatgata | 31500 |
| acgaacagcc | aggtcaaaaa | caatactgtt | ttccaaattc | tccaccgtgg cattgatcag | 31560 |
| atcagcaatt | cgcacttcca | caaaagaag | gatagcaaac | gcctgaccct gcagatgttc | 31620 |
| tatagccaga | gtagcatttt | gaaccatgcc | cagataattt | tcattttttcc agtcgcgaat | 31680 |
| aatctccaca | agaagagctt | ccagattcat | cccatgagca | ttaaaaagct cccacagcgc | 31740 |
| gccctcaatg | tacatccgca | ggcacaccctt | catgattact | gtagcagctc cgcctcctga | 31800 |
| gacacctgca | gtaaattaac | ccggcttaaa | tcaggatcta | ctccccgaca tcgaagcttc | 31860 |
| tggcgtagcg | aaagttgaag | atattcagca | aagtccgaaa | ccaccaaagc agtgttttcc | 31920 |
| tcgccaggct | gcaactcagc | agtggcgacg | gagcaaaaca | cacgaagaca gggagcaagc | 31980 |
| tgaaccacag | tagcgcccca | gaagcatagc | tgttgaggag | gagtgtaata atccatgcag | 32040 |
| tgataccaaa | agtaagagca | ttcctgacgc | aaaaagccaa | gcacgtctat attaagctca | 32100 |
| tgcaaataat | ccagcaaagc | ttgaggcacg | gtgacggaca | cccaaaccgg gcgatgagca | 32160 |
| aacatgctta | ccctggaaaa | gagaacacat | taaacttgcg | tggcttcaag cacagtagga | 32220 |
| taaatcacac | gatgcaaaag | aaaccttccc | accgcttgac | cacgttggcc atgataaaaa | 32280 |
| tcgggagtgt | gattgaaaag | caataacttc | aactcccatc | tagtgcaggg atccacagta | 32340 |
| tcggctcctg | caaaaatccc | ccgcctcaca | agatccccca | aaggtcccaa acggccgata | 32400 |
| tatcccggag | gcacttgcac | tctaatctgc | aagtacaaca | gcaacacccc ctcagggga | 32460 |
| attacaaaat | cctcaggaga | gaaaagagtg | tatacccccag | aatagccttc ctgaacaggc | 32520 |
| aatatgccat | gttcaccctc | ccggtaaaca | tacaaaaact | cttcattggt agccatacca | 32580 |
| aaagagaaca | gcacaggctc | agcagcgtcc | agaaatgttc | tgcgccgcta actgagctcg | 32640 |
| ctctgccttt | atactgaaaa | atactgacgt | caataaccac | ttaacacaaa gttcagacct | 32700 |
| atttttaatt | attgagtttc | acttccgcgt | tccgtttccg | cgttcttcgc tgacgcatta | 32760 |
| aacgcgccac | tccctcccac | aattcagcgc | ggctcgtgag | taatctgtta actgcgcgcc | 32820 |
| ccgcccgaac | cgcccaccgg | cccgcccatt | gacgtcacgg | ccaatcacag ttgtggacac | 32880 |
| gcccatctca | tttgcatatt | aacttctgtt | tacattgtaa | ggtatattat tgatgatg | 32938 |

<210> SEQ ID NO 17
<211> LENGTH: 129
<212> TYPE: PRT
<213> ORGANISM: Artificial Sequence
<220> FEATURE:
<223> OTHER INFORMATION: Synthetic polypeptide

<400> SEQUENCE: 17

```
Met Phe Ala His Arg Pro Val Trp Val Ser Val Thr Val Pro Gln Ala
1               5                   10                  15

Leu Leu Asp Tyr Leu His Glu Leu Asn Ile Asp Val Leu Gly Phe Leu
                20                  25                  30

Arg Gln Glu Cys Ser Tyr Phe Trp Tyr His Cys Met Asp Tyr Tyr Thr
            35                  40                  45

Pro Pro Gln Gln Leu Cys Phe Trp Gly Ala Thr Val Gln Leu Ala
    50                  55                  60

Pro Cys Leu Arg Val Phe Cys Ser Val Ala Thr Ala Glu Leu Gln Pro
65                  70                  75                  80

Gly Glu Glu Asn Thr Ala Leu Val Val Ser Phe Ala Glu Tyr Leu
                85                  90                  95

Gln Leu Ser Leu Arg Gln Lys Leu Arg Cys Arg Gly Val Asp Pro Asp
                100                 105                 110

Leu Ser Arg Val Asn Leu Leu Gln Val Ser Gln Glu Ala Glu Leu Leu
            115                 120                 125

Gln

<210> SEQ ID NO 18
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 18

Met Lys Val Cys Leu Arg Met Tyr Ile Glu Gly Ala Leu Trp Glu Leu
1               5                   10                  15

Phe Asn Ala His Gly Met Asn Leu Glu Ala Leu Leu Val Glu Ile Ile
                20                  25                  30

Arg Asp Trp Lys Asn Glu Asn Tyr Leu Gly Met Val Gln Asn Ala Thr
            35                  40                  45

Leu Ala Ile Glu His Leu Gln Gly Gln Ala Phe Ala Ile Leu Leu Phe
    50                  55                  60

Val Glu Val Arg Ile Ala Asp Leu Ile Asn Ala Thr Val Glu Asn Leu
65                  70                  75                  80

Glu Asn Ser Ile Val Phe Asp Leu Ala Val Arg Tyr His Gln Gly Ser
                85                  90                  95

Gly Gly Asp Arg Cys His Leu Arg Asp Leu His Phe Glu Ile Leu Pro
                100                 105                 110

Asp Arg Leu Glu
        115

<210> SEQ ID NO 19
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 19

Met Val Leu Pro Ala Leu Ser Ala Pro Thr Val Phe Arg Asp Arg Ser
1               5                   10                  15

Ala Cys Ile Ser Trp Met Gly Leu Ala Tyr Val Thr Val Ala Glu His
                20                  25                  30

Leu Gln Asn Tyr Arg Arg Phe Ser Val Glu Phe Thr Pro Pro Ala Glu
            35                  40                  45

Glu Leu Val Thr Ser Leu Arg Glu Phe Leu Phe Tyr Ala Trp Arg Ser
```

```
                50                  55                  60
Glu His Gln Lys Arg Lys Asp Pro His Arg Arg Glu Val Cys Tyr Gln
 65                  70                  75                  80

Arg Thr Trp Phe Cys Tyr Phe Lys Tyr Glu Glu Ala Arg Arg Glu Leu
                 85                  90                  95

Met Trp Asp Gly Pro Ala Arg Gln Lys Ile Leu Leu Gln Val Glu Ser
                100                 105                 110

Leu Ser Pro Ser Tyr Ala Ala Pro Val
            115                 120

<210> SEQ ID NO 20
<211> LENGTH: 287
<212> TYPE: PRT
<213> ORGANISM: Artificial Sequence
<220> FEATURE:
<223> OTHER INFORMATION: Synthetic polypeptide

<400> SEQUENCE: 20

Met Ala Pro Arg Val Arg Arg Phe Phe Cys Arg Leu Ser Pro Tyr His
  1               5                  10                  15

His His Met Leu Pro Pro Ser Glu Gly Arg Val Thr Ala Ala Ser Pro
                 20                  25                  30

Leu Ala Tyr Ser Cys Pro Leu Pro Glu Cys Ser Ser Leu Thr Met His
                 35                  40                  45

Ser Val Ala Val Arg Ser Leu Pro Cys Cys Ala Ala Leu Ala Val
             50                  55                  60

Leu Leu Glu Trp Pro Val Pro Trp Asp Met Ile Leu Thr Asn Tyr Glu
 65                  70                  75                  80

Met Asn Ile Leu Lys Asn Phe Met Lys Val Cys Asp Cys Cys Ala Ser
                 85                  90                  95

Ile Asp Leu Arg Arg Ser Glu Val Leu His Gly Tyr Glu Leu Trp Thr
                100                 105                 110

Leu His Cys His Cys Glu Lys Pro Gly Ser Leu Gln Cys Lys Ala Gly
            115                 120                 125

Gly Val Leu Leu Ala Lys Trp Phe Tyr Met Leu Val Tyr Gly Ala Leu
        130                 135                 140

Ile Asn Gln Arg Phe Leu Trp Tyr Arg Glu Ile Val Asn Phe Lys Met
145                 150                 155                 160

Pro Lys Glu Val Tyr Tyr Val Gly Ser Ser Tyr Val Arg Gly Arg His
                165                 170                 175

Leu Ile Trp Leu Lys Val Lys His Asp Ile His Ala Ala Ala Ala Leu
            180                 185                 190

Glu Lys Ile Ser Phe Gly Trp Gly Arg Phe Thr Tyr Gly His Ile Asn
        195                 200                 205

Asn Met Ile Ile Leu Cys Cys Thr Tyr Cys Trp Asp Leu Ser Glu Ile
    210                 215                 220

Arg Val Arg Cys Cys Ala Arg Arg Thr Arg Arg Ile Leu Leu Lys Thr
225                 230                 235                 240

Val Lys Ile Ile Leu Glu Glu Phe Lys Ala Pro Leu Cys Cys Ser Lys
                245                 250                 255

Thr Glu Val Arg Arg Gln Arg Trp Leu Arg Lys Leu Met Val Tyr Gly
            260                 265                 270

Cys Ala Ile Pro Tyr Lys Val Tyr Asp Ala Arg Pro Val Thr
        275                 280                 285

<210> SEQ ID NO 21
```

```
<211> LENGTH: 325
<212> TYPE: PRT
<213> ORGANISM: Artificial Sequence
<220> FEATURE:
<223> OTHER INFORMATION: Synthetic polypeptide

<400> SEQUENCE: 21

Met Lys Arg Ala Arg Ala Val Thr Glu Asp Phe Asn Pro Val Tyr Pro
1               5                   10                  15

Tyr Asp Thr Pro Thr Gly Gly Asn Val Ala Pro Phe Val Thr Pro Pro
            20                  25                  30

Phe Val Ser Pro Asp Gly Leu Gln Glu Ser Pro Pro Gly Thr Leu Ser
        35                  40                  45

Leu Asn Ile Lys Ser Pro Leu Thr Ile Thr Asn His Gln Leu Asp Ile
    50                  55                  60

Lys Leu Gly Ser Gly Leu Ser Val Ser Ser Lys Gly Glu Leu Glu Ala
65                  70                  75                  80

Ser Ser Thr Thr Thr Val Thr Ala Pro Leu Thr Asn Thr Asn Asn Ile
                85                  90                  95

Ile Gly Leu Ser Tyr Ser Asp Gly Leu Thr Leu Glu Gln Asn Phe Leu
            100                 105                 110

Lys Val Asn Leu Gly Ser Gly Leu Thr Phe Asp Asn Gln Ser Ile Thr
        115                 120                 125

Leu Asn Pro Pro Thr Leu Trp Thr Gly Pro Ala Ala Glu Pro Asn Ala
    130                 135                 140

Thr Val Leu Pro Pro Gly Ser Ala Asp Ile Pro Asp Tyr Asn Ala Cys
145                 150                 155                 160

Ile Thr Leu Ser Leu Thr Lys Ile Gly Pro Leu Val Asn Gly Leu Ile
                165                 170                 175

Ser Leu Ile Gly Ile Ser Ala Pro Leu Thr Pro Ile Ala Ala Asp Val
            180                 185                 190

Asn Ser Val Lys Val Ser Leu Leu Phe Asn Asp Asn Gly Gln Leu Ile
        195                 200                 205

Gly Pro Asp Phe Glu Thr Asp Thr Phe Gly Phe Lys Val Gly Asn Thr
    210                 215                 220

Ile Asp Thr Thr Ser Thr Ala Ser Arg Val Pro Phe Met Pro Asn Val
225                 230                 235                 240

Thr Thr Tyr Pro His Asn Ser Thr Gly Gln Ala Gly Ala Gly His Tyr
                245                 250                 255

Ile Ile Val Pro Gly Met Val Asn Ala Asp Ser Ser Lys Pro Cys Asn
            260                 265                 270

Leu Ile Val Gly Leu Asn Thr Ala Gly Ser Ser Gly Phe Ser Ile Thr
        275                 280                 285

Leu Glu Trp Thr Gly Leu Ala Asn Tyr Asn Leu Ser Leu Gly Thr Ser
    290                 295                 300

Thr Phe Phe Leu Val Ile Tyr His Lys Thr Lys Ile Lys Val His Lys
305                 310                 315                 320

Lys Phe Tyr Leu Arg
            325

<210> SEQ ID NO 22
<211> LENGTH: 127
<212> TYPE: PRT
<213> ORGANISM: Artificial Sequence
<220> FEATURE:
<223> OTHER INFORMATION: Synthetic polypeptide

<400> SEQUENCE: 22
```

Met Ser Asn Pro Leu Glu Ile Asp Gly Leu Arg Ser Glu Gln Gln Ala
1               5                   10                  15

Leu Met Val Arg Glu Arg Ala Arg Gln Arg Glu Leu Lys His Gln Glu
                20                  25                  30

Leu Leu Asp Leu Gln Asn Thr His Gln Cys Lys Arg Gly Ile Phe Cys
            35                  40                  45

Ala Val Lys Gln Ala Ser Leu Arg Phe Glu Met Leu Asn Pro Pro Asp
    50                  55                  60

His Glu Leu Gln Tyr Thr Ile Gln Gln Glu Arg Gln Asn Cys Val Phe
65                  70                  75                  80

Met Val Gly Ser Lys Pro Ile Lys Ile Thr Gln Ser Arg Gly Glu Val
                85                  90                  95

Thr Gly Ala Leu Arg Cys Ser Cys Thr His Ser Glu Cys Met Tyr Thr
            100                 105                 110

Leu Val Lys Thr Leu Cys Gly Leu His Asp Leu Ile Pro Phe Asn
            115                 120                 125

<210> SEQ ID NO 23
<211> LENGTH: 55
<212> TYPE: PRT
<213> ORGANISM: Artificial Sequence
<220> FEATURE:
<223> OTHER INFORMATION: Synthetic polypeptide

<400> SEQUENCE: 23

Met Asn Ile Ile Asp Ser Ser Gly Lys Val Val Lys Phe Asp Met Pro
1               5                   10                  15

Phe Arg Val Trp Arg Lys Phe Ala Ser Arg Arg Ser Ile Gly Tyr Gln
                20                  25                  30

Ser Trp Glu Glu Gly Lys Trp Val Lys Leu Asp Thr Lys Ala Thr Asn
            35                  40                  45

Lys Leu Thr Ala Glu Phe Met
    50                  55

<210> SEQ ID NO 24
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 24

Met Lys Ala Leu Leu Val Leu Ala Phe Leu Pro Leu Thr His Cys Cys
1               5                   10                  15

Arg Phe Thr Phe Ser Lys Leu Trp Thr Ile Arg Asp Cys Tyr Pro Phe
                20                  25                  30

Val Pro Val Arg Glu Glu Pro Trp Leu Phe Thr Ile Leu Ile Val Ala
            35                  40                  45

Ala Leu Ile Ala Phe Phe Ala Ala Ile Tyr Leu Arg Asn Ile Leu Pro
    50                  55                  60

Phe Ser Trp Asn Thr Asp Asp Leu Leu Asp Tyr Pro Ile Leu Pro Gln
65                  70                  75                  80

Pro Asn Val Ile Pro Leu Gln Asn Leu Leu Pro Asn Leu Pro Asp Leu
                85                  90                  95

Leu Asp Gln Leu Pro Pro Asn Pro Asp Pro Pro Arg Ser Pro Ser Thr
            100                 105                 110

Cys Ser Tyr Phe Arg Phe Thr Asn Glu
            115                 120

```
<210> SEQ ID NO 25
<211> LENGTH: 92
<212> TYPE: PRT
<213> ORGANISM: Artificial Sequence
<220> FEATURE:
<223> OTHER INFORMATION: Synthetic polypeptide

<400> SEQUENCE: 25

Met Thr Leu Ala Leu Leu Ile Cys Thr Leu Thr Val Pro Val Thr Leu
1               5                   10                  15

Ala Thr Val Ser Phe Ala Thr Thr His Leu Glu Pro Glu Cys Leu
            20                  25                  30

Pro Pro Phe Gln Val Tyr Leu Val Phe Ser Phe Leu Cys Cys Thr Cys
            35                  40                  45

Ile Ala Ser Leu Ile Thr Leu Leu Val Phe Phe Gln Phe Val Asp
        50                  55                  60

Tyr Phe Leu Val Arg Leu Arg Tyr Arg His His Ala Pro Gln Phe Gln
65                  70                  75                  80

Asn Pro Asn Val Ala Arg Leu Leu Ala Leu Gln Pro
                85                  90

<210> SEQ ID NO 26
<211> LENGTH: 155
<212> TYPE: PRT
<213> ORGANISM: Artificial Sequence
<220> FEATURE:
<223> OTHER INFORMATION: Synthetic polypeptide

<400> SEQUENCE: 26

Met Lys Phe Leu Leu Phe Thr Ile Leu Phe Ser Leu Cys Gly Ser Ser
1               5                   10                  15

His Ser Val Phe Tyr Pro Pro Asn Cys Tyr Val Thr Ser Arg Trp
            20                  25                  30

Asp Pro Asn Cys His Ile Gln Ile Leu Cys Pro Asp Asn Ser Thr Ile
            35                  40                  45

Tyr Tyr Ser Asn Thr Ser Val Val Gly Ser Leu Thr Leu Asn Pro Glu
        50                  55                  60

Asp Asn Pro Pro Asp His Tyr Leu Ile Asn His Thr Leu Ser Asn Gly
65                  70                  75                  80

Lys Thr Ala Leu Tyr Asn Phe Thr Phe Pro Met Ala Thr Leu Cys Thr
                85                  90                  95

Ile Thr Glu Ala Thr Asp Ser Gly Tyr Asp Phe Thr Val Leu Phe Leu
            100                 105                 110

Leu Leu Met Val Val Ala Leu Ile Leu Leu Ala Ala Leu Ala Cys
            115                 120                 125

Leu Phe Tyr His Tyr Cys Arg Trp Trp Arg Lys Gly Ser Tyr Thr Leu
        130                 135                 140

Pro His Asp Gln Arg Ser Ile His Leu Glu Ile
145                 150                 155

<210> SEQ ID NO 27
<211> LENGTH: 342
<212> TYPE: PRT
<213> ORGANISM: Artificial Sequence
<220> FEATURE:
<223> OTHER INFORMATION: Synthetic Polypeptide

<400> SEQUENCE: 27

Met Gln Thr Ser Ala Ala Ile Cys Val Leu Ala Leu Ile Ser Phe Val
```

```
                1               5                  10                  15
        Ser Cys Val Gln Pro Ala Ser Gly Gln Ile Asp Val Cys Gln Ala Ala
                        20                  25                  30

Asn Val Thr Val Thr Asp Leu Ser Lys Pro Thr Ile Thr Val Lys Cys
                        35                  40                  45

Gly Phe Tyr Asn Lys Pro Val Ser Thr Val Phe Trp Tyr Phe Asn Asn
                        50                  55                  60

Thr Leu Phe Ser Ser Phe Asn Pro Phe Ser Leu Ile Ser Asn Ile
         65                  70                  75                  80

Lys Gln Pro Phe Asn Tyr Tyr Thr Thr Gly Asn Ser Leu Gln Leu Phe
                        85                  90                  95

Ala Pro Tyr Ser Ser Gly Arg Tyr His Cys Glu Val Leu Lys Cys Thr
                        100                 105                 110

Gln His Phe Phe Ile Gly Ile Lys Pro Ala Thr Pro Ile Thr Thr Ala
                        115                 120                 125

Ala Thr Thr Thr Thr Pro Asn Thr Thr Ala Val Thr Thr Pro Pro Pro
                        130                 135                 140

Ala Thr Ala Ser Ser Thr Thr Thr Pro Ala Ala Ala Thr Thr Ser
        145                 150                 155                 160

Ser Pro Ser Ala Pro Lys Arg Ser Ile Arg Ser Phe Ser His Ser Phe
                        165                 170                 175

Leu Ser Ile Asn Val Ser Asp Pro Thr Gln Val Leu Gln Cys Pro Cys
                        180                 185                 190

Ser Gly Asn Tyr Thr Phe Trp Gly Val Asn Gly Thr Asp Trp Ala Phe
                        195                 200                 205

Val Gln Asn Ile Thr Phe Val Thr Phe Ile Gln Asn Gln Thr Ile Asn
                        210                 215                 220

Phe Asn His Lys Phe Leu Asn Thr Ser Leu Asn Leu Arg Leu Pro Val
        225                 230                 235                 240

Val Pro Gly Asn Tyr Ser Cys Asp Thr Gln Ser Arg Gln Cys Gln His
                        245                 250                 255

Val Phe Thr Val Thr Val Ile Tyr Pro Thr Pro Thr Thr Pro Ala Pro
                        260                 265                 270

Pro Thr Thr Ala Thr Glu Thr Asn Thr His Gln Ala Phe Phe Ala Pro
                        275                 280                 285

Ser Glu Ala Pro Glu Thr Ala Val Ala Ser Thr Pro Trp Trp Leu Phe
                        290                 295                 300

Val Val Val Gly Ile Val Val Val Ile Ile Ala Gly Ala Val Thr Ala
        305                 310                 315                 320

Phe Phe Ile Tyr Lys Lys His Pro Glu Val Val Val Phe His Arg
                        325                 330                 335

Val Pro Thr Ser Val Tyr
                        340

<210> SEQ ID NO 28
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 28

Met Ser Asn Glu Phe Glu Ser Leu Val Asp Gln Ala Arg Ile Arg His
1               5                   10                  15

Leu Asp His Cys Arg Arg His Arg Cys Phe Val Arg Glu His Leu Gln
                20                  25                  30
```

```
Thr Val Tyr Phe Glu His Pro Glu Ser His Pro Asp Gly Pro Cys His
        35                  40                  45
Gly Ile Tyr Val Ile Val Asp Gly Ser Cys Asp Thr His Leu Val Arg
 50                  55                  60
Tyr Tyr Ser Gln Arg Pro Leu Leu Val Glu Arg Gln Thr Gly Val Thr
 65                  70                  75                  80
Lys Ile Thr Leu Thr Cys Ile Cys Ser Gln Pro Gly Leu His Ala Asp
             85                  90                  95
Leu Cys Cys His Leu Cys Ala Arg Phe Asn Gln Leu Arg
            100                 105
```

<210> SEQ ID NO 29
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 29

```
Met Ser Lys Glu Ile Pro Thr Pro Tyr Met Trp Ser Tyr Gln Pro Gln
 1               5                  10                  15
Met Gly Leu Ala Ala Gly Ala Ala Gln Asp Tyr Ser Thr Lys Met Asn
             20                  25                  30
Trp Leu Ser Ala Gly Pro His Met Ile Ala Gln Val Asn Gly Ile Arg
         35                  40                  45
Ala His Arg Asn Gln Leu Leu Leu Glu Gln Ala Leu Thr Thr Thr
 50                  55                  60
Pro Arg Asn Gln Leu Asn Pro Pro Ser Trp Pro Ala Ser Leu Val Tyr
 65                  70                  75                  80
Gln Glu Thr Pro Ala Pro Thr Thr Val Leu Leu Pro Arg Asp Ala Gln
             85                  90                  95
Ala Glu Val Leu Met Thr Asn Ser Gly Ala Gln Leu Ala Gly Gly Ala
            100                 105                 110
Cys Arg Tyr Arg Ser Lys Gly Pro Thr Gly Leu Ser Ala Pro Leu Gly
        115                 120                 125
Ile Lys Arg Val Leu Ile Arg Gly Arg Gly Thr Gln Leu Asn Asp Glu
130                 135                 140
Thr Val Ser Ser Ser Leu Gly Leu Arg Pro Asp Gly Val Phe Gln Leu
145                 150                 155                 160
Ala Gly Ser Gly Arg Ser Ser Phe Thr Pro Arg Gln Ala Tyr Leu Thr
            165                 170                 175
Leu Gln Ser Ser Ser Gln Pro Arg Ser Gly Gly Ile Gly Thr Leu
        180                 185                 190
Gln Phe Val Glu Glu Phe Thr Pro Ser Val Tyr Phe Asn Pro Phe Ser
    195                 200                 205
Gly Ala Pro Gly Leu Tyr Pro Asp Glu Phe Ile Pro Asn Phe Asp Ala
        210                 215                 220
Val Thr Asp Ser Val Asp Gly Tyr Asp
225                 230
```

<210> SEQ ID NO 30
<211> LENGTH: 254
<212> TYPE: PRT
<213> ORGANISM: Artificial Sequence
<220> FEATURE:
<223> OTHER INFORMATION: Synthetic polypeptide

<400> SEQUENCE: 30

Met Pro Pro Lys Lys Arg Ser Ala Ala Leu Pro Leu Ser Lys Ala Val
1               5                   10                  15

Thr Ala Lys Arg Pro Lys Gln Arg Lys Ala Gln Glu Thr Glu Glu Pro
            20                  25                  30

Trp Ser Glu Glu Glu Asp Trp Glu Ser Gln Gly Glu Glu Asp Met Glu
            35                  40                  45

Glu Glu Trp Asp Ser Leu Ala Ser Asp Glu Gly Glu Ala Glu Ala Glu
        50                  55                  60

Thr Glu Glu Ala Ser Val Ala Lys Pro Ser Leu Ala Lys Arg Val Ser
65                  70                  75                  80

Asn Val Thr Thr Thr Ser Asp Gln Arg Thr Val Ser Arg Arg Trp Asp
                    85                  90                  95

Ser Thr Asn Ala Ala Pro Ala Gly Lys Thr Leu Ser Leu Ala Lys Pro
                100                 105                 110

Arg Gln Gly Tyr Arg Ser Trp Arg Ala His Lys Asn Ala Ile Ile Asn
            115                 120                 125

Cys Leu Glu Asn Cys Gly Gly Asn Ile Ser Phe Thr Arg Arg Phe Met
        130                 135                 140

Leu Phe Arg Asn Gly Ile Ala Ile Pro Arg Asn Val Leu His Tyr Tyr
145                 150                 155                 160

Arg His Ser Tyr Ser Pro Ser Lys Thr Arg Leu Pro Lys Gln Asn Lys
                165                 170                 175

Lys Gln Val Lys Glu Pro Pro Ser Thr Lys Glu Leu Arg Asn Arg Ile
            180                 185                 190

Phe Pro Thr Leu Tyr Ala Ile Phe Gln Gln Ser Arg Gly Gln Glu Pro
        195                 200                 205

Glu Leu Lys Ile Lys Asn Arg Ser Leu Arg Ser Leu Thr Arg Ser Cys
210                 215                 220

Leu Tyr His Lys Asn Glu Glu Gln Leu Gln Arg Thr Leu Asp Asp Ala
225                 230                 235                 240

Glu Ala Leu Phe Asn Lys Tyr Cys Ala Ala Thr Leu Lys Glu
                245                 250

<210> SEQ ID NO 31
<211> LENGTH: 180
<212> TYPE: PRT
<213> ORGANISM: Artificial Sequence
<220> FEATURE:
<223> OTHER INFORMATION: Synthetic polypeptide

<400> SEQUENCE: 31

Met Pro Pro Lys Lys Arg Ser Ala Ala Leu Pro Leu Ser Lys Ala Val
1               5                   10                  15

Thr Ala Lys Arg Pro Lys Gln Arg Lys Ala Gln Glu Thr Glu Glu Pro
            20                  25                  30

Trp Ser Glu Glu Glu Asp Trp Glu Ser Gln Gly Glu Glu Asp Met Glu
            35                  40                  45

Glu Glu Trp Asp Ser Leu Ala Ser Asp Glu Gly Glu Ala Glu Ala Glu
        50                  55                  60

Thr Glu Glu Ala Ser Val Ala Lys Pro Ser Leu Ala Lys Arg Val Ser
65                  70                  75                  80

Asn Val Thr Thr Thr Ser Asp Gln Arg Thr Val Ser Arg Arg Trp Asp
                    85                  90                  95

Ser Thr Asn Ala Ala Pro Ala Gly Lys Thr Leu Ser Leu Ala Lys Pro
                100                 105                 110

```
Arg Gln Gly Tyr Arg Ser Trp Arg Ala His Lys Asn Ala Ile Ile Asn
            115                 120                 125
Cys Leu Glu Asn Cys Gly Gly Asn Ile Ser Phe Thr Arg Arg Phe Met
        130                 135                 140
Leu Phe Arg Asn Gly Ile Ala Ile Pro Arg Asn Val Leu His Tyr Tyr
145                 150                 155                 160
Arg His Ser Tyr Ser Pro Ser Lys Thr Val Pro Leu Gly Ser Gly Gly
                    165                 170                 175
Arg Gly Gly His
            180
```

<210> SEQ ID NO 32
<211> LENGTH: 780
<212> TYPE: PRT
<213> ORGANISM: Artificial Sequence
<220> FEATURE:
<223> OTHER INFORMATION: Synthetic polypeptide

<400> SEQUENCE: 32

```
Met Glu Leu Glu Pro Ala Ala Glu Ser Asn Asn Leu Thr Ser Pro His
1               5                   10                  15
Phe Tyr Glu Asn Lys Asp Ala Leu Thr Glu Ala Thr Gly Ser Ala Val
            20                  25                  30
Glu Gln Asp Val Gly Tyr Ala Ser Pro Pro Glu Thr Ala Glu Glu Glu
        35                  40                  45
Lys Asp Asp Lys Asn Leu Ser Ser Pro Gln Lys Asp Lys Gln Gln Asp
    50                  55                  60
Asp Lys Thr Gln Glu Asn Glu Asp Val Ser Phe His Asp Asp Tyr
65                  70                  75                  80
Leu Gly Lys Gly Glu Asp Val Leu Leu Lys His Ile Arg Arg Gln Ser
                85                  90                  95
Ala Ile Val Glu Asn Ala Ile Ser Glu Lys Thr Glu Ile Pro Val Ser
            100                 105                 110
Val Tyr Asp Leu Ser Leu Ala Tyr Glu Gln Ser Leu Phe Ser Pro Arg
        115                 120                 125
Val Pro Pro Lys Arg Gln Pro Asn Gly Thr Cys Glu Pro Asn Pro Arg
    130                 135                 140
Leu Asn Phe Tyr Pro Ala Phe Ala Val Pro Glu Val Leu Ala Thr Tyr
145                 150                 155                 160
His Ile Phe Phe Lys Asn His Lys Ile Pro Val Ser Cys Arg Ala Asn
                165                 170                 175
Arg Ser Glu Ala Asp Ala Gln Leu Leu Leu Gly Pro Gly Ala Arg Ile
            180                 185                 190
Pro Asp Phe Ala Ser Leu Glu Glu Val Pro Lys Ile Phe Glu Gly Leu
        195                 200                 205
Gly Asp Glu Lys Arg Ala Ala Asn Ala Leu Gln Glu Asn Thr Glu Ser
    210                 215                 220
Phe Ser Ala Leu Val Glu Leu Ala Asn Asp Asn Ala Arg Leu Ala Val
225                 230                 235                 240
Leu Lys Arg Ser Val Glu Val Thr His Phe Ala Tyr Pro Ala Val Asn
                245                 250                 255
Leu Pro Pro Lys Val Met Asn Thr Val Met Asp Cys Leu Leu Val Lys
            260                 265                 270
Arg Ala Lys Pro Leu Gly Glu Gly Glu Gln Glu Glu Glu Asp Ser Asp
        275                 280                 285
Glu Gly Lys Pro Ala Val Thr Asp Glu Glu Leu Ser Arg Trp Leu Arg
```

```
            290                 295                 300
Thr Thr Asp Pro Ala Glu Leu Glu Asn Arg Arg Lys Leu Met Thr Ala
305                 310                 315                 320

Val Ile Leu Val Thr Ala Glu Leu Glu Cys Leu Ser Arg Phe Phe Thr
                325                 330                 335

Asp Thr Glu Thr Ile Arg Lys Val Glu Glu Thr Leu His Tyr Thr Phe
            340                 345                 350

Arg His Gly Tyr Val Lys Gln Ala Cys Lys Ile Ser Asn Val Glu Leu
        355                 360                 365

Ser Asn Leu Val Ser Tyr Leu Gly Ile Leu His Glu Asn Arg Leu Gly
    370                 375                 380

Gln Asn Val Leu His Ala Thr Leu Lys Gly Glu Ala Arg Arg Asp Tyr
385                 390                 395                 400

Ile Arg Asp Cys Val Tyr Leu Phe Leu Cys Phe Thr Trp Gln Ser Ala
                405                 410                 415

Met Gly Val Trp Gln Gln Cys Leu Glu Asp Asp Asn Leu Arg Glu Leu
            420                 425                 430

Gln Lys Ile Leu Asn Arg Glu Arg Arg Asp Leu Trp Thr Gly Phe Asp
        435                 440                 445

Glu Arg Thr Val Ala Lys Asp Leu Ala Asn Ile Ile Phe Pro Ser Arg
450                 455                 460

Leu Val Arg Thr Leu Gln Asn Gly Leu Pro Asp Phe Met Ser Gln Ser
465                 470                 475                 480

Met Ile Gln Asn Phe Arg Ser Phe Ile Leu Glu Arg Ser Gly Ile Leu
                485                 490                 495

Pro Ser Met Ser Cys Ala Leu Pro Ser Asp Phe Ile Pro Leu Thr Phe
            500                 505                 510

Arg Glu Cys Pro Pro Leu Trp Ser His Cys Tyr Leu Phe Gln Leu
        515                 520                 525

Ala Asn Phe Phe Ala Phe His Ser Asp Val Val Ala Asp Val Thr Gly
530                 535                 540

Glu Gly Leu Met Glu Cys His Cys Arg Cys Asn Leu Cys Thr Pro His
545                 550                 555                 560

Arg Ser Leu Val Cys Asn Thr Ala Leu Leu Asn Glu Thr Gln Val Ile
                565                 570                 575

Gly Thr Phe Glu Ile Gln Gly Pro Ser Glu Asn Lys Gly Ala Ala
            580                 585                 590

Gly Leu Lys Leu Thr Pro Gly Leu Trp Thr Ser Ala Tyr Leu Arg Lys
        595                 600                 605

Phe Val Pro Val Asp Tyr His Ala His Glu Ile Arg Phe Tyr Glu Asp
610                 615                 620

Gln Ser Gly Pro Pro Lys Ala Glu Leu Ser Ala Cys Val Ile Thr Gln
625                 630                 635                 640

Ser Ser Ile Val Ala Gln Leu Gln Ala Ile Asn Glu Ala Arg Arg Asn
                645                 650                 655

Phe Leu Leu Lys Lys Gly Lys Gly Val Tyr Leu Asp Pro Gln Thr Gly
            660                 665                 670

Glu Glu Leu Asn Thr Thr Pro Ser Pro Val Ala Gly Val Ser His Asn
        675                 680                 685

Ala Thr Lys Glu Glu Val Arg Arg Pro Pro Ala Leu Gln Ser Ser His
        690                 695                 700

Ser Lys Ala Thr Gln Thr Glu Glu Ser Pro Gly Asp Arg Gly Thr Met
705                 710                 715                 720
```

```
Glu Arg Gly Gly Gly Leu Gly Glu Ser Gly Arg Gly His Gly Arg
            725                 730                 735

Gly Met Gly Gln Pro Ser Gln Arg Arg Gly Arg Gly Arg Gly Arg Asp
            740                 745                 750

Arg Gly Ser Ile Arg Arg Lys Thr Leu Thr Gly Glu Thr Ser Phe Lys
        755                 760                 765

Arg Tyr Tyr Asp Leu Arg Ser Ala His Ser Gln Ser
770                 775                 780

<210> SEQ ID NO 33
<211> LENGTH: 457
<212> TYPE: PRT
<213> ORGANISM: Artificial Sequence
<220> FEATURE:
<223> OTHER INFORMATION: Synthetic polypeptide

<400> SEQUENCE: 33

Met Ala Ser Asn Gln Asp Arg Arg Glu Val Thr Pro Glu Lys Val Pro
1               5                   10                  15

Ala Val Pro Pro Lys Lys Lys Ala Arg Lys Ser Leu Pro Leu Pro Pro
            20                  25                  30

Ser Pro Glu Val Val Ala Asp Ser Asp Glu Glu Val Gly Glu Leu Leu
        35                  40                  45

Glu Val Gly Phe Ser Tyr Pro Pro Val Lys Ile Val Arg Lys Ala Asp
    50                  55                  60

Gly Ser Lys Ala Phe Glu Lys Phe Asp Glu Asn His Pro Ile Met Ser
65                  70                  75                  80

Ala Ala Arg Gln Gln Lys Glu Gly Thr Ser Ser Thr Val Val Asn Pro
                85                  90                  95

Ala Ser Asn Pro Leu Val Ser Ala Trp Glu Lys Gly Met Glu Phe Met
            100                 105                 110

Val Met Leu Met Glu Arg Tyr Lys Val Asp Lys Glu Leu Arg Ser Ser
        115                 120                 125

Phe Lys Phe Leu Pro Glu Gln Gly Glu Val Tyr Arg Lys Ile Cys Gln
    130                 135                 140

Ala Trp Met Asn Glu Glu Tyr Lys His Asn Thr Leu Thr Phe Thr Ser
145                 150                 155                 160

His Lys Ser Phe Ile Ser Leu Met Gly Arg Phe Leu Met Ala Tyr Val
                165                 170                 175

Gln Val Tyr Ala Gly Val Asp Ser Lys Leu Trp Glu Pro Thr Gly Cys
            180                 185                 190

Val Ala Trp Glu His Gln Cys Thr Asp Val Glu Gly Glu Leu Lys Cys
        195                 200                 205

Leu His Gly Leu Thr Met Ile Val Lys Glu Gln Ile Ile Glu Met Asp
    210                 215                 220

Val Thr Ser Glu Asn Gly Gln Arg Ala Leu Lys Glu Thr Pro Ala Lys
225                 230                 235                 240

Ala Lys Ile Val Gln Asn Arg Trp Gly Arg Ser Val Val Gln Val Arg
                245                 250                 255

Asn Glu Asp Ala Arg Cys Cys Met Phe Asp Ala Gly Cys Ser Pro Asn
            260                 265                 270

Asn Phe Ser Asn Lys Ser Cys Gly Met Phe Tyr Ser Glu Gly Thr Lys
        275                 280                 285

Ala Gln Ile Ala Phe Arg Gln Ile Ala Ala Phe Met Gln Ala Cys Tyr
    290                 295                 300

Pro His Met Val Lys Gly Ser Lys His Leu Leu Met Pro Ile Arg Cys
```

305                 310                 315                 320
Asn Cys Phe Thr Arg Pro Glu Met Ser Arg Gly Gly Arg Gln Thr Cys
                325                 330                 335

Lys Ile Thr Pro Phe Ala Leu Asn Val Glu Asn Ile His Leu Glu Asp
            340                 345                 350

Leu Val Asp Phe Gly Tyr His Asp Arg Ala Met Leu Ala Ser Val Asn
        355                 360                 365

Asn Pro Ser Val Leu Val Phe Gln Cys Ala Asn Ala Leu His Arg Asn
    370                 375                 380

Ser Lys Ala Asn Asn Gln Ala Asn Cys Asp Phe Lys Ile Ser Ala Pro
385                 390                 395                 400

Asp Val Ile Gly Ala Leu Gln Leu Val Arg Gln Phe Trp Gln Asp His
                405                 410                 415

Leu Pro Asp Thr Val Leu Pro Lys Met Val Val Pro Glu Phe Lys Trp
            420                 425                 430

His Pro Lys Tyr Gln Tyr Arg Asn Leu Thr Leu Pro Ala Ala His Val
        435                 440                 445

Asp Phe Glu Met Asn Pro Phe Glu Phe
    450                 455

<210> SEQ ID NO 34
<211> LENGTH: 206
<212> TYPE: PRT
<213> ORGANISM: Artificial Sequence
<220> FEATURE:
<223> OTHER INFORMATION: Synthetic polypeptide

<400> SEQUENCE: 34

Met Gly Ser Ser Glu Glu Glu Leu Lys Ala Ile Ile Arg Asp Leu Arg
1               5                   10                  15

Cys Ala Pro Tyr Phe Leu Gly Thr Phe Asp Lys Arg Phe Pro Gly Phe
            20                  25                  30

Val Ser Pro His Lys Leu Ala Cys Ala Ile Val Asn Thr Ala Gly Arg
        35                  40                  45

Glu Thr Gly Gly Val His Trp Leu Ala Phe Gly Trp Asn Pro Lys Asn
    50                  55                  60

Arg Thr Cys Tyr Leu Phe Asp Pro Phe Gly Phe Ser Asp Glu Lys Leu
65                  70                  75                  80

Lys Gln Ile Tyr Gln Phe Glu Tyr Glu Asn Leu Leu Lys Arg Ser Ala
                85                  90                  95

Ile Ala Ser Thr Pro Asp Arg Cys Val Thr Leu Val Lys Ser Thr Gln
            100                 105                 110

Thr Val Gln Gly Pro Asn Ser Ala Ala Cys Gly Leu Phe Ala Cys Met
        115                 120                 125

Phe Leu His Ala Phe Val Asn Trp Pro Asn Ser Pro Met Glu Asn Asn
    130                 135                 140

Pro Thr Met Asp Leu Ile Val Gly Val Pro Asn Tyr Met Leu Lys Ser
145                 150                 155                 160

Pro Gln Val Gln Gly Thr Leu Phe Lys Asn Gln Ala Leu Tyr Arg
                165                 170                 175

Phe Leu Ala Thr His Ser Pro Tyr Phe Arg His His Gln Gln Ile
            180                 185                 190

Glu Lys Ala Thr Ala Phe Asn Lys Gln Thr Glu Ser Lys Asn
        195                 200                 205

<210> SEQ ID NO 35

-continued

<211> LENGTH: 937
<212> TYPE: PRT
<213> ORGANISM: Artificial Sequence
<220> FEATURE:
<223> OTHER INFORMATION: Synthetic polypeptide

<400> SEQUENCE: 35

```
Met Ala Thr Pro Ser Met Met Pro Gln Trp Ser Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Thr Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Thr Ala Tyr Ala Tyr
65                  70                  75                  80

Lys Ala Arg Phe Thr Leu Ser Val Gly Asp Asn Arg Val Leu Asp Met
                85                  90                  95

Ala Ser Thr Tyr Phe Asp Ile Arg Gly Val Ile Asp Arg Gly Pro Ser
            100                 105                 110

Phe Lys Pro Tyr Ser Gly Thr Ala Tyr Asn Ala Leu Ala Pro Lys Gly
        115                 120                 125

Ala Pro Asn Asn Ser Gln Trp His Thr Val Asn Glu Asp Asn Gln Asn
    130                 135                 140

Phe Leu Met His Thr Tyr Ala Gln Ala Pro Phe Glu Ser Glu Phe Val
145                 150                 155                 160

Ala Asn Asn Gly Asn Ile Gly Ile Gln Val Gly Val Ser Asp Thr Asn
                165                 170                 175

Thr Pro Ile Leu Ala Asp Pro Thr Tyr Gln Pro Glu Pro Gln Asp Gly
            180                 185                 190

Glu Pro Gln Trp Gln Ser Leu Lys Ala Gln Glu Lys Leu Glu His Ala
        195                 200                 205

Gly Arg Ala Leu Lys Tyr Thr Thr Pro Met Lys Pro Cys Tyr Gly Ser
    210                 215                 220

Tyr Ala Arg Pro Thr Asn Ala Gln Gly Gly Gln Gly Ile Ile Asp Glu
225                 230                 235                 240

Gln Thr Gly Glu Thr Asp Ala Thr Glu Ile Thr Gln Asn Tyr Phe Ala
                245                 250                 255

Leu Ser Thr Ala Thr Thr Asp Phe Thr Pro Lys Val Val Leu Tyr Thr
            260                 265                 270

Glu Asp Val Tyr Leu Gln Thr Pro Asp Thr His Leu Val Tyr Thr Pro
        275                 280                 285

Ser Ala Thr Glu Gly Ser Thr Gln Asp Met Leu Gly Gln Gln Ala Ala
    290                 295                 300

Pro Asn Arg Pro Asn Tyr Ile Gly Phe Arg Asp Asn Phe Ile Gly Leu
305                 310                 315                 320

Met Tyr Tyr Asn Ser Thr Gly Asn Met Gly Val Leu Ala Gly Gln Ala
                325                 330                 335

Ser Gln Leu Asn Ala Val Val Asp Leu Gln Asp Arg Asn Thr Glu Leu
            340                 345                 350

Ser Tyr Gln Leu Met Leu Asp Ala Leu Ser Asp Arg Thr Arg Tyr Phe
        355                 360                 365

Ser Met Trp Asn Gln Ala Val Asp Ser Tyr Asp Pro Asp Val Arg Ile
    370                 375                 380
```

-continued

```
Ile Glu Asn His Gly Val Glu Asp Leu Pro Thr Tyr Cys Phe Pro
385                 390                 395                 400

Leu Ser Gly Val Gly Ile Thr Gln Glu Tyr Gln Gly Val Glu Pro Thr
            405                 410                 415

Asn Pro Ala Ala Ala Asp Ile Thr Trp Lys Glu Asp Ala Thr Val Phe
                420                 425                 430

Asp Pro Asn Tyr Ile Ala Thr Gly Asn Ile Asn Ala Tyr Glu Ile Asn
            435                 440                 445

Leu Gln Ala Ser Leu Trp Arg Ser Phe Leu Tyr Ser Asn Val Ala Leu
    450                 455                 460

Tyr Leu Pro Asp Lys Tyr Lys Tyr Thr Pro Ala Asn Val Thr Leu Pro
465                 470                 475                 480

Thr Asn Thr Asn Thr Tyr Lys Tyr Met Asn Gly Arg Val Thr Ser Pro
                485                 490                 495

Ser Leu Val Asp Ile Phe Val Asn Val Gly Ala Arg Trp Ser Pro Asp
            500                 505                 510

Pro Met Asp Asn Val Asn Pro Phe Asn His His Arg Asn Ala Gly Leu
        515                 520                 525

Arg Tyr Arg Ser Gln Leu Leu Gly Asn Gly Arg Ile Val Pro Phe His
530                 535                 540

Ile Gln Val Pro Gln Lys Phe Phe Ala Ile Lys Asn Leu Leu Leu Leu
545                 550                 555                 560

Pro Gly Ser Tyr Thr Tyr Glu Trp Ser Phe Arg Lys Asp Val Asn Met
                565                 570                 575

Ile Leu Gln Ser Thr Leu Gly Asn Asp Leu Arg Thr Asp Gly Ala Ala
            580                 585                 590

Ile Arg Ile Glu Ser Val Asn Leu Tyr Ala Asn Phe Phe Pro Met Ala
    595                 600                 605

His Asn Thr Ala Ser Thr Leu Glu Ala Met Leu Arg Asn Asp Thr Asn
    610                 615                 620

Asp Gln Ser Phe Asn Asp Tyr Leu Ser Ala Ala Asn Met Leu Tyr Pro
625                 630                 635                 640

Ile Pro Ala Asn Ala Thr Asn Val Pro Ile Ser Ile Pro Ser Arg Asn
                645                 650                 655

Trp Ala Ala Phe Arg Gly Trp Ser Phe Thr Arg Leu Lys Ala Lys Glu
            660                 665                 670

Thr Pro Ala Leu Gly Ser Gly Phe Asp Pro Tyr Phe Val Tyr Ser Gly
        675                 680                 685

Ser Ile Pro Tyr Leu Asp Gly Thr Phe Tyr Leu Asn His Thr Phe Lys
    690                 695                 700

Arg Val Ser Ile Met Phe Asp Ser Ser Val Ser Trp Pro Gly Asn Asp
705                 710                 715                 720

Arg Leu Leu Thr Pro Asn Glu Phe Glu Val Lys Arg Val Val Asp Gly
                725                 730                 735

Glu Gly Tyr Thr Val Ala Gln Ser Asn Met Thr Lys Asp Trp Phe Leu
            740                 745                 750

Ile Gln Met Leu Ser His Tyr Asn Ile Gly Tyr Gln Gly Phe Tyr Ile
        755                 760                 765

Pro Glu Gly Tyr Lys Asp Arg Met Tyr Ser Phe Phe Arg Asn Phe Gln
    770                 775                 780

Pro Met Thr Arg Gln Ala Val Asp Pro Val Asn Tyr Thr Asn Tyr Lys
785                 790                 795                 800

Glu Ile Thr Val Ala His Gln His Asn Asn Ser Gly Phe Val Gly Phe
                805                 810                 815
```

```
Met Gly Pro Thr Met Arg Glu Gly His Pro Tyr Pro Ala Asn Tyr Pro
            820                 825                 830

Tyr Pro Leu Ile Gly Asp Ser Ala Val Pro Thr Val Thr Gln Lys Lys
            835                 840                 845

Phe Leu Cys Asp Arg Thr Met Trp Arg Ile Pro Phe Ser Ser Asn Phe
            850                 855                 860

Met Ser Met Gly Ala Leu Thr Asp Leu Gly Gln Asn Met Leu Tyr Ala
865                 870                 875                 880

Asn Ser Ala His Ala Leu Asp Met Thr Phe Glu Val Asp Pro Met Asp
                885                 890                 895

Glu Pro Thr Leu Leu Tyr Val Leu Phe Glu Val Phe Asp Val Val Arg
            900                 905                 910

Val His Gln Pro His Arg Gly Ile Ile Glu Ala Val Tyr Leu Arg Thr
            915                 920                 925

Pro Phe Ser Ala Gly Asn Ala Thr Thr
            930                 935

<210> SEQ ID NO 36
<211> LENGTH: 247
<212> TYPE: PRT
<213> ORGANISM: Artificial Sequence
<220> FEATURE:
<223> OTHER INFORMATION: Synthetic polypeptide

<400> SEQUENCE: 36

Met Glu Asp Val Asn Phe Ser Ser Leu Ala Pro Arg His Gly Thr Arg
1               5                   10                  15

Pro Tyr Leu Gly Thr Trp Asn Asp Ile Gly Thr Ser Gln Leu Asn Gly
            20                  25                  30

Gly Ala Phe Asn Trp Ser Ser Ile Trp Ser Gly Leu Lys Asn Phe Gly
        35                  40                  45

Ser Thr Ile Lys Ser Tyr Gly Asn Arg Ala Trp Asn Ser Ser Thr Gly
    50                  55                  60

Gln Leu Leu Arg Asp Lys Leu Lys Asp Gln Asn Phe Gln Gln Lys Val
65                  70                  75                  80

Val Asp Gly Leu Ala Ala Gly Ile Asn Gly Val Val Asp Ile Ala Asn
                85                  90                  95

Gln Ala Val Gln Arg Glu Ile Asn Asn Arg Leu Asp Pro Arg Pro Val
            100                 105                 110

Glu Glu Glu Leu Pro Ala Leu Glu Arg Gln Pro Gln Gly Glu Lys Arg
        115                 120                 125

Pro Arg Pro Asp Leu Glu Glu Thr Leu Val Thr Glu Glu Pro Pro Ser
    130                 135                 140

Tyr Glu Glu Ala Val Lys Gly Ala Pro Ser Val Ala Leu Lys Pro Val
145                 150                 155                 160

Thr Tyr Pro Leu Thr Lys Pro Ile Met Ser Met Ala Thr Pro Val Gly
                165                 170                 175

Asp Ala Pro Met Val Val Asp Leu Pro Pro Pro Ala Gly Met Thr
            180                 185                 190

Thr Pro Thr Val Pro Val Pro Ile Ala Pro Val Ser Arg Pro Ala
        195                 200                 205

Ile Arg Pro Val Ala Val Ala Thr Pro Arg Tyr Thr Arg Thr Asn Asn
    210                 215                 220

Trp Gln Asn Thr Leu Asn Ser Ile Val Gly Leu Gly Val Lys Thr Leu
225                 230                 235                 240
```

```
Lys Arg Arg Arg Cys Tyr Tyr
                245

<210> SEQ ID NO 37
<211> LENGTH: 340
<212> TYPE: PRT
<213> ORGANISM: Artificial Sequence
<220> FEATURE:
<223> OTHER INFORMATION: Synthetic polypeptide

<400> SEQUENCE: 37

Met Thr Lys Arg Lys Phe Lys Glu Glu Leu Leu Gln Ala Ile Ala Pro
1               5                   10                  15

Glu Ile Tyr Ala Pro Leu Thr Asp Pro Asp Val Lys Pro Asp Val Lys
                20                  25                  30

Pro Arg Arg Leu Lys Arg Val Lys Lys Gln Glu Thr Lys Lys Glu Glu
            35                  40                  45

Ala Leu Asp Thr Glu Gly Val Glu Phe Val Arg Ser Phe Ala Pro Arg
    50                  55                  60

Arg Arg Val Gln Trp Lys Gly Arg Arg Val Arg Arg Leu Leu Arg Pro
65                  70                  75                  80

Gly Thr Ala Val Val Phe Thr Pro Gly Glu Arg Ser Ser Arg Thr Tyr
                85                  90                  95

Lys Arg Ser Tyr Asp Glu Val Tyr Ala Asp Glu Asp Ile Leu Glu Gln
                100                 105                 110

Ala Leu Glu Gln Ser Gly Glu Phe Ala Tyr Gly Lys Arg Ala Arg Asn
            115                 120                 125

Glu Val Ala Leu Pro Leu Asp Glu Ser Asn Pro Thr Pro Ser Leu Lys
130                 135                 140

Pro Val Thr Leu Gln Val Leu Pro Val Gln Ser Thr Gly Glu Ser
145                 150                 155                 160

Lys Arg Gly Ile Lys Arg Glu Ala Val Glu Leu Gln Pro Thr Met Gln
                165                 170                 175

Leu Met Val Pro Lys Arg Gln Lys Leu Glu Asp Val Leu Asp Leu Met
            180                 185                 190

Thr Val Asp Pro Ser Val Gln Pro Asp Val Lys Ile Arg Pro Ile Lys
        195                 200                 205

Glu Val Ala Pro Gly Leu Gly Val Gln Thr Val Asp Ile Gln Ile Pro
    210                 215                 220

Val Glu Ser Met Asp Val Glu Lys Pro Lys Pro Thr Ala Val Asp Met
225                 230                 235                 240

Ala Val Gln Thr Asp Pro Trp Ala Gly Ala Pro Val Arg Ala Ala Ser
                245                 250                 255

Ala Ile Arg Asn Arg Arg Tyr Gly Pro Ala Ser Ser Leu Met Pro
                260                 265                 270

Asp Tyr Ala Leu His Pro Ser Ile Ile Pro Thr Pro Gly Tyr Arg Gly
            275                 280                 285

Gln Val Phe Arg Arg Arg Tyr Ser Ala Pro Ala Arg Arg Ser Thr Arg
        290                 295                 300

Arg Arg Arg Arg Arg Thr Thr Leu Pro Val Arg Val Arg Arg Val
305                 310                 315                 320

Thr Thr Arg Gly Arg Thr Leu Thr Leu Pro Thr Val Arg Tyr His
                325                 330                 335

Pro Thr Ile Val
            340
```

```
<210> SEQ ID NO 38
<211> LENGTH: 75
<212> TYPE: PRT
<213> ORGANISM: Artificial Sequence
<220> FEATURE:
<223> OTHER INFORMATION: Synthetic polypeptide

<400> SEQUENCE: 38

Met Ala Leu Thr Cys Arg Leu Arg Ile Pro Val Pro Gly Tyr Arg Gly
1               5                   10                  15

Arg Arg Arg His Gly Lys Gly Phe Arg Gly Ser Gly Leu Thr Arg His
                20                  25                  30

Arg Arg Arg Arg Ala Val Arg Gly Arg Met Lys Gly Gly Ile Leu Pro
            35                  40                  45

Ala Leu Ile Pro Ile Ile Ala Ala Ile Gly Ala Ile Pro Gly Ile
        50                  55                  60

Ala Ser Val Ala Val Gln Ala Ser Gln Arg Gln
65                  70                  75

<210> SEQ ID NO 39
<211> LENGTH: 190
<212> TYPE: PRT
<213> ORGANISM: Artificial Sequence
<220> FEATURE:
<223> OTHER INFORMATION: Synthetic polypeptide

<400> SEQUENCE: 39

Met Ser Ile Leu Ile Ser Pro Ser Asn Asn Thr Gly Trp Gly Leu Gly
1               5                   10                  15

Val Asn Lys Met Tyr Gly Gly Ala Lys His Arg Ser Thr Gln His Pro
                20                  25                  30

Val Arg Val Arg Gly His Tyr Arg Ala Pro Trp Gly Ala Tyr Lys Arg
            35                  40                  45

Asn Arg Arg Val Ala Glu Arg Thr Thr Val Asp Asp Val Ile Asp Ser
        50                  55                  60

Val Val Ala Asp Ala Arg Asn Tyr Val Pro Pro Ala Val Pro Ala Ala
65                  70                  75                  80

Ala Ala Ser Thr Val Asp Ala Val Ile Asp Ser Val Val Ala Asp Ala
                85                  90                  95

Arg Ala Tyr Ala Arg Gln Lys Arg Arg Gln Arg Arg Ala Arg Arg Ser
            100                 105                 110

Leu Ala Arg Pro Thr Ala Ala Met Arg Ala Ala Arg Asn Leu Leu Arg
        115                 120                 125

Arg Ala Arg Arg Thr Ser Thr Arg Ala Met Ala Arg Gln Ile Arg Ala
    130                 135                 140

Gly Arg Thr Arg Arg Ala Ala Gln Gln Ala Ala Ala Ile Ala
145                 150                 155                 160

Ser Leu Ala Ala Pro Arg Arg Gly Asn Val Tyr Trp Val Arg Asp Ala
                165                 170                 175

Ser Gly Val Arg Val Pro Val Arg Thr Arg Pro Ala Arg Val
            180                 185                 190

<210> SEQ ID NO 40
<211> LENGTH: 485
<212> TYPE: PRT
<213> ORGANISM: Artificial Sequence
<220> FEATURE:
<223> OTHER INFORMATION: Synthetic polypeptide

<400> SEQUENCE: 40
```

-continued

```
Met Leu Arg Arg Gly Ile Pro Pro Val Ala Val Ala Glu Gly Pro
1               5                   10                  15

Pro Ser Tyr Glu Ser Val Met Ala Ala Ala Leu Gln Gly Pro Leu
            20                  25                  30

Val Ala Pro Tyr Val Pro Pro Arg Tyr Leu Gly Pro Thr Glu Gly Arg
        35                  40                  45

Asn Ser Ile Arg Tyr Ser Glu Leu Ala Pro Leu Tyr Asp Thr Thr Arg
    50                  55                  60

Leu Tyr Leu Val Asp Asn Lys Ser Ala Asp Ile Ala Ser Leu Asn Tyr
65                  70                  75                  80

Gln Asn Asp His Ser Asn Phe Leu Thr Thr Val Val Gln Asn Asn Asp
                85                  90                  95

Tyr Thr Pro Ala Glu Ala Gly Thr Gln Thr Ile Asn Phe Asp Asp Arg
            100                 105                 110

Ser Arg Trp Gly Gly Glu Met Lys Thr Ile Leu His Thr Asn Met Pro
        115                 120                 125

Asn Ile Asn Ala Tyr Met Phe Thr Asn Lys Phe Arg Ala Lys Leu Met
    130                 135                 140

Thr Ala His Glu Thr Asp Lys Asp Pro Val Tyr Glu Trp Val Asp Leu
145                 150                 155                 160

Val Leu Pro Glu Gly Asn Phe Ser Glu Thr Met Thr Ile Asp Leu Met
                165                 170                 175

Asn Asn Ala Ile Val Asp His Tyr Leu Leu Val Gly Arg Gln Asn Gly
            180                 185                 190

Val Lys Glu Ser Glu Ile Gly Val Lys Phe Asp Thr Arg Asn Phe Arg
        195                 200                 205

Leu Gly Trp Asp Pro Glu Thr Gln Leu Val Met Pro Gly Val Tyr Thr
210                 215                 220

Asn Glu Ala Phe His Pro Asp Ile Val Leu Leu Pro Gly Cys Gly Val
225                 230                 235                 240

Asp Phe Thr Asn Ser Arg Leu Asn Asn Leu Leu Gly Ile Arg Lys Arg
                245                 250                 255

Gln Pro Phe Gln Glu Gly Phe Gln Ile Leu Tyr Glu Asp Leu Val Gly
            260                 265                 270

Gly Asn Ile Pro Ala Leu Leu Asp Val Thr Ala Tyr Glu Asn Ser Thr
        275                 280                 285

Pro Gly Gln Pro Pro Thr Ile Gln Pro Val Thr Glu Asp Ala Lys Asn
290                 295                 300

Arg Ser Tyr Asn Val Leu Pro Gly Thr Asn Asn Thr Ala Tyr Arg Ser
305                 310                 315                 320

Trp Tyr Leu Ala Tyr Asn Tyr Gly Asp Asp Thr Gly Ile Arg Ser Ser
                325                 330                 335

Thr Leu Leu Thr Ala Pro Asp Val Thr Cys Gly Ser Glu Gln Ile Tyr
            340                 345                 350

Trp Ser Met Pro Asp Met Met Gln Asp Pro Val Thr Phe Arg Ser Ser
        355                 360                 365

Gln Gln Thr Ser Asn Leu Pro Val Val Gly Thr Glu Leu Leu Pro Met
370                 375                 380

Tyr Ala Lys Ser Phe Tyr Asn Asp Gln Ala Val Tyr Ser Gln Leu Ile
385                 390                 395                 400

Arg Gln Ser Thr Ala Leu Thr His Val Phe Asn Arg Phe Pro Glu Asn
                405                 410                 415

Gln Ile Leu Val Arg Pro Pro Ala Pro Thr Ile Thr Thr Val Ser Glu
            420                 425                 430
```

```
Asn Val Pro Ala Leu Thr Asp His Gly Thr Leu Pro Leu Gln Asn Ser
        435                 440                 445

Ile Arg Gly Val Gln Arg Val Thr Ile Thr Asp Ala Arg Arg Thr
    450                 455                 460

Cys Pro Tyr Val Tyr Lys Ala Leu Gly Val Val Ala Pro Lys Val Leu
465                 470                 475                 480

Ser Ser Arg Thr Phe
                485

<210> SEQ ID NO 41
<211> LENGTH: 632
<212> TYPE: PRT
<213> ORGANISM: Artificial Sequence
<220> FEATURE:
<223> OTHER INFORMATION: Synthetic polypeptide

<400> SEQUENCE: 41

Met Ala Leu Ser Val Gln Asp Cys Ala Arg Leu Thr Gly Gln Ser Val
1               5                   10                  15

Pro Thr Val Asp Phe Phe Leu Pro Leu Arg Asn Ile Trp Asn Arg Val
                20                  25                  30

Gln Glu Phe Thr Arg Ala Ala Thr Thr Val Ala Gly Ile Ser Trp Met
            35                  40                  45

Ser Arg Tyr Leu Tyr Gly Tyr His Arg Leu Met Leu Glu Asp Leu Ser
    50                  55                  60

Pro Asn Ala Pro Ala Thr Arg Gly Trp Pro Leu Phe Arg Leu Pro Pro
65                  70                  75                  80

Pro His Leu Leu Val Gly Tyr Gln Tyr Leu Val Arg Thr Cys Asn Asp
                85                  90                  95

Tyr Val Phe Glu Thr Arg Ala Tyr Ser Arg Leu Lys Tyr Arg Glu Thr
                100                 105                 110

Leu Gln Pro Gly His Gln Thr Val Asn Trp Ser Val Met Ala Asn Cys
            115                 120                 125

Thr Tyr Thr Ile Asn Thr Gly Ala Tyr His Arg Phe Val Asp Leu Asp
    130                 135                 140

Asp Phe Gln Asn Thr Leu Thr Gln Ile Gln Gln Ala Ile Leu Met Glu
145                 150                 155                 160

Arg Val Val Ala Asp Leu Ala Leu Leu Glu Pro Phe Arg Gly Phe Gly
                165                 170                 175

Ala Thr Arg Met Asp Asp Arg Glu Val Ser Val Glu Thr Leu Met Gln
            180                 185                 190

Asp Tyr Tyr Lys Asp Leu Arg Arg Cys Gln Gly Glu Ala Trp Gly Met
    195                 200                 205

Ala Asp Arg Leu Arg Ile Gln Gln Ala Gly Pro Lys Asp Val Val Leu
210                 215                 220

Leu Ser Thr Ile Arg Arg Leu Lys Ser Ala Phe Phe Asn Phe Ile Ile
225                 230                 235                 240

Ser Ser Ala Val Ser Pro Glu Leu Pro Pro Glu Ala Val Leu Ser Leu
                245                 250                 255

Pro Cys Asp Cys Asp Trp Ile Asp Ala Phe Leu Gln Arg Phe Ala Asp
            260                 265                 270

Pro Val Asp Leu Thr Met Leu Arg Thr Leu Arg Gly Leu Ser Val Gln
    275                 280                 285

Thr Leu Ile Lys Cys Ile Val Ser Ala Ile Ser Leu Pro Asn Thr Pro
290                 295                 300
```

Arg Gln Ala Asn Leu Leu Gln Gly Ser Gly Leu Arg Gly Gly Val Phe
305                 310                 315                 320

Glu Leu Arg Pro Arg Glu Asp Gly Arg Ala Val Thr Glu Thr Met Arg
            325                 330                 335

Arg Arg Arg Gly Glu Met Ile Glu Arg Phe Val Asp Arg Leu Pro Ile
        340                 345                 350

Arg Arg Arg Arg Arg Val Pro Val Glu Val Glu Ala Pro Val Met
    355                 360                 365

Glu Ala Glu Glu Glu Glu Val Pro Pro Arg Thr Phe Glu Glu Glu
    370                 375                 380

Val Arg Ala Thr Val Ala Asp Leu Ile Arg Leu Glu Glu Glu Leu
385                 390                 395                 400

Thr Val Ser Ala Arg Asn Ser Gln Phe Phe Asn Phe Ala Ile Asp Phe
                405                 410                 415

Tyr Glu Ala Met Glu Arg Leu Glu Ala Val Gly Asp Ile Asn Glu Ser
            420                 425                 430

Thr Leu Arg Arg Trp Ile Met Tyr Phe Val Thr Glu His Ile Ala
        435                 440                 445

Thr Thr Leu Asn Tyr Leu Phe Gln Arg Leu Arg Asn Tyr Pro Val Phe
    450                 455                 460

Ser Arg His Val Glu Leu Asn Leu Ala Gln Val Val Met Arg Ala Arg
465                 470                 475                 480

Asp Asp Asp Gly Ala Val Val Tyr Ser Arg Val Trp Asn Glu Asn Gly
                485                 490                 495

Leu Gly Ala Phe Ser Gln Leu Ile Gly Arg Ile Ser Asn Asp Leu Ala
            500                 505                 510

Ala Thr Val Glu Arg Ala Gly Arg Gly Glu Leu Gln Glu Glu Glu Ile
        515                 520                 525

Asp Gln Leu Met Thr Glu Ile Ala Phe Gln Asp Asn Ser Gly Asp Val
    530                 535                 540

His Glu Ile Leu Arg Gln Ala Ala Ile Asn Asp Ala Asp Ile Asp Ser
545                 550                 555                 560

Val Glu Leu Ser Phe Arg Phe Lys Val Thr Gly Pro Val Val Phe Thr
                565                 570                 575

Gln Arg Gln Arg Ile Gln Asn Met Asn Arg Arg Val Val Ala His Ala
            580                 585                 590

Ser Arg Leu Arg Ser Gln His Leu Pro Leu Pro Glu Ser His Ala Asp
        595                 600                 605

Val Asp Leu Pro Val Leu Pro Ala Gly Ala Glu Pro Pro Leu Pro Pro
    610                 615                 620

Gly Ala Arg Pro Arg Arg Arg His
625                 630

<210> SEQ ID NO 42
<211> LENGTH: 1186
<212> TYPE: PRT
<213> ORGANISM: Artificial Sequence
<220> FEATURE:
<223> OTHER INFORMATION: Synthetic polypeptide

<400> SEQUENCE: 42

Met Ala Leu Phe Gln Val Gln Ser Asn Arg Thr Ser Gly Val Tyr Thr
1               5                   10                  15

Ala Ser Thr His Thr Glu His Glu Ser Pro Ser Gly Gly Ser Cys Gln
            20                  25                  30

Pro Ala Glu Val Pro Ala Pro Thr Val Ala Arg Val Ser Arg Arg Arg

```
                35                  40                  45
Arg Ser Pro Ser Thr Ala Arg Arg Arg Ala Ser Pro Ala Pro Arg
 50                  55                  60
Arg Pro Thr Pro Ser Pro Thr Leu Lys Lys Ser Leu Arg Gly Thr Val
 65                  70                  75                  80
Val Ala Ser Arg Ala His Gly Leu Ile His Ala Ile Asp Thr Arg Asp
                 85                  90                  95
His Ser Pro Val Glu Leu Lys Tyr His Leu His Leu Leu Pro Ala Leu
                100                 105                 110
Gln Arg Leu Phe Glu Ile His Leu Leu Arg Phe Pro Ala Asp Leu Cys
                115                 120                 125
Thr Leu Pro Asp Thr Cys Gly Thr Asn Asp Val Gln Arg Leu Val Ala
                130                 135                 140
Arg Leu Arg Pro Ser Phe Ala Glu Ile Trp Thr Cys Ile Ser Arg Gly
145                 150                 155                 160
Ala Val Lys Val Ala Val Leu Pro Thr Asp Gly Gln Asn Gln Ser Thr
                165                 170                 175
Thr Asp Glu Ser Lys Gln Pro Gln Pro Asn Ser Pro Ser Arg Val Pro
                180                 185                 190
Leu Pro Phe Pro Leu Arg Phe Leu Ile Arg Gly Arg Lys Ala Tyr Leu
                195                 200                 205
Ile Gln Asp Val Thr Pro Met Gln Arg Cys Glu Tyr Cys Ala Arg Phe
                210                 215                 220
Tyr Lys His Gln His Gln Cys Thr Ala Arg Arg Arg Asp Phe Tyr Phe
225                 230                 235                 240
His His Val Ala Val Gln Ser Ser Gln Trp Trp Arg Gln Ile Gln Phe
                245                 250                 255
Phe Pro Ile Gly Ser His Pro Ala Val Gln Arg Leu Phe Val Thr Tyr
                260                 265                 270
Asp Val Glu Thr Tyr Thr Trp Met Gly Ser Phe Gly Lys Gln Leu Val
                275                 280                 285
Pro Phe Met Leu Val Met Lys Phe Thr Gly Gln Ala Gln Leu Val Lys
                290                 295                 300
Thr Ala Val Asn Leu Ala Val Glu Leu Gln Trp Asn Arg Trp His Ala
305                 310                 315                 320
Asp Pro Thr Thr Phe Tyr Leu Ile Thr Pro Glu Lys Met Val Ile Gly
                325                 330                 335
Lys Gln Phe Arg Cys Phe Arg Asp Lys Leu Gln Ser Val Leu Cys Asp
                340                 345                 350
His Met Trp Asn Thr Phe Ala Asp Glu Asn Pro His Leu Thr Phe Trp
                355                 360                 365
Cys Gln Gln Thr Leu Gly Leu Cys Asp Pro Lys Glu Leu Thr Tyr Asp
370                 375                 380
Gln Leu Val Ala Ala Pro Glu Leu Arg Gly Ser Pro Gln Phe Leu Glu
385                 390                 395                 400
Leu Tyr Ile Val Gly His Asn Ile Asn Gly Phe Asp Glu Ile Val Leu
                405                 410                 415
Ala Ala Gln Val Ile Asp Asn Arg Thr Asp Val Pro Ala Pro Phe Lys
                420                 425                 430
Ile Ser Arg Asn Phe Ile Pro Arg Ala Gly Lys Ile Leu Phe Asn Asp
                435                 440                 445
Val Thr Leu Ser Leu Pro Asn Pro Lys Tyr Lys Gln Arg Lys Asp Phe
                450                 455                 460
```

```
Thr Leu Trp Glu Gln Gly Asn Cys Asp Asp Ser Asp Phe Lys Asn Gln
465                 470                 475                 480

Phe Leu Lys Val Met Val Arg Asp Thr Phe Gln Leu Thr His Thr Ser
                485                 490                 495

Leu Arg Lys Ala Ala Gln Ala Tyr Ala Leu Pro Val Glu Lys Gly Cys
            500                 505                 510

Cys Pro Tyr Arg Ala Val Asn Glu Phe Tyr Met Leu Gly Ser Tyr Gln
        515                 520                 525

Ala Thr Ala Asp Gly Phe Pro Leu Arg Asn Tyr Trp Lys Asp Glu Ala
    530                 535                 540

Glu Tyr Leu Leu Asn Arg Glu Leu Trp Lys Thr Lys Asn Lys Pro His
545                 550                 555                 560

Tyr Asn Leu Ile Glu Glu Thr Leu Glu Tyr Cys Ala Leu Asp Val Ile
                565                 570                 575

Val Thr Ala Ala Leu Val Asp Lys Leu Phe Ser Ser Tyr Ala Gln Phe
            580                 585                 590

Ile Arg Glu Thr Val Gly Tyr Ser Asn Ser Cys Phe Asn Val Phe Gln
        595                 600                 605

Arg Pro Thr Ile Ser Ser Asn Ser His Ala Ile Phe Arg Gln Ile Leu
    610                 615                 620

Tyr Thr Ala Gln Arg Pro Gln Lys Thr Asn Leu Gly Pro Asn Phe Leu
625                 630                 635                 640

Ala Pro Ser His Glu Leu Tyr Asp Tyr Val Arg Ser Ile Arg Gly
                645                 650                 655

Gly Arg Cys Tyr Pro Thr Tyr Leu Gly Val Leu Thr Glu Pro Leu Tyr
            660                 665                 670

Val Tyr Asp Ile Cys Gly Met Tyr Ala Ser Ala Leu Thr His Pro Met
        675                 680                 685

Pro Trp Gly Pro Pro Leu Asn Pro Phe Glu Arg Ala Leu Ala Ala Lys
    690                 695                 700

Asn Trp Gln Asp Ala Leu Asn Ser Ser Ser Lys Ile Ser Tyr Phe Asp
705                 710                 715                 720

Arg Leu Leu Leu Pro Gly Ile Phe Thr Ile Asp Ala Asp Pro Pro Asp
                725                 730                 735

Glu Asn Leu Leu Asp Ile Leu Pro Pro Phe Cys Ser Arg Lys Gly Gly
            740                 745                 750

Arg Leu Cys Trp Thr Asn Glu Arg Leu Arg Gly Glu Val Ala Thr Ser
        755                 760                 765

Ile Asp Met Val Thr Leu His Asn Arg Gly Trp Lys Val Arg Leu Ile
    770                 775                 780

Pro Asp Glu Arg Thr Thr Val Phe Pro Gln Trp Lys Cys Val Ala Arg
785                 790                 795                 800

Glu Tyr Val Gln Leu Asn Ile Ala Ala Lys Glu Lys Ala Asp Lys Asp
                805                 810                 815

Lys Asn Gln Thr Leu Arg Ser Ile Ala Lys Leu Leu Ser Asn Ala Leu
            820                 825                 830

Tyr Gly Ser Phe Ala Thr Lys Leu Asp Asn Lys Lys Thr Val Phe Ser
        835                 840                 845

Asp Gln Leu Asp Asp Lys Thr Leu Lys Gly Ile Ala Ser Gly His Ile
    850                 855                 860

Asn Ile Lys Ser Ser Ser Phe Ile Glu Thr Asp Asn Leu Ser Ala Glu
865                 870                 875                 880

Val Leu Pro Ser Phe Gln Arg Val Tyr Ser Pro Lys Glu Leu Ala Leu
                885                 890                 895
```

Val Asp Ser Glu Pro Glu Glu Ser Asp Glu Arg Trp Asn Pro Pro
            900                 905                 910

Phe Tyr Ser Pro Pro Gln Asp Pro Gln Ser His Val Thr Tyr Thr Tyr
            915                 920                 925

Lys Pro Ile Ile Phe Leu Asp Ala Glu Glu Thr Asp Leu Cys Leu His
        930                 935                 940

Thr Leu Glu Asn Thr Asp Pro Leu Ile Asp Asn Asp Arg Tyr Pro Ser
945                 950                 955                 960

Gln Ile Ala Ser Phe Val Leu Ala Trp Thr Arg Ala Phe Val Ser Glu
                965                 970                 975

Trp Ser Glu Phe Leu Tyr Glu Glu Asp Arg Gly Thr Pro Leu Ser Glu
            980                 985                 990

Arg Pro Leu Lys Ser Val Tyr Gly Asp Thr Asp Ser Leu Phe Val Thr
            995                 1000                1005

Asp Leu Gly His Gln Leu Met Glu Thr Lys Gly Arg Lys Arg Ile
        1010                1015                1020

Lys Lys Asn Gly Gly Arg Leu Val Phe Asp Pro Ser His Pro Glu
    1025                1030                1035

Leu Thr Trp Leu Val Glu Cys Glu Thr Val Cys Glu Lys Cys Gly
        1040                1045                1050

Ala Asp Ala Tyr Ala Pro Glu Ser Val Phe Leu Ala Pro Lys Leu
        1055                1060                1065

Tyr Ala Leu Gln Cys Leu Tyr Cys Pro Arg Cys Gly His Val Ser
        1070                1075                1080

Lys Gly Lys Leu Arg Ala Lys Gly His Ala Ala Glu Ser Leu Ser
    1085                1090                1095

Tyr Asp Leu Leu Val Lys Cys Tyr Leu Ala Asp Tyr Gln Gly Gly
        1100                1105                1110

Asn Glu Gln Phe Ser Thr Ser Arg Met Ser Leu Lys Arg Thr Leu
    1115                1120                1125

Ala Ser Ala Gln Pro Gly Ala His Pro Phe Thr Val Thr Glu Thr
    1130                1135                1140

Thr Leu Thr Arg Thr Leu Arg Pro Trp Lys Asp Met Thr Leu Thr
    1145                1150                1155

Pro Leu Asp Ala His Arg Leu Val Pro Tyr Ser Asn Ser Gln Pro
    1160                1165                1170

Asn Pro Arg Asn Gln Glu Ile Tyr Trp Ile Glu Met Pro
    1175                1180                1185

<210> SEQ ID NO 43
<211> LENGTH: 582
<212> TYPE: PRT
<213> ORGANISM: Artificial Sequence
<220> FEATURE:
<223> OTHER INFORMATION: Synthetic polypeptide

<400> SEQUENCE: 43

Met Gln Arg Pro Ala Ala Met Ala Ser Thr Glu Thr Glu Pro Met Asp
1               5                   10                  15

Pro Val Val Arg Ala Ala Leu Gln Ser Gln Pro Ser Gly Val Ala Pro
            20                  25                  30

Ser Asp Asp Trp Ser Ala Ala Met Asp Arg Ile Met Ala Leu Thr Ala
        35                  40                  45

Arg Asn Ser Glu Ala Phe Arg Gln Gln Pro Gln Ala Asn Arg Phe Ser
    50                  55                  60

-continued

```
Ala Ile Leu Glu Ala Val Val Pro Ser Arg Pro Asn Pro Thr His Glu
 65                  70                  75                  80

Lys Val Leu Ala Ile Val Asn Ala Leu Ala Glu Asn Arg Ala Ile Arg
                 85                  90                  95

Pro Asp Glu Ala Gly Gln Ile Tyr Asn Ala Leu Leu Glu Arg Val Ala
            100                 105                 110

Arg Tyr Asn Ser Thr Asn Val Gln Ser Asn Leu Asp Arg Leu Val Thr
        115                 120                 125

Asp Val Arg Glu Ala Val Ala Gln Arg Glu Arg Phe His Lys Asp Ala
130                 135                 140

Asn Leu Gly Ser Met Val Ala Leu Asn Ala Phe Leu Ser Ser Leu Pro
145                 150                 155                 160

Ala Asn Val Pro Arg Gly Gln Glu Asp Tyr Thr Asn Phe Ile Ser Ala
                165                 170                 175

Leu Arg Leu Met Val Ala Glu Val Pro Gln Ser Glu Val Tyr Met Ser
            180                 185                 190

Gly Pro Ser Tyr Tyr Phe Gln Thr Ser Arg Gln Gly Leu Gln Thr Val
        195                 200                 205

Asn Leu Ser Gln Ala Phe Lys Asn Leu Glu Gly Leu Trp Gly Val Lys
210                 215                 220

Ala Pro Leu Gly Asp Arg Ala Thr Val Ser Ser Leu Leu Thr Pro Asn
225                 230                 235                 240

Thr Arg Leu Leu Leu Leu Leu Ile Ala Pro Phe Thr Asp Ser Gly Ser
                245                 250                 255

Ile Ser Arg Asp Ser Tyr Leu Gly His Leu Ile Thr Leu Tyr Arg Glu
            260                 265                 270

Ala Ile Gly Gln Ser Arg Val Asp Glu His Thr Tyr Gln Glu Ile Thr
        275                 280                 285

Asp Val Ser Arg Ala Met Gly Gln Glu Asp Thr Ser Ser Leu Gln Ala
290                 295                 300

Thr Leu Asn Tyr Leu Leu Thr Asn Arg Arg Gln Arg Ile Pro Pro Gln
305                 310                 315                 320

Phe Ser Leu Ser Pro Glu Glu Glu Arg Ile Leu Arg Tyr Val Gln Gln
                325                 330                 335

Ser Val Ser Leu Tyr Leu Met Arg Glu Gly Asp Gly Pro Ser Ala Ala
            340                 345                 350

Leu Asp Leu Thr Ala Arg Asn Met Glu Pro Gly Leu Tyr Ser Thr Asn
        355                 360                 365

Arg Ala Phe Ile Asn Arg Leu Met Asp Tyr Leu His Arg Ala Ala Ala
370                 375                 380

Leu Asn Pro Glu Tyr Phe Asn Asn Ala Val Leu Asn Pro His Trp Leu
385                 390                 395                 400

Pro Pro Pro Gly Phe Tyr Thr Gly Glu Phe Asp Leu Pro Glu Ala Asn
                405                 410                 415

Asp Gly Phe Ile Trp Asp Asp Thr Ser Val Phe Ser Pro Met Gln
            420                 425                 430

Lys Lys Glu Gly Gly Asp Ala Gln Ser Gln Arg Val Ser Leu Ala Ser
        435                 440                 445

Met Gly Ala Ser Val Ala Ser Pro Leu Pro Ser Phe Ser Ser Ala Ser
450                 455                 460

Ser Ala Ala Gly Arg Val Asn Arg Pro Arg Leu Ser Gly Glu Thr Asp
465                 470                 475                 480

Tyr Leu Asn Asp Pro Leu Met Arg Pro Ala Arg Ala Lys Asn Phe Pro
                485                 490                 495
```

Asn Asn Gly Ile Glu Ser Leu Val Asp Lys Met Ser Arg Trp Lys Thr
500                     505                     510

Tyr Ala Gln Glu Gln Arg Glu Trp Glu Glu Gln Gln Pro Arg Pro Leu
        515                     520                     525

Ile Pro Pro Thr Arg Gly Asn Arg Arg Arg Gln Asp Met Gly Pro
530                     535                     540

Tyr Arg Val Pro Val Asp Pro Glu Asp Ser Ala Asp Asp Ser Ser Val
545                     550                     555                     560

Leu Asp Leu Gly Gly Ser Gly Asn Pro Phe Ala His Leu Arg Pro Gln
                565                     570                     575

Gly Arg Ile Gly Lys Trp
                580

<210> SEQ ID NO 44
<211> LENGTH: 375
<212> TYPE: PRT
<213> ORGANISM: Artificial Sequence
<220> FEATURE:
<223> OTHER INFORMATION: Synthetic polypeptide

<400> SEQUENCE: 44

Met His Pro Val Leu Arg Gln Met Arg Pro Ser Asn Ser Gly Pro Ala
1               5                       10                      15

Thr Thr Ala Ala Gly Ala Val Cys Gln Ala Gly Ala Gly Asn Pro Leu
                20                      25                      30

Glu Glu Val Leu Asp Ile Glu Glu Gly Glu Gly Leu Ala Arg Leu Gly
            35                      40                      45

Ala His Ser Pro Glu Arg His Pro Arg Val Gln Leu Lys Lys Asp Ser
        50                      55                      60

Ser Glu Ala Tyr Ile Pro Pro Arg Asn Leu Phe Arg Glu Arg Ser Gly
65                      70                      75                      80

Glu Glu Ala Glu Glu Met Arg Asp Ser Arg Phe Arg Ala Gly Arg Glu
                85                      90                      95

Leu Lys Lys Gly Leu Asp Arg Glu Arg Leu Leu Arg Pro Glu Asp Phe
                100                     105                     110

Glu Ala Arg Asp Arg Thr Gly Val Ser Ala Ala Arg Ala His Val Ala
            115                     120                     125

Ala Ala Asp Leu Val Thr Ala Tyr Glu Gln Thr Val Lys Glu Glu Met
        130                     135                     140

Asn Phe Gln Lys Ser Phe Asn Asn His Val Arg Thr Leu Ile Ala Arg
145                     150                     155                     160

Glu Glu Val Ala Ile Gly Leu Met His Leu Trp Asp Phe Leu Glu Ala
                165                     170                     175

Tyr Val Gln Asn Pro Thr Ser Lys Pro Leu Thr Ala Gln Leu Phe Leu
                180                     185                     190

Ile Val Gln His Ser Arg Asp Asn Glu Thr Phe Arg Asp Ala Leu Leu
            195                     200                     205

Asn Ile Ala Glu Pro Glu Gly Arg Trp Leu Leu Asp Leu Ile Asn Ile
        210                     215                     220

Leu Gln Ser Ile Val Val Gln Glu Arg Ser Leu Ser Leu Ala Asp Lys
225                     230                     235                     240

Val Ala Ala Ile Asn Tyr Ser Met Leu Ser Leu Gly Lys Phe Tyr Ala
                245                     250                     255

Arg Lys Ile Tyr Lys Thr Pro Val Pro Ile Asp Lys Glu Val Lys
                260                     265                     270

```
Ile Asp Ser Phe Tyr Met Arg Met Ala Leu Lys Val Leu Thr Leu Ser
            275                 280                 285

Asp Asp Leu Gly Ile Tyr Arg Asn Asp Arg Ile His Lys Ala Val Ser
290                 295                 300

Ala Ser Arg Arg Glu Leu Ser Asp Arg Glu Leu Met Tyr Ser Leu
305                 310                 315                 320

Gln Arg Ala Leu Thr Gly Thr His Gly Gln Asp Glu Asn Leu Phe
            325                 330                 335

Asp Ala Gly Ala Asp Leu Lys Trp Gln Pro Ser Arg Ala Trp Gln
            340                 345                 350

Ala Ala Gly Thr Tyr Leu Glu Ser Ile Glu Glu Asp Glu Asp
            355                 360                 365

Pro Glu Asn Glu Pro Ile Asp
    370                 375

<210> SEQ ID NO 45
<211> LENGTH: 475
<212> TYPE: PRT
<213> ORGANISM: Artificial Sequence
<220> FEATURE:
<223> OTHER INFORMATION: Synthetic polypeptide

<400> SEQUENCE: 45

Arg Thr Arg Leu Gln Arg Lys Thr Ser Ser Gln Gly Ser Arg Gly Arg
1               5                   10                  15

Val Pro Gln Leu Arg Pro Phe Ser Glu Met Leu Pro Cys Arg Leu Pro
            20                  25                  30

Gly Arg Lys Arg Thr Val Leu His Glu Ser Asp Glu Phe Glu Ala His
        35                  40                  45

Pro Ser Lys Arg Pro Thr Arg Ser Thr Pro Phe His Arg Asn Gly Asp
    50                  55                  60

His Thr His Glu Asn Pro Pro Leu Glu Gly His Asp Ala Asp Thr
65              70                  75                  80

Ser Gly Arg Pro Pro Ala Gly Ser Leu Gln Gln Gln Pro Thr Gln Pro
                85                  90                  95

Lys Lys Pro Gly Asn Leu Leu Asp Arg Asp Ala Val Glu His Val Thr
            100                 105                 110

Glu Leu Trp Asp Arg Leu Gln Leu Leu Cys Gln Ser Leu Gln Asn Met
        115                 120                 125

Pro Leu Ala Glu Gly Leu Lys Pro Leu Lys Lys Phe Ala Ser Leu Gln
    130                 135                 140

Glu Leu Leu Ser Leu Gly Gly Pro Arg Leu Leu Arg Glu Leu Val Gln
145                 150                 155                 160

Glu Asn Leu His Val Gln Asp Met Met Asn Glu Val Ala Pro Leu Leu
                165                 170                 175

Ala Asp Asp Gly Ser Cys Thr Ser Leu Asn Tyr His Leu Gln Pro Val
            180                 185                 190

Ile Ala Val Ile Tyr Gly Pro Thr Gly Ser Gly Lys Ser Gln Leu Leu
        195                 200                 205

Arg Asn Leu Leu Ser Thr Gln Leu Ile Ser Pro Ala Pro Glu Thr Val
    210                 215                 220

Phe Phe Ile Ala Pro Gln Val Asp Met Ile Pro Ala Glu Ile Lys
225                 230                 235                 240

Ala Trp Glu Met Gln Ile Cys Glu Gly Asn Phe Arg Ala Gly Pro Glu
                245                 250                 255

Gly Thr Leu Val Pro Gln Ser Gly Thr Leu Lys Pro Arg Phe His Lys
```

```
                  260                 265                 270
Met Ser Tyr Asp Glu Leu Thr Gln Asp Tyr Asn Tyr Asp Val Thr Asp
            275                 280                 285

Pro Arg Asn Val Phe Ala Arg Ala Ala Val Gln Gly Pro Ile Ala Ile
            290                 295                 300

Ile Met Asp Glu Cys Met Glu Asn Leu Gly Gly His Lys Gly Ile Ser
305                 310                 315                 320

Lys Phe Phe His Ala Phe Pro Ser Lys Leu His Asp Lys Phe Pro Lys
                325                 330                 335

Cys Thr Gly Tyr Thr Val Leu Val Leu His Asn Met Asn Pro Arg
                340                 345                 350

Arg Asp Leu Gly Gly Asn Ile Ser Asn Leu Lys Ile Gln Ser Lys Leu
            355                 360                 365

His Ile Met Ser Pro Arg Met His Pro Ser Gln Leu Asn Arg Phe Ile
            370                 375                 380

Asn Thr Tyr Thr Lys Gly Leu Pro Val Ala Ile Thr Leu Leu Leu Lys
385                 390                 395                 400

Asp Ile Phe Gln His His Ala Gln Arg Asn Ser Tyr Asp Trp Ile Ile
                405                 410                 415

Tyr Asn Thr Thr Pro Glu His Glu Ala Leu Gln Trp Ser Tyr Leu His
                420                 425                 430

Pro Lys Asp Gly Leu Met Pro Met Tyr Leu Asn Ile Gln Thr His Leu
            435                 440                 445

Tyr Arg Val Met Glu Lys Ile His Lys Val Leu Asn Asp Arg Glu Arg
            450                 455                 460

Trp Ser Arg Ala Tyr His Lys Lys Asn Arg Gln
465                 470                 475

<210> SEQ ID NO 46
<211> LENGTH: 134
<212> TYPE: PRT
<213> ORGANISM: Artificial Sequence
<220> FEATURE:
<223> OTHER INFORMATION: Synthetic polypeptide

<400> SEQUENCE: 46

Met Ser Gly Thr Thr Ser Gly Ser Val Thr Phe Asp Gly Gly Val Tyr
1               5                   10                  15

Ser Pro Phe Leu Thr Ser Arg Leu Pro Asn Trp Ala Gly Val Arg Gln
                20                  25                  30

Asn Val Met Gly Ser Thr Val Glu Gly His Pro Val Leu Pro Ser Asn
            35                  40                  45

Ser Ala Ser Met Arg Tyr Ala Thr Ile Gly Ser Ser Leu Asp Thr
        50                  55                  60

Ala Ala Ala Ala Ala Ser Ala Ala Ala Ser Ala Thr Arg Val Leu
65                  70                  75                  80

Ala Ala Asp Phe Gly Leu Tyr Gly Asn Phe Thr Pro Ala Ala Val Pro
                85                  90                  95

Arg Thr Val His Asp Asp Ser Leu Leu Thr Val Leu Thr Lys Leu Asp
            100                 105                 110

Asn Leu Thr Gln Gln Leu Gly Glu Leu Ser Arg Arg Val Ala Glu Leu
        115                 120                 125

Ala Glu Glu Arg Thr Val
    130

<210> SEQ ID NO 47
```

-continued

```
<211> LENGTH: 496
<212> TYPE: PRT
<213> ORGANISM: Artificial Sequence
<220> FEATURE:
<223> OTHER INFORMATION: Synthetic polypeptide

<400> SEQUENCE: 47

Met Glu Gly Leu His Glu Gly Glu Asp Leu His Leu Leu Ala Gly
1               5                   10                  15

Ala Ala Val Ala Ala Ala Gly Ala Glu Ala Val Gly Val Gln Asp
                20                  25                  30

Arg Gly Pro Asn Ala Leu Ala Gly Arg Gly Gly Ala Gln Gly Gly
                35                  40                  45

Asp Gly Ser Pro Glu Arg Asp Leu Ser Asp Gln Glu Val Pro Ala
50                  55                  60

Ala Val Gly Pro Ile Pro Asp Pro Phe Pro Glu Leu Arg Arg His Leu
65                  70                  75                  80

Leu Arg Ser Pro Gly Arg Gly Leu Glu Glu Asp Pro Gly Glu Gly Gly
                85                  90                  95

Ser Gly Glu Gln Arg Gly Ile Lys Arg Pro Arg Glu Gly Arg Lys Val
                100                 105                 110

Glu Gly Ile Met Ser Glu Leu Thr Leu Ser Leu Met Thr Arg Lys Arg
                115                 120                 125

Thr Glu Asn Lys Trp Leu Ser Glu Ile Trp Asp Glu Phe Arg Thr Gly
130                 135                 140

Asp Met Tyr Leu Gln Thr Lys Tyr Thr Phe Glu Gln Val Phe Thr Lys
145                 150                 155                 160

Trp Leu Asn Pro Glu Asp Asp Trp Glu Asp Ala Leu Thr Arg Tyr Gly
                165                 170                 175

Lys Val Ala Leu Arg Pro Asp Thr Lys Tyr Arg Leu Thr Lys Lys Val
                180                 185                 190

Glu Leu Arg Ser Cys Ala Tyr Val Ile Gly Asn Gly Ala Gln Val Glu
                195                 200                 205

Val Asp Met Gln Glu Arg Val Ala Phe Ala Cys Asn Met Val Asn Met
210                 215                 220

Gly Pro Gly Ile Val Gly Met Gly Ile Ile Phe His Asn Val Arg
225                 230                 235                 240

Phe Tyr Gly Asp Asn Phe Asn Gly Met Val Ile Met Ala Asn Thr Thr
                245                 250                 255

Val Leu Leu His Gly Cys Tyr Phe Phe Gly Phe Asn Asn Thr Val Leu
                260                 265                 270

Glu Val Trp Gly His Ser Lys Val Arg Gly Cys Thr Phe Tyr Gly Cys
                275                 280                 285

Trp Lys Ala Ile Ala Ser Arg Pro Lys Ser Glu Ile Ser Val Lys Lys
                290                 295                 300

Cys Leu Phe Glu Arg Cys Thr Leu Gly Val Cys Val Glu Gly Lys Gly
305                 310                 315                 320

Arg Ile Phe Asn Asn Val Ala Ser Glu Asn Gly Cys Phe Ala Leu Ile
                325                 330                 335

Lys Gly Phe Ala Ala Leu Lys Tyr Asn Met Ile Cys Gly Gln Ser Pro
                340                 345                 350

Thr Glu Arg Thr Tyr Gln Met Leu Thr Cys Ala Asp Gly Asn Val His
                355                 360                 365

Leu Leu Lys Thr Val His Ile Thr Gly His Ala Lys Lys Pro Trp Pro
370                 375                 380
```

```
Leu Phe Glu His Asn Val Leu Thr Arg Cys Ser Val His Leu Gly Pro
385                 390                 395                 400

Arg Arg Gly Ile Phe Ile Pro His Gln Cys Asn Phe Ser His Thr Asn
            405                 410                 415

Val Leu Val Glu Thr Glu Ala Val Thr Arg Phe Ser Leu Thr Gly Val
        420                 425                 430

Phe Asp Met Ser Val Val Ile Tyr Lys Ile Leu Arg Tyr Glu Glu Thr
            435                 440                 445

Lys Ala Arg Cys Arg Cys Cys Glu Cys Gly Lys His Leu Arg Asn
        450                 455                 460

Gln Pro Val Ile Val Asp Val Thr Glu Glu Val Arg Met Asp His Met
465                 470                 475                 480

Gln His Ser Cys Ala Arg Ala Asp Tyr Ser Thr Asp Glu Asp Thr Glu
            485                 490                 495
```

<210> SEQ ID NO 48
<211> LENGTH: 177
<212> TYPE: PRT
<213> ORGANISM: Artificial Sequence
<220> FEATURE:
<223> OTHER INFORMATION: Synthetic polypeptide

<400> SEQUENCE: 48

```
Met Glu Leu Asp Arg Leu Leu Glu Asn Tyr Asn Ser Leu Arg Arg Val
1               5                   10                  15

Leu Glu Glu Ala Ser Glu Asp Thr Ser Val Trp Trp Arg Lys Leu Phe
            20                  25                  30

Gly Cys Arg Val Ser Gln Leu Val Gln Ala Lys Val Glu Tyr Lys
        35                  40                  45

Glu Glu Phe Glu Lys Leu Phe Ser Glu Val Pro Gly Leu Val Asp Ser
    50                  55                  60

Leu Asn Phe Cys His His Ala Phe Phe Tyr Glu Lys Val Ile Cys Gly
65                  70                  75                  80

Leu Asp Phe Cys Thr Pro Gly Arg Thr Ile Ala Ala Leu Ala Phe Cys
            85                  90                  95

Ala Phe Ile Leu Asp Lys Trp Asn Lys Glu Thr His Leu Ser Lys Gly
            100                 105                 110

Tyr Thr Leu Asp Tyr Ile Ser Leu Gln Leu Trp Lys Ala Tyr Met Arg
        115                 120                 125

Lys Gly Lys Ile Tyr Thr Phe Ser Gln Gly Pro Arg Ser Leu Pro Gln
    130                 135                 140

Arg Val Arg Arg Arg Leu Gly Phe Lys Thr Glu Asp Gln Thr Arg Leu
145                 150                 155                 160

Leu Glu Ala Glu Glu Pro Arg Ala Gly Thr Asp Pro Pro Ser Glu
            165                 170                 175

Thr
```

<210> SEQ ID NO 49
<211> LENGTH: 272
<212> TYPE: PRT
<213> ORGANISM: Artificial Sequence
<220> FEATURE:
<223> OTHER INFORMATION: Synthetic polypeptide

<400> SEQUENCE: 49

```
Met Arg Thr Pro Leu Val Glu Gly Asp Ile Pro Val Arg Phe Ala Ala
1               5                   10                  15

Glu Leu Leu Ala Ala Leu Ala Glu Glu Val Phe Ala Asp Val Glu Pro
```

```
                20                  25                  30
Pro Arg Ala Phe Glu Asp Val Ser Leu His Asp Leu Phe Asp Leu Asp
            35                  40                  45

Val Glu Asp Arg Glu Asp Pro Ser Gln Asp Ala Val Asp Met Leu Phe
 50                  55                  60

Pro Glu Ser Leu Leu Leu Ala Ala Glu Glu Gly Ile Asp Ile Pro Arg
 65                  70                  75                  80

Asp Thr Pro Pro Pro Leu Glu Pro Pro Met Val Leu Ser Pro Leu Ser
                85                  90                  95

Gln Gln Gln Gln Asp Met Pro Asp Leu Thr Val Gly Asp Val Asn Leu
            100                 105                 110

Leu Cys Ser Glu Ser Ser Phe Ser Ser Leu Glu Glu Asn Glu Leu Glu
            115                 120                 125

Arg Cys Met Ala Glu Leu Ala Ala Ser Gly Val Ala Ser Val Arg Glu
            130                 135                 140

Gln Glu Arg Glu Glu Met Ser Gly Thr Pro Phe Asn Leu Asp Tyr Pro
145                 150                 155                 160

Glu Met Pro Gly Tyr Gly Cys Lys Ser Cys Gln Tyr His Arg Glu Gln
                165                 170                 175

Thr Gly Glu Ala Asp Ile Leu Cys Ser Leu Cys Tyr Leu Arg Arg Asn
            180                 185                 190

Gly Val Phe Val Tyr Ser Pro Val Ser Glu Ala Glu Val Asp Glu Pro
            195                 200                 205

Asp Thr Thr Thr Asp Asp Gln Gly Arg Ala Gln Ser Pro Pro Lys Leu
            210                 215                 220

Thr Gln Asp Ala Pro Val Asn Val Ile Arg Pro Arg Pro Ile Arg Pro
225                 230                 235                 240

Ser Ser Arg Arg Arg Asn Ala Val Asp Ser Leu Glu Ser Leu Leu Glu
                245                 250                 255

Asp Asp Asp Cys Glu Pro Leu Asp Leu Thr Phe Lys Arg Ala Arg Tyr
            260                 265                 270

<210> SEQ ID NO 50
<211> LENGTH: 128
<212> TYPE: PRT
<213> ORGANISM: Artificial Sequence
<220> FEATURE:
<223> OTHER INFORMATION: Synthetic polypeptide

<400> SEQUENCE: 50

Met Ala Thr Asn Glu Glu Phe Leu Tyr Val Tyr Arg Glu Gly Glu His
1               5                   10                  15

Gly Ile Leu Pro Val Gln Glu Gly Tyr Ser Gly Val Tyr Thr Leu Phe
            20                  25                  30

Ser Pro Glu Asp Phe Val Ile Pro Pro Glu Gly Val Leu Leu Leu Tyr
            35                  40                  45

Leu Gln Ile Arg Val Gln Val Pro Pro Gly Tyr Ile Gly Arg Leu Gly
        50                  55                  60

Pro Leu Gly Asp Leu Val Arg Arg Gly Ile Phe Ala Gly Ala Asp Thr
 65                 70                  75                  80

Val Asp Pro Cys Thr Arg Trp Glu Leu Lys Leu Leu Leu Phe Asn His
                85                  90                  95
```

```
Thr Pro Asp Phe Tyr His Gly Gln Arg Gly Gln Ala Val Gly Arg Phe
            100                 105                 110

Leu Leu His Arg Val Ile Tyr Pro Thr Val Leu Glu Ala Thr Gln Val
        115                 120                 125
```

PRODUCTION OF RAAV IN VERO CELLS USING PARTICULAR ADENOVIRUS HELPERS

STATEMENT OF GOVERNMENT INTEREST

This invention was made with government support under N01-AI-50008 awarded by The National Institute of Allergy and Infectious Diseases (NIAID). The government has certain rights in the invention.

FIELD OF THE INVENTION

The present invention relates to methods and materials for recombinant adeno-associated virus production. More particularly, the invention contemplates the use of an adenovirus known as Simian Adenovirus 13 (SAdV-13) and Vero cells for production of infectious recombinant adeno-associated virus (rAAV).

BACKGROUND

Infectious recombinant AAV are being developed as gene transfer vehicles for an ever-widening array of human applications such as for use as vaccines and gene therapy vectors. The intense interest in rAAV has been fueled by the finding that these simple vectors can efficiently transduce a variety of post-mitotic cells when administered in vivo. Promising data from animal models has resulted in the initiation of several ongoing human clinical trials. While these advances are encouraging, obstacles remain for the general implementation of rAAV as a universal gene transfer vehicle.

Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., J. Virol., 45: 555-564 (1983) as corrected by Ruffing et al., J. Gen. Virol., 75: 3385-3392 (1994). Cis-acting sequences directing viral DNA replication (rep), encapsidation/packaging and host cell chromosome integration are contained within the ITRs. Three AAV promoters, p5, p19, and p40 (named for their relative map locations), drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (Rep 78, Rep 68, Rep 52, and Rep 40) from the rep gene. Rep 78 and Rep 68, are respectively expressed from unspliced and spliced transcripts initiating at the p5 promoter, while Rep 52 and Rep 40, are respectively expressed from unspliced and spliced transcripts initiating at the p19 promoter. Rep proteins possess multiple enzymatic properties which are ultimately responsible for replicating the viral genome. Rep 78 and 68 appear to be involved in AAV DNA replication and in regulating AAV promoters, while Rep 52 and 40 appear to be involved in formation of single-stranded AAV DNA. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

When wild type AAV infects a human cell in culture, the viral genome can integrate into chromosome 19 resulting in latent infection of the cell. Production of infectious virus does not occur unless the cell is infected with a helper virus (for example, adenovirus or herpesvirus). In the case of adenovirus, genes E1A, E1B, E2A, E4 and VA provide helper functions. Upon infection with a helper virus, the AAV provirus is rescued and amplified, and both AAV and adenovirus are produced.

AAV possesses unique features that make it attractive for delivering DNA to cells in a clinical application, for example, as a gene therapy vector or an immunization vector. AAV infection of cells in culture is noncytopathic, and natural infection of humans and other animals is silent and asymptomatic. Moreover, AAV infects many mammalian cells allowing the possibility of targeting many different tissues in vivo. The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV-vectors less critical. AAV may even be lyophilized. Finally, AAV-infected cells are not resistant to superinfection.

Production of rAAV requires the AAV rep78/68, rep52/40 and capsid genes and expression of their gene products, a DNA of interest flanked by AAV ITRs, helper functions provided by an adenovirus or herpesvirus helper virus, and a cell line comprising these components that is permissive for AAV replication. Examples of helper virus functions are adenovirus genes E1a, E1b, E2A, E4 and VA RNA [Carter, Adeno-associated virus helper functions in "Handbook of Parvoviruses" Vol I (P. Tjissen, Ed.) CRC Press, Boca Raton, pp 255-282 (1989)]. Wild type AAV (wt AAV) has one of the largest burst sizes of any virus following infection of cells with AAV and adenovirus. This may be well in excess of 100,000 particles per cell [Aitken et al., Hum Gene Therapy, 12:1907-1916 (2001)], while some rAAV production systems have been reported to achieve greater than $10^3$ particles per cell. Rep proteins are absolutely required for both wt AAV and rAAV replication and assembly of intact infectious particles, as summarized in Carter et al., AAV vectors for gene therapy, in "Gene and Cell Therapy: Therapeutic Mechanisms and Strategies", Second Edition (Ed. N. Templeton-Smith), pp 53-101, Marcel Dekker, New York (2004).

A requirement for the clinical use of recombinant AAV for DNA delivery is a highly efficient scheme for production of infectious recombinant virus that is reproducible and commercially scalable. One popular mechanism of producing rAAV is to transiently transfect cells with one or more plasmids containing adenoviral helper genes, rep and cap genes, and a recombinant AAV genome. Such transfection methods are difficult to scale up, which has lead to development of stable cell line methods.

Two types of stable cell lines have been developed. In one type (producer cells), both the rAAV genome and the rep-cap genes are stably integrated into the cell DNA, while helper functions are provided by a wild-type adenovirus. As used herein, "producer cells" are those cells that are stably transformed with a rAAV genome and AAV rep/cap genes. In the second type (packaging cells), the rep and cap genes are integrated, while the rAAV genome is provided by infection with a recombinant adenovirus or herpes virus containing the rAAV genome (termed herein a "rAd/AAV hybrid" or "rHerpes/AAV hybrid"), and the helper functions are provide by a wild type adenovirus. As used herein, "packaging cells" are those cells that are stably transformed with AAV rep/cap genes.

The most common forms of these scalable systems use HeLa cells. Other cell substrates have also been used to produce AAV. One such cell substrate is a Vero cell. See, for example, U.S. Patent Application US20040224411 published Nov. 11, 2004; Handa et al., Journal of Biological Chemistry 254(14): 6603-6610 (1979); Richardson et al., Proc Natl Acad Sci USA 77(2): 931-935 (1980); and Liu et al., Journal of Virology 80(4): 1672-1679 (2006). Vero cells are derived from African green monkey kidney cells, and were identified as a cell line substrate for viral vector production. Vero cells have been used as a cell line substrate for the production of numerous human vaccines, including poliovirus (both oral and inactivated) and rabies. The safety of the cell line is attested to by pharmacovigilance of more than 20 million doses of rabies vaccine and more than 1 billion of OPV.

Vero cells have been readily adapted for growth in bioreactors on microcarriers and provide consistently high yields of viruses such as polio and rabies viruses. This allows for vaccine purity (less contaminating cell debris), large lots of vaccine (i.e., greater vaccine availability), and more economic production of vaccine. The issues of yield and adaptability to growth in bioreactors are grounds for use of Vero cells that have been provided to the Center for Biologics Evaluation and Research (CBER) division of the FDA by most manufacturers who propose to use them for vaccine production.

There remains a need in the art for new methods for scalable high titer production of rAAV from mammalian non-transformed cancer cells.

SUMMARY OF THE INVENTION

The present invention provides methods and materials useful for producing infectious recombinant AAV (rAAV). Compared to previous methods and materials, the methods and materials of the invention allow for much higher titers of rAAV to be produced and/or allow for high titer production of rAAV in mammalian cells other than transformed cancer cells.

The present invention achieves scalable high titer rAAV production using Vero cell substrates combined with simian adenovirus 13 (SAdV-13) helper virus. A particular SAdV-13 clone provided by the invention is SAdV-13 PME-12. The sequence of the clone is set out in SEQ ID NO: 16. The invention contemplates that other helper viruses like SAdV-13 or SAdV-13-like helper plasmids may also be used in the methods of the invention. A "SAdV-13-like" helper virus or helper plasmid according to the invention may be a naturally-occurring helper virus (i.e., not made by recombinant DNA techniques), or a recombinant helper virus or recombinant helper plasmid encoding one or more helper virus functions. Techniques to make recombinant helper viruses and helper plasmids are known in the art. Helper viruses of AAV are known in the art and include, for example, viruses from the family Adenoviridae and the family Herpesviridae. In some embodiments of the invention, the "SAdV-13-like" helper virus is from the Adenoviridae family including, but not limited to, a simian or human adenovirus.

In one embodiment of the invention, an "SAdV-13-like" helper virus may be a helper virus, the use of which allows rAAV production in Vero cells at a titer about equal to, equal to, or greater than the titer obtained with SAdV-13 in the assay of Example 2.

In another embodiment of the invention, an "SAdV-13-like" helper virus may be a helper virus that induces AAV rep gene amplification in a Vero cell that is about equal to, equal to, or greater than the amplification obtained when SAdV-13 is used. Adenovirus-dependent rep gene amplification can be readily determined by qPCR as previously described [Liu et al., Mol Ther 2:394-403 (2000)].

In yet another embodiment of the invention, an "SAdV-13-like" helper virus may be a helper virus that upregulates the expression of AAV rep, or AAV rep and cap genes, in a Vero cell so that AAV rep gene expression is about equal to, equal to, or greater than that obtained when SAdV-13 is used. Rep gene expression can be measured, for example, with a Western blot assay using anti-rep monoclonal antibody (such as clone 226.7, American Research Products).

In still other embodiment, a "SAdV-13-like" helper virus according to the invention may be a helper virus that exhibits a delayed cytopathic effect (CPE) relative to other helper viruses. These may be identified by carrying out the assay in Example 3 in Vero cells and selecting those helper viruses that take "time to reach maximal CPE about that of SAdV-13" wherein SAdV-13 and the other helper viruses are used at MOI=10. A "time to reach maximal CPE about that of SAdV-13" is a period of greater than 1 day, 2 days, 3 days, 4 days, 5 days or more than the maximal CPE of human adenovirus 5 (MOI=10) in the assay. In one embodiment, the "time to reach maximal CPE about that of SAdV-13" is a period of at least 1 day more than the maximal CPE of human adenovirus 5 (MOI=10) in the assay. Alternatively, a "time to reach maximal CPE about that of SAdV-13" may be a period that is at least about 80%, 90%, 95%, 96%, 97%, 98%, 99%, 100% or greater than the time to reach maximal CPE of SAdV-13 in the assay. Other adenoviruses that are reported to have delayed cytopathic effect include human Ad-8 and -19 [Schwartz et al., Invest Opthalmol Vis Sci. 18(9):956-63 (1979)] and mouse adenovirus 1 [Nguyen et al, Gene Therapy 6, 1291-1297 (1999)].

CPE is a change in cellular morphology that occurs following viral infection. The nature of the change varies somewhat between viruses but for adenoviruses is generally recognizable by rounding of the cells and detachment from the substrate in cell culture. This causes the cell boundary to be more refractile when observed by phase contrast microscopy. Maximal CPE can be defined as a state where a vast majority of cells (i.e. >95%) display a rounded shape.

Those of skill in the art will understand that the multiplicity of infection (MOI) used in these CPE assays does not necessarily mirror what would be used in method of the invention for production of rAAV. The invention contemplates that variation in host cell, helper virus and culturing conditions may necessitate using a MOI that differs from that utilized in a CPE assay, and would not require undue experimentation by one of ordinary skill in the art to determine. The MOI to be utilized in rAAV production methods of the invention is from about 1 to about 20, or from about 1 to about 100, when a naturally-occurring adenovirus is used as the helper virus. The MOI to be utilized when recombinant adenovirus is used as the helper virus is from about 1 to about 20, about 30, about 40, about 50, or about 70.

In yet another embodiment of the invention, an "SAdV-13-like" helper virus may be a helper virus that, when used in methods of the invention, results in production of a titer of at least about: $2\times10^4$ DNAse resistant particles (DRP) per cell, $2.5\times10^4$ DRP per cell, $3\times10^4$ DRP per cell, $3.5\times10^4$ DRP per cell, $4\times10^4$ DRP per cell, $4.5\times10^4$ DRP per cell, $5\times10^4$ DRP per cell, $5.5\times10^4$ DRP per cell, $6\times10^4$ DRP per cell, $6.5\times10^4$ DRP per cell, $7\times10^4$ DRP per cell, $7.5\times10^4$ DRP per cell, $8\times10^4$ DRP per cell, $8.5\times10^4$ DRP per cell, $9\times10^4$ DRP per cell, $9.5\times10^4$ DRP per cell, $1\times10^5$ DRP per cell, $1.5\times10^5$ DRP per cell, $2\times10^5$ DRP per cell, or $2.5\times10^5$ DRP per cell.

In an embodiment, the invention provides methods for increasing rAAV production in a Vero cell line of at least 2-fold in comparison to use of human adenovirus 5 (HuAd5) helper virus and Vero cells. In other embodiments, the invention provides methods of increasing rAAV production in a Vero cell line of at least 3-fold, at least 3.5-fold, at least 4-fold, at least 4.5-fold, at least 5-fold, at least 10-fold, at least 20-fold or at least 50-fold.

In an embodiment of the invention, a method of producing rAAV is provided, comprising the steps of infecting a Vero producer cell with SAdV-13 and culturing the cell. See, for example, methods based on stable HeLa cell lines described in Clark et al., Hum. Gene Ther 6:1329-1341 (1995), and Tamayose et al., Hum Gene Ther 7:507-513 (1996).

In another embodiment of the invention, a method of producing rAAV is provided comprising the steps of introducing a rAAV genome into a Vero packaging cell, infecting the cell with SAdV-13 and culturing the cell. The rAAV genome may be introduced by a rAd/AAV hybrid. Vero packaging cell lines may be generated that express rep-cap genes upon adenovirus infection. rAAV is produced by infecting the packaging cell line with a recombinant adenovirus harboring a rAAV vector genome in the adenovirus E1 region or adenovirus E3 region (rAd/AAV hybrid). The corresponding E1 or E3 helper gene products are also provided for robust Ad/AAV hybrid replication. See, for example, Liu et al., Gene Ther. 6:293-299 (1999); Inoue et al., J Virol 72:7024-7031 (1998); Gao et al., Hum Gene Ther 9:2353-2362 (1998); Conway et al., Gene Ther 6:986-993 (1999); Vincent et al., Vaccine 90: 353-359 (1990); Clark et al., Hum Gene Ther 10:1031-1039 (1999); Thrasher et al., Gene Ther 2:481-485 (1995); Fisher et al., Hum Gene Ther 7:2079-2087 (1996); and Gao et al., Mol Ther 5:644-649 (2002). Upon co-infection, the rAAV vector is excised from the adenovirus genome, replicated, and packaged into infectious virions.

In still another embodiment of the invention, a method of producing rAAV is provided comprising the steps of introducing a rAAV genome and AAV rep/cap genes into a Vero cell, infecting the cell with SAdV-13 helper virus and culturing the cell. The introduction of the rAAV genome and AAV rep/cap genes into a Vero cell may occur concurrently with the infection of the cell with helper virus. Alternatively, the Vero cell may be a packaging cell. rAAV is commonly generated in cell culture by plasmid DNA transfection of mammalian cells. The plasmid components are: an AAV vector plasmid, an AAV rep-cap expressing plasmid, and an adenovirus helper plasmid or wild-type adenovirus infection. See, for example, Vincent et al., J Virol 71:1897-1905 (1997); Ogasawara et al., Microbiol Immunol 42:177-185 (1998); Li et al., J Virol 71:5236-5243 (1997); Grimm et al., Hum Gene Ther 9:2745-2760 (1998); Ferrari et al., J Virol 70:3227-3234 (1996); Xiao et al., J Virol 72:2224-2232 (1998); Collaco et al., Gene 238:397-405 (1999); Matsushita et al., Gene Ther 5:938-945 (1998); and Salvetti et al., Hum Gene Ther 9:695-706 (1998). The methods that may be utilized to introduce rep and cap genes into a cell are well known to those of ordinary skill in the art. These may include, e.g., use of a virus that encodes rep and/or cap genes to infect a cell, or use of a plasmid that encodes rep and/or cap genes to transiently transfect a cell.

In an embodiment of the invention, a method of producing rAAV is contemplated comprising the steps of infecting a Vero producer cell with a SAdV-13-like adenovirus helper virus and culturing the cell.

In another embodiment of the invention, a method of producing rAAV is provided comprising the steps of introducing a rAAV genome into a Vero packaging cell, infecting the cell with a SAdV-13-like adenovirus helper virus and culturing the cell. The rAAV genome may be introduced by a rAd/AAV hybrid.

In yet another embodiment of the invention, a method of producing rAAV is provided comprising the steps of introducing a rAAV genome and AAV rep/cap genes into a Vero cell, infecting the cell with a SAdV-13-like helper virus and culturing the cell. The introduction of a rAAV genome and AAV rep/cap genes into a Vero cell may occur concurrently with the infection of the cell with a SAdV-13-like helper virus. Alternatively, the Vero cell may be a packaging cell.

In embodiments of the invention, the rAAV produced by the methods of the invention is isolated.

In a further embodiment of the invention, methods are provided that comprise infecting a Vero packaging cell with helper virus of the invention and then with an Ad/AAV hybrid virus encoding the rAAV genome. In some embodiments, the Vero cell may be infected with the Ad/AAV hybrid virus about 16 to 24 hours after helper virus infection.

In yet another embodiment of the invention, a method is provided for producing infectious recombinant adeno-associated virus (rAAV), the improvement comprising infecting a Vero cell with SAdV-13 helper virus.

In still another embodiment of the invention, a method is provided for producing infectious recombinant adeno-associated virus (rAAV), the improvement comprising infecting a Vero cell with a SAdV-13-like adenovirus helper virus.

In an embodiment of the invention, a method of producing infectious rAAV is provided comprising culturing a Vero producer cell under conditions permissive for rAAV production, wherein the Vero producer cell comprises simian adenovirus 13 (SAdV-13) helper virus.

In another embodiment of the invention, a method of producing infectious rAAV is provided comprising culturing a Vero producer cell under conditions permissive for rAAV production, wherein the Vero producer cell comprises simian adenovirus 13-like (SAdV-13-like) helper virus.

Methods of the invention produce rAAV titers of at least about: $2\times10^4$ DNAse resistant particles (DRP) per cell, $2.5\times10^4$ DRP per cell $3\times10^4$ DRP per cell, $3.5\times10^4$ DRP per cell, $4\times10^4$ DRP per cell, $4.5\times10^4$ DRP per cell, $5\times10^4$ DRP per cell, $5.5\times10^4$ DRP per cell, $6\times10^4$ DRP per cell, $6.5\times10^4$ DRP per cell, $7\times10^4$ DRP per cell, $7.5\times10^4$ DRP per cell, $8\times10^4$ DRP per cell, $8.5\times10^4$ DRP per cell, $9\times10^4$ DRP per cell, $9.5\times10^4$ DRP per cell, $1\times10^5$ DRP per cell, $1.5\times10^5$ DRP per cell, $2\times10^5$ DRP per cell, or $2.5\times10^5$ DRP per cell. In methods of the invention, Vero cells are cultured under conditions permissive for rAAV production.

The invention contemplates that any rAAV serotype (including, but not limited to, AAV1, AAV2, AAV5, AAV6, AAV7, AAV8, AAV9, and variants thereof), pseudotype or chimera may be produced by methods of the invention.

The invention also contemplates that any rAAV genome that can be packaged in an infectious recombinant AAV (rAAV) may be used in the methods described herein. Numerous appropriate rAAV genomes are described in the art and may be used in the invention. rAAV genomes usually comprise one or more DNAs of interest flanked by AAV ITRs, or comprise an expression cassette (one or more DNAs of interest operatively linked to a promoter and polyadenylation signal for expression) flanked by AAV ITRs. The DNAs of interest may encode a protein or an RNA, as is understood in the art. In embodiments of the invention, there are no AAV rep and cap genes between the AAV ITRs of rAAV genomes.

The present invention provides for a Vero producer cell or Vero cell producer cell substrate (as used interchangeably herein) wherein the Vero producer cell comprises an rAAV ITR flanking a polynucleotide of therapeutic interest (rAAV genome) and AAV rep and cap genes. In some embodiment both the rAAV genome and the rep-cap genes are stably integrated into the Vero cell. In some embodiments either or both the rAAV genome and the AAV rep-cap genes are introduced into the Vero cell via infection with a recombinant adenovirus or recombinant herpes virus wherein the either the rep-cap genes or rAAV genome respectively is a stably integrated into the Vero cell.

DETAILED DESCRIPTION

Figure 1:
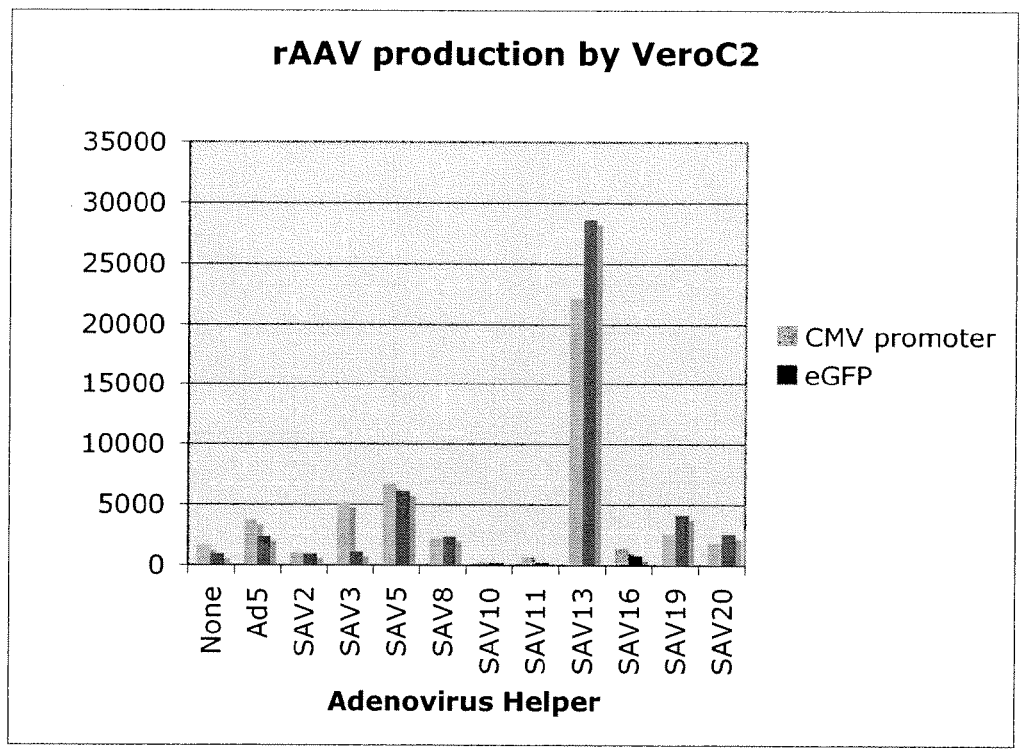
FIG. 1 depicts production of rAAV following various helper virus infections of VeroC2 cells. Cells were infected with the indicated virus at MOI=10 and rAAV DRP was quantified by DRP using qPCR. Real time PCR with primer/probe sets detecting the CMV promoter (blue) and the eGFP coding region (red) are shown.

The present invention is illustrated by the following examples relating to the production of increased titers of rAAV using a VeroC2 cell line and SAdV-13. Example 1 describes experiments in which VeroC2 cells are infected with simian adenoviruses. Example 2 describes the level of production of rAAV as measured by a DNAse-resistant particle (DRP) assay. Example 3 describes a CPE assay used to determine the maximal CPE of various adenovirus helper viruses. Example 4 describes the production of rAAV in Vero cells. Example 5 demonstrates the development of Vero lines that could be used to produce rAAV by an alternative, scalable method. Example 6 describes rAAV production using Vero packaging cells and the Ad/AAV hybrid system with SAdV-13 helper virus. Example 7 describes the cloning and sequencing of a particular SAdV-13 helper virus named SAdV-13 (PME 12). Example 8 describes the development of a qPCR assay to quantitate SAdV-13.

Example 1

The effect of use of various simian adenovirus helper viruses on rAAV expression of a heterologous gene in Vero cells was examined.

Simian adenoviruses were obtained from the American Type Culture Collection (ATCC, Manassas, Va.) and propagated by infecting LLC-MK2 cells (ATCC) in DMEM with 2% supplemented calf serum (Cosmic Calf Serum, HyClone, Logan Utah). Cleared cell lysates were prepared by four rounds of freezing and thawing followed by centrifugation to remove particulates. Virus samples were checked for the presence of wild type AAV by a PCR assay with degenerate primers as described in Chen et al., J Virol 79: 14781-14792 (2005). Viral samples that showed the presence of contaminating wild type AAV were processed by plaque purifying virus in the presence of anti-AAV1 rabbit antiserum. The PCR assay was then repeated on the new viral stocks. Viruses were titered by the $TCID_{50}$ method on LLC-MK2 cells as described in the Adeno-X expression system 1 User Manual, pages 46-47 (August 2007 version, protocol PT3414-1, version PR7823350), Clontech Laboratories, Inc. (Mountain View, Calif.).

A producer AAV cell line was derived from the standard Vero line distributed by ATCC (Cat # CCL-81) by methods generally described in U.S. Pat. No. 5,658,785. The producer cell line named VeroC2 has three elements stably integrated in the genomic DNA: (1) the rep and cap genes of AAV2; (2) a recombinant AAV genome with a green fluorescent protein (GFP) gene; and (3) the neomycin resistance gene. The cell line was plated at 20,000 cells per well in a 24 well plate. After one day the cells were infected with a panel of monkey adenoviruses. The adenovirus was used at a multiplicity of infection (MOI) of 10. The cells were examined 1-2 days later using a fluorescent microscope that detects GFP expression as a result of recombinant genome replication and transgene expression. Simian adenoviruses that were tested were SAdV-2, 3, 5, 8, 10, 11, 13, 16, 19 and 20.

Results showed highest GFP expression in VeroC2 cells infected with SAdV-13. Lower GFP expression was noted for VeroC2 cells infected with SAdV-5, -8, and -19. GFP expression was barely detectable for VeroC2 cells infected with SAdV-2, 3, 10, 11, 16 and 20.

Example 2

The effect of use of various simian adenovirus helper viruses on rAAV particle production in Vero cells was also examined.

The level of production of rAAV was measured by the DNAse-resistant particle (DRP) assay. Vero C2 cells were infected at an MOI of 10 with SAdV-2, -3, -5, -8, -10, -11, -13, -16, -19, or -20. When infected cells showed maximal cytopathic effect (CPE) (evidenced by rounding and detachment) they were harvested and subjected to 4 freeze thaw cycles to lyse the cells and release the virus. Heat treatment was used to inactivate residual Ad5 (55° C. for 30 min). The samples were then diluted 1:1,000 in 50 mM KCl, 10 mM Tris pH 8.0, 5 mM $MgCl_2$ and 50 µl of the diluted lysate was treated with DNAse I for 30 min at 37° C. The DNAse was heat inactivated at 95° C. for 10 minutes and 10 µg of Proteinase K was added and allowed to digest the rAAV capsid for 1 hr at 50° C. and then the Proteinase K was inactivated by heating at 95° C. for 20 minutes. The net effect of the two treatments is to first remove any DNA that is not packaged into viral particles, and then to degrade the viral capsid proteins and release the encapsidated viral genomes. Viral DNA was quantified by real-time qPCR using "Taqman" chemistry in a ABI 7000 real time instrument (Applied Biosystems). Two primer/probe sets were utilized, one set that detects the CMV promoter, and a second set that detects the eGFP gene. A complete list of primer/probe sets that are used in this disclosure are shown in Table 1. The probes were labeled with 6-FAM at the 5' end and TAMRA at the 3' end. The Ad5 E4 sequences used were taken from Sagawa et al., 2004, Mol. Therapy 10, 1043.

TABLE 1

| Sequence detected | Primer 1 sequence | Primer 2 sequence | Probe sequence |
|---|---|---|---|
| CMV-IE promoter | TGGAAATCCCCGT GAGTCAA SEQ ID NO 1 | CATGGTGATGCGG TTTTGG SEQ ID NO 2 | CCGCTATCCACGCCCA TTGATG SEQ ID NO 3 |
| eGFP | CCACTACCTGAGC ACCCAGTC SEQ ID NO 4 | TCCAGCAGGACCA TGTGATC SEQ ID NO 5 | TGAGCAAAGACCCCAA CGAGAAGCG SEQ ID NO 6 |
| Beta gal | TGGCTGGAGTGCG ATCTTC SEQ ID NO 7 | CGTGCATCTGCCA GTTTGA SEQ ID NO 8 | TGAGGCCGATACTGTC GTCGTCCC SEQ ID NO 9 |
| Ad5E4 | GGAGTGGAGCCGA GACAAC SEQ ID NO 10 | ACTACGTCCGGCG TTCCAT SEQ ID NO 11 | TGGCATGACACTACGA CCAACACGATCT SEQ ID NO 12 |

By comparing the results for unknown samples with a standard curve generated with known quantities of plasmid DNA, the number of copies of a sequence in the sample were determined. The numbers were converted to the numbers of rAAV genomes produced per cell (FIG. 1).

The overall results indicated that SAdV-13 was the best helper virus tested. Importantly, using SAdV-13 as the helper levels of rAAV per cell were generated that were comparable to levels attainable with HeLa-based lines. Although vector yields depend on a number of factors, the highest producing HeLa lines for any given construct tend to produce $10^4$-$10^5$ particles per cell.

Example 3

The CPE of various helper viruses was examined.

The time to reach maximum CPE was examined for various viruses by infecting cells at MOI 10, then examining their morphology daily by phase contrast microscopy with an inverted microscope. The time to maximal CPE was defined as the first day at which at least 95% of the cells show definite rounding.

For simian adenoviruses 1, 2, 3, 5, 7, 8, 10, 11, 16, 19, and 20 on Vero cells, the time to maximal CPE was 2-3 days. For HuAd5 on Vero cells the time to maximal CPE was 3-4 days, while for HuAd5 on HeLa cells it was 2 days. For SAdV-13 on Vero cells the time to maximal CPE was 5 days.

Example 4

Recombinant AAV was produced in Vero cells.

Figure 2:
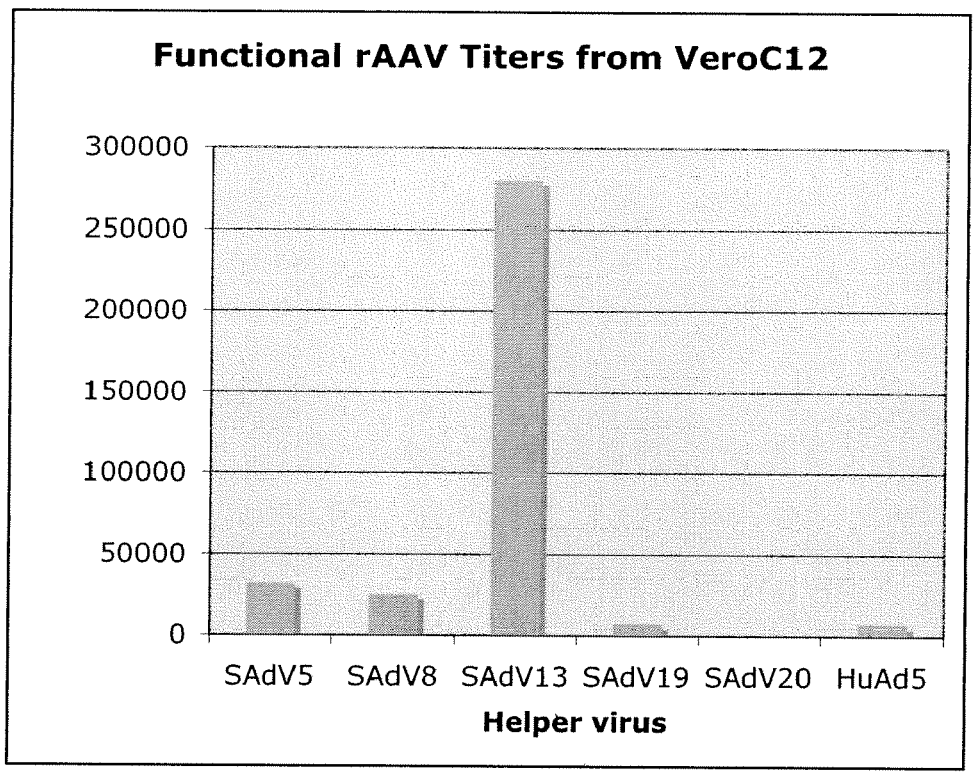
FIG. 2 depicts infectious rAAV titers produced by VeroC2 cells upon infection with various helper viruses. Lysates were produced as described and then used for co-infection of HeLa C12 cells with human Ad5. Lysates produced with SAdV-2, 3, 10, 11, 16 or mock-infected did not produce any detectable infectious rAAV (<100 IU/ml).

Vero cell lysates (from Vero cells infected with SAdV-5, -8, -13, -19 and -20) were applied to HeLa-derived C12 cells that had simultaneously been infected with Ad5. HeLa C12 cells are an "indicator" line that contains the AAV2 rep and cap genes. Upon co-infection with rAAV and Ad5, the rAAV genome is massively amplified ($10^4$-$10^5$ logs) due to the presence and activity of the rep gene. Therefore, vector genome and transgene amplification are sensitive readouts for rAAV infection. Accordingly, serial dilutions ($10^{-1}$ to $10^{-8}$) of VeroC2 cell lysates infected with various adenoviruses were generated and used to infect C12 cells also infected with Ad5 to stimulate rep dependent rAAV vector genome replication. Twenty hr. post-infection the wells were examined in the inverted fluorescent microscope. The total number of green cells were counted in wells with fewer than 50, and those numbers were used to generate an infectious rAAV titer (FIG. 2).

These data further confirm that SAdV-13 was the most effective helper to produce functional rAAV from the VeroC2 cell line.

Example 5

Vero lines were also developed that could be used to produce rAAV by an alternative, scalable method. In this system, AAV rep and cap genes are integrated into the Vero cellular DNA, but the rAAV genome is delivered by an adenovirus-AAV hybrid, where an rAAV genome is integrated into the E1 region of an adenovirus vector and packaged in the adenovirus capsid. The cells are also concurrently infected with a wild type adenovirus that provides helper functions for rAAV production and also allows for replication of the Ad/AAV hybrid by providing E1 gene products that are deleted in the Ad/AAV hybrid virus. Control experiments (not shown) had demonstrated that E1 products from SAdV-13 could allow replication by an E1 deleted HuAd5 in Vero cells.

To adapt such an Ad/AAV hybrid packaging system to Vero cells, cell lines were first selected that contained the AAV rep and cap genes. All these lines were derived from the World Health Organization (WHO) certified stock of Vero cells, which was provided by the ATCC with a release from the FDA. Two constructs were used to make the stable cell lines. Both have neomycin resistance genes for selection and the rep gene from AAV2, while one has the cap gene from AAV1 (rep2cap1neo) and the other has the cap gene from AAV2 (rep2cap2neo). The two constructs were transfected into WHO Vero cells and selected for stable integration with 600 µg/ml G418. A total of 387 rep2cap1 lines and 338 rep2cap2 lines were selected. Previous experience with rAAV producer cell lines indicated that robust rep gene amplification was key to high-titer cell line. Since this is amenable to high throughput screening, an initial screen based on this property was performed. Cells were infected with SAdV-13, then after 5 days, they were lysed by the addition of ⅒oth volume of 4 M NaOH, 50 mM EDTA, and 10 µg/ml herring sperm DNA. The denatured cell lysate was transferred to a positively charged nylon membrane by using a "dot blot" filtration device. The level of rep DNA amplification was determined by using a rep radiolabeled hybridization probe. The cell lines corresponding to the most highly radioactive spots were selected for further analysis. There were ten rep2cap1 and 8 rep2cap2 lines that were subjected to further characterization. These were co-infected with SAdV-13 and an Ad/AAV hybrid virus to determine rAAV vector yields using this second production platform.

Five rep2cap1 packaging cell lines and five rep2cap2 cell lines were co-infected with SAdV-13 and an Ad/AAV hybrid virus (Ad/AAV β-gal) that contained a rAAV genome harboring the β-galactosidase gene integrated into the E1 region of human Ad5. The test packaging cell lines were infected with SAdV-13 at a MOI of 1 and 20 hr later infected with Ad/AAV β-gal at a MOI of 3. After 5 days, cells were lysed by 4 rounds of rapid freezing and thawing and clarified lysates generated by centrifugation and heat treatment to inactivate residual adenovirus. A DRP assay was performed using a primer/probe combination that is specific to the β-galactosidase transgene (Table 1). The productivity for the highest producing cell lines identified in this experiment. rAAV production by Vero rep2cap1 and rep2cap2 cell lines co-infected with SAdV-13 and Ad/AAV β-gal hybrid virus are shown in Table 2.

TABLE 2

| Cell line | AAV Capsid gene source | rAAV DRP/cell |
|---|---|---|
| R2C1.SF.1B1 | Serotype 1 | 1706 |
| R2C2.CA.1D3 | Serotype 2 | 2316 |
| R2C2.SF.1B1 | Serotype 2 | 2286 |

An additional control experiment was done to show that there was no residual adenovirus present that could be making β-gal sequences DNAse resistant. Recombinant adenovirus containing the β-gal transgene should have been denatured by the 56° C. heating step, and to confirm this the DRP assay was repeated but with a human Ad5 E4 primer probe set. The numbers of copies of adenovirus present by using this qPCR primer/probe set were at least 10-fold lower than the β-gal copies present in the lysates, indicating that the vast majority of the DRP values were being contributed by rAAV/β-gal particles.

This initial experiment provided proof of concept that the Ad/AAV hybrid packaging type cell line could be adapted to Vero cells. The approach has been further optimized by selecting a somewhat more productive line (R2C1.CA.8C4) for production of rAAV 1. Three other simian adenoviruses were additionally tested that had shown some activity with Vero C2 cells (SAdV-5, 8 and 19) in Example 1. These helper viruses had sub-detectable levels of rAAV production in this rAd/AAV hybrid system. A key aspect of this packaging system as opposed to the producer cells is that one needs only a single cell line to produce multiple different rAAV vectors of the same serotype. This could increase efficiency and reduce cost since it would not be necessary to qualify a new cell line for each rAAV vector produced.

Example 6

An additional rAd/AAV hybrid virus encoding a heterologous protein smaller than β-galactosidase and more similar in size to proteins used for therapeutic purposes was used to optimize production parameters. The rAd/AAV hybrid virus contained the enhanced green fluorescent protein (eGFP) transgene. This gene was contemplated to package more efficiently and yield greater levels of rAAV.

Two Vero derived AAV packaging cell lines were isolated following plasmid DNA transfection. The R2C1.CA.8C3 line contains the rep gene from AAV2 and the cap gene from AAV1, while the R2C2.CA.1D3 line contains both rep and cap from AAV2. To evaluate the packaging ability of Vero-derived cells with the eGFP containing rAd/AAV hybrid, the cell lines were co-infected with the rAd/AAV hybrid virus and SAdV-13 at variable timing. The rAd/AAV hybrid virus was used at 100 vector genomes per cell, while SAdV-13 was used at 1 $TCID_{50}$ per cell.

Timing of infection was varied to look at the effects on rAAV yield. Infection with the rAd/AAV hybrid virus occurred at the following times relative to the SAdV-13: 4 hours before, at the same time, or 4-24 hours after at 4 hour intervals. To determine yield, cells were harvested at maximal cytopathic effect (5 days for SAdV-13), lysed by 4 freeze thaw cycles and the lysates were then diluted 1:2000. They were then treated sequentially with DNAse and Proteinase K, and assayed by real time PCR. rAAV present in the clarified cell lysate was achieved by qPCR to measure DNAse resistant vector genomes as described previously. The levels for SAdV-13 are shown in Tables 3 and 4.

Table 3 depicts AAV1 GFP production while Table 4 depicts AAV2 eGFP production.

TABLE 3

AAV1 eGFP Production

| Timing of Ad hybrid addition (hours) | SAdV-13 DRP/Cell |
|---|---|
| −4 | 3555 |
| 0 | 9216 |
| +4 | 7966 |
| +8 | 12427 |
| +12 | 11634 |
| +16 | 16272 |
| +20 | 7262 |
| +24 | 8522 |

TABLE 4

AAV2 eGFP Production

| Timing of Ad hybrid addition (hours) | SAdV-13 DRP/Cell |
|---|---|
| −4 | 86561 |
| 0 | 73977 |
| +4 | 58256 |
| +8 | 83783 |
| +12 | 62963 |
| +16 | 60230 |
| +20 | 149504 |
| +24 | 98333 |

The data indicates that high levels of rAAV productivity are possible with this system. Up to 150,000 DNAse resistant particles per cell were documented for the rAAV2.eGFP vector. Optimal production conditions for infection varied between cell lines, with the most effective timing being rAd/AAV hybrid virus infection 16-24 hours after SAdV-13 virus infection.

Example 7

A SadV-13 was molecularly cloned and sequenced as follows.

Figure 3:
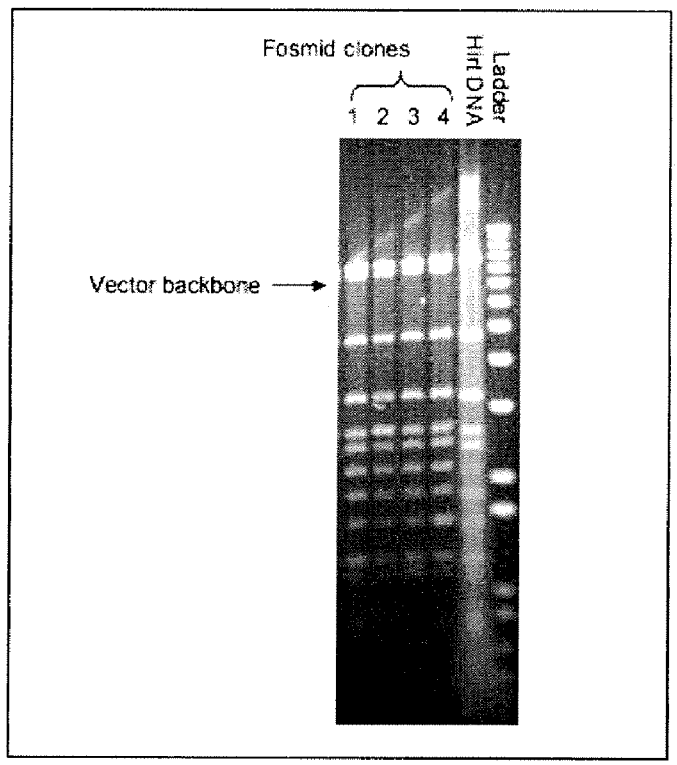
FIG. 3 depicts the BamHI restriction pattern of four fosmid clones compared to SAdV-13 infected cell Hirt DNA showing an identical banding pattern consistent with isolation of an SAdV-13 molecular clone.

Low molecular weight DNA was isolated from SAdV-13 infected Vero cells by a modified Hirt DNA extraction procedure [Hirt et al., Journal of Molecular Biology, 26(2): 365-369 (1967)], and then the terminal protein was removed by treatment with Klenow fragment in the presence of three of the four dNTPs followed by S1 nuclease [Berkner et al., Nucleic Acids Res 11(17): 6003-20 (1983)]. The SAdV-13 virus genomes were then cloned into a fosmid vector (Epicentre Copy Control System) and resulting clones analyzed by digestion with BamHI restriction enzyme for an identical restriction pattern as that observed for the bulk Hirt DNA. Four clones were identified with the expected pattern (FIG. 3). Clone #3 (SAdV13-PME12) was subsequently selected for high-throughput 454 deep sequencing.

Several clones were selected and the terminal sequences determined. Sequence of the inverted terminal repeats (ITRs) for six independent clones was obtained and shared significant homology to other published adenovirus ITR sequences. Two kinds of heterogeneity in the clones' ITR sequence was observed that were otherwise identical except for orientation. The first was that there were variable numbers of nucleotides (4-18) missing from the terminal repeat ends. Secondly, in some cases short duplications of 100-400 bp of sequence was appended to intact ITRs.

Figure 4:
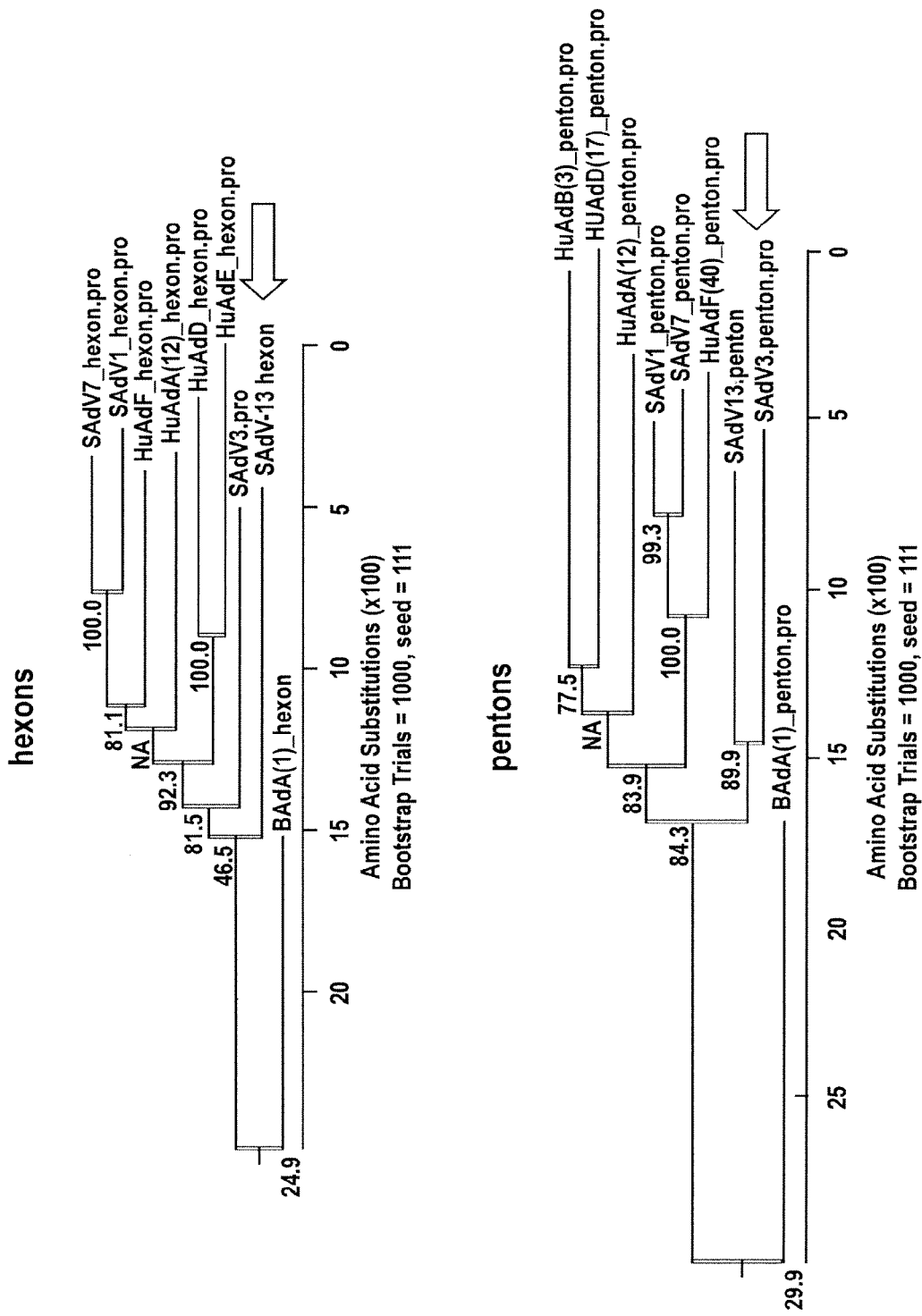
FIG. 4 depicts phylogenetic trees for hexon and penton protein sequences from various simian (SAdV) and human (HuAdV) adenoviruses. Bovine adenovirus sequence (BoAdA) was used to root the tree and the position of SAdV-13 is marked with arrows.

Clone SAdV13-PME12 was selected for complete sequencing and possessed a 4 bp deletion at the 5' end and a 12 bp deletion at the 3' end. A portion of the resulting sequence matched exactly the previously reported VA RNA gene sequence [Kidd et al., Virology 207(1): 32-45 (1995)] supporting that this sequence is SAdV-13. Translation of the virus sequence resulted in the clear delineation of identity between this novel isolate and previously published adenoviral genomes. SAdV-13 is clearly related to other primate adenoviruses without being notably similar to any other previously published adenovirus genomes. Phylogenetic analysis of the deduced amino acid sequences of the hexon and penton proteins is shown in FIG. 4 and the complete virus genome sequence provided as SEQ ID NO: 16. This sequence, along with the putative protein sequences expressed therefrom, are depicted in Table 5 below.

TABLE 5

| SEQ ID NO: | Description |
| --- | --- |
| 16 | SAdV-13 Viral Genome |
| 17 | E4 orf 2 |
| 18 | E4 orf 3 |
| 19 | E4 orf 4 |
| 20 | E4 34K |
| 21 | Fiber |
| 22 | E3 14.7 (15.3) |
| 23 | U exon |
| 24 | E3 RID-beta |
| 25 | E3 RID-alpha |
| 26 | E3 CR1 beta1 |
| 27 | E3 CR1-alpha1 |
| 28 | E3 12.5K |
| 29 | pVIII |
| 30 | 33K? |
| 31 | 22K |
| 32 | 100K |
| 33 | DBP |
| 34 | Protease |
| 35 | Hexon |
| 36 | pVI |
| 27 | V |
| 38 | pX? |
| 39 | pVII |
| 40 | III (penton base) |
| 41 | pTP |
| 42 | pol |
| 43 | pIIIa |
| 44 | 52K |
| 45 | IVa2 C-terminus |

TABLE 5-continued

| SEQ ID NO: | Description |
| --- | --- |
| 46 | IX |
| 47 | E1B 55K |
| 48 | E1B 19K |
| 49 | E1A |
| 50 | E4 orf 1 |

Example 8

The DNA sequence of the SAdV-13 (PME-12) clone enabled the development of a quantitative real-time PCR assay to detect SAdV-13 genomes. This assay is useful for the rapid, sensitive and precise measurement of the SAdV-13 and permits rapid optimization of virus infection conditions for increased rAAV production in this production platform.

Specifically, samples are quantitated by dilution of the sample 100 to 10,000-fold in 50 mM KCl, 10 mM Tris pH 8.0, and 5 mM $MgCl_2$. Samples are then digested in a 50 µl volume with 175 U of DNAse I at 37° C. for 30 minutes to remove non-encapsidated viral DNA. After heating at 95° C. for 10 minutes to inactivate DNAse I, the sample is treated with 200 µg/ml proteinase K at 50° C. for 1 hour to degrade the viral capsid and other cellular proteins. After treatment at 95° C. for 30 min to inactivate Proteinase K, the viral genomes are quantitated by real time PCR with a Taqman® primer probe set as follows:

```
Forward primer:
5'-CTTGAAGCCACGCAAGTTTA-3'        (SEQ ID NO: 13)

Reverse primer:
5'-TGCAAATAATCCAGCAAAGC-3'        (SEQ ID NO: 14)

Probe:
6-FAM-CATGTTTGCTCATCGCCCGG-TAMRA  (SEQ ID NO: 15)
```

Quantitation is carried out by comparison with a plasmid standard curve.

While the present invention has been described in terms of various embodiments and examples, it is understood that variations and improvements will occur to those skilled in the art. Therefore, only such limitations as appear in the claims should be placed on the invention.

What is claimed is:

1. A method of producing infectious recombinant adeno-associated virus (rAAV) comprising the steps of:
   a) stably transforming a Vero cell with a rAAV genome and AAV rep/cap genes to generate a Vero producer cell,
   b) infecting the Vero producer cell with simian adenovirus 13 (SAdV-13) helper virus and
   c) culturing the Vero producer cell of step b) to produce rAAV.

2. A method of producing infectious recombinant adeno-associated virus (rAAV) comprising the steps of:
   a) stably transforming the Vero cell with AAV rep/cap genes to generate a Vero packaging cell,
   b) introducing a rAAV genome into the Vero packaging cell,
   c) infecting the Vero packaging cell of step b) with simian adenovirus 13 (SAdV-13) helper virus and
   d) culturing the Vero packaging cell of step c) to produce rAAV.

3. The method of claim 2, wherein the rAAV genome is introduced into the Vero packaging cell by infection with a rAd/AAV hybrid.

4. A method of producing infectious recombinant adeno-associated virus (rAAV) comprising the steps of:
   a) introducing a rAAV genome and AAV rep/cap genes into a Vero cell,
   b) infecting the Vero cell of step a) with simian adenovirus 13 (SAdV-13) helper virus and
   c) culturing the Vero cell of step b) to produce rAAV.

5. The method of claim 4 wherein steps a) and b) occur concurrently.

6. The method of claim 4 wherein the Vero cell is a packaging cell.

7. The method of any of claims 1-6 further comprising the step of isolating the rAAV produced by the cell.

8. The method of claim 3, wherein the Vero cell is infected with the rAd/AAV 16-24 hours after helper virus infection.

9. A method of producing infectious rAAV comprising culturing a Vero producer cell under conditions permissive for rAAV production, wherein the Vero producer cell comprises simian adenovirus 13 (SAdV-13) helper virus.

10. The method of any of claims 4-6, 3, wherein the SAdV-13 helper virus is SAdV-13 PME-12.

11. The method of 7 wherein the SAdV-13 helper virus is SAdV-13 PME-12.

* * * * *